(12) United States Patent
Tang

(10) Patent No.: US 8,486,675 B2
(45) Date of Patent: Jul. 16, 2013

(54) PROTEIN CONCENTRATES AND ISOLATES, AND PROCESSES FOR THE PRODUCTION THEREOF FROM MACROALGAE AND/OR MICROALGAE

(75) Inventor: Qingnong Nelson Tang, Saskatoon (CA)

(73) Assignee: Bioexx Specialty Proteins Ltd., Toronto, Ontario (CA)

( * ) Notice: Subject to any disclaimer, the term of this patent is extended or adjusted under 35 U.S.C. 154(b) by 253 days.

(21) Appl. No.: 12/943,858

(22) Filed: Nov. 10, 2010

(65) Prior Publication Data

US 2012/0021457 A1  Jan. 26, 2012

Related U.S. Application Data

(60) Provisional application No. 61/260,148, filed on Nov. 11, 2009.

(51) Int. Cl.
*C12P 1/02* (2006.01)
(52) U.S. Cl.
USPC ............................................. 435/171
(58) Field of Classification Search
USPC .................................. 435/68.1, 171
See application file for complete search history.

(56) References Cited

U.S. PATENT DOCUMENTS

| | | | |
|---|---|---|---|
| 3,966,971 A | 6/1976 | Morehouse et al. |
| 4,079,048 A | 3/1978 | Chao |
| 4,889,921 A | 12/1989 | Diosady et al. |
| 5,844,096 A | 12/1998 | Hinrichs et al. |
| 6,005,076 A | 12/1999 | Murray |
| 6,132,795 A | 10/2000 | Holbrook et al. |
| 6,800,308 B2 | 10/2004 | Maenz et al. |
| 6,905,713 B2 | 6/2005 | Diosady et al. |
| 6,992,173 B2 | 1/2006 | Milanova et al. |
| 7,001,990 B2 | 2/2006 | Hiron et al. |
| 7,087,720 B2 | 8/2006 | Murray et al. |
| 7,090,887 B2 | 8/2006 | Newkirk et al. |
| 7,211,286 B2 | 5/2007 | Hiron |
| 7,211,288 B2 | 5/2007 | Hiron |
| 7,309,773 B2 | 12/2007 | Green et al. |
| 2003/0021884 A1 | 1/2003 | Murray |
| 2003/0109679 A1 | 6/2003 | Green et al. |
| 2003/0124241 A1 | 7/2003 | Wesdal |
| 2003/0125526 A1 | 7/2003 | Barker et al. |
| 2004/0005395 A1 | 1/2004 | Hiron et al. |
| 2004/0034200 A1 | 2/2004 | Logie et al. |
| 2004/0039174 A1 | 2/2004 | Barker et al. |
| 2004/0077838 A1 | 4/2004 | Green et al. |
| 2004/0197378 A1 | 10/2004 | Murray |
| 2004/0254353 A1 | 12/2004 | Barker et al. |
| 2005/0031767 A1 | 2/2005 | Schweizer et al. |
| 2005/0042715 A1 | 2/2005 | Murrah et al. |
| 2005/0064086 A1 | 3/2005 | Hiron et al. |
| 2005/0107593 A1 | 5/2005 | Green et al. |
| 2005/0165220 A1 | 7/2005 | Barker et al. |
| 2005/0181112 A1 | 8/2005 | Schweizer et al. |
| 2005/0208021 A1 | 9/2005 | Cabs |
| 2005/0226909 A1 | 10/2005 | Westdal |
| 2005/0249828 A1 | 11/2005 | Logie et al. |
| 2005/0249866 A1 | 11/2005 | Murray |
| 2005/0255226 A1 | 11/2005 | Schweizer et al. |
| 2005/0283001 A1 | 12/2005 | Schweizer et al. |
| 2006/0035003 A1 | 2/2006 | McMindes et al. |
| 2006/0073250 A1 | 4/2006 | Mozaffar et al. |
| 2006/0121171 A1 | 6/2006 | Schweizer et al. |
| 2006/0128020 A1 | 6/2006 | Cabs |
| 2006/0193965 A1 | 8/2006 | Newkirk et al. |
| 2006/0205929 A1 | 9/2006 | Milanova et al. |
| 2006/0217318 A1 | 9/2006 | Wu |
| 2006/0281904 A1 | 12/2006 | Green |
| 2006/0286281 A1 | 12/2006 | Hiron et al. |
| 2007/0004908 A1 | 1/2007 | Gosnell et al. |
| 2007/0015910 A1 | 1/2007 | Barker et al. |
| 2007/0065567 A1 | 3/2007 | Segall et al. |
| 2007/0098876 A1 | 5/2007 | Hiron |
| 2007/0178566 A1 | 8/2007 | Schweizer et al. |
| 2007/0191593 A1 | 8/2007 | Green et al. |
| 2007/0237877 A1 | 10/2007 | Diosady et al. |
| 2007/0244300 A1 | 10/2007 | Schweizer et al. |
| 2007/0269583 A1 | 11/2007 | McMindes et al. |
| 2008/0125577 A1 | 5/2008 | Gosnell et al. |
| 2008/0166469 A1 | 7/2008 | Schweizer et al. |
| 2008/0299282 A1 | 12/2008 | Schweizer et al. |
| 2008/0319171 A1 | 12/2008 | Barker et al. |
| 2009/0036655 A1 | 2/2009 | Segall et al. |
| 2009/0076252 A1 | 3/2009 | Barker et al. |
| 2009/0081355 A1 | 3/2009 | Murray |
| 2009/0175999 A1 | 7/2009 | Segall et al. |
| 2009/0203880 A1 | 8/2009 | Gosnell et al. |
| 2009/0286961 A1 | 11/2009 | Tang |

FOREIGN PATENT DOCUMENTS

| | | |
|---|---|---|
| CA | 2450388 | 5/2004 |
| CA | 2724391 | 11/2009 |
| WO | 02/089597 | 11/2002 |
| WO | 03/088760 | 10/2003 |
| WO | 2007/003044 | 1/2007 |
| WO | 2008/024840 | 2/2008 |

OTHER PUBLICATIONS

Venkataraman et al. "Studies on the extractability of proteins from the alga *Scenedesmus acutus*" Archiv flier Hydrobiologie, Supplement (1979), 56(1),114-26.*

(Continued)

*Primary Examiner* — Sandra Saucier
*Assistant Examiner* — Thane Underdahl
(74) *Attorney, Agent, or Firm* — Koppel, Patrick, Heybl & Philpott; Michael J. Ram

(57) ABSTRACT

Protein concentrates and protein isolates, in addition to processes for the production of protein concentrates and protein isolates, are disclosed. In particular, the disclosure relates to the removal of fiber from macroalgae and/or microalgae using low g-force centrifugation.

46 Claims, 38 Drawing Sheets

OTHER PUBLICATIONS

Folawiyo, Y.L. and Apenten, R.K.O., Effect of pH and Ionic Strength on the Heat Stability of Rapeseed 12S Globulin (Cruciferin) by the ANS Fluorescence Method, Journal of Science Food Agric., 1996, pp. 241-246, vol. 70.

McCurdy, S.M. and March, B.E., "Processing of Canola Meal for Incorporation in Trout and Salmon Diets", Jaocs, 1992, pp. 213-220, vol. 69, No. 3.

Gerbanowski, A., Malabat, C., Rabiller, C., Gueguen, J., "Grafting of Aliphatic and Aromatic Probes on Rapeseed 2S and 12S Proteins: Influence on Their Structural and Physiochemical Properties," J. Agric. Food Chem., 1999, 47:5218-5226.

Vioque et al., "Production and Characterization of an Extensive Rapeseed Protein Hydrolystate". Journal of the American Oil Chemists' Society, 76(7):819-23, 1999.

Chronakis, Ioannis S., Gelatin of Edible Blue-Gree Algae Protein Isolate (Spirulina Platensis Strain Pacifica): Thermal Transitions, Rheological Properties, and Molecular Forces Involved. J. Agric. Food Chem. 49:888-898, 2001.

Dawczynski, C., Schbert, R., Jahreis, G. Amino Acids, Fatty Acids, and Dietary Fibre in Edible Seaweed Products. Food Chemistry, 103:891-899, 2007.

Morris, H.J., Almarales, A., Carillo, O., Bermudez, R.C. "Utilisation of *Chlorella vulgaris* Cell Biomass for the Production of Enzymatic Protein Hydrolysates". Bioresource Technology. 99:7723-7729, 2008.

* cited by examiner

PROTEIN CONCENTRATES AND ISOLATES, AND PROCESSES FOR THE PRODUCTION THEREOF FROM MACROALGAE AND/OR MICROALGAE

PRIORITY INFORMATION

This application is claims the benefit of U.S. Provisional Application No. 61/260,148 filed on Nov. 11, 2009 and entitled PROTEIN CONCENTRATES AND ISOLATES, AND PROCESSES FOR THE PRODUCTION THEREOF FROM MICROALGAE AND/OR MACROALGAE, the contents of which of which are expressly incorporated herein by reference.

FIELD OF THE DISCLOSURE

The present disclosure relates to protein concentrates and protein isolates comprising combinations of proteins, peptides and amino acids, as well as processes for their production. In particular, the disclosure relates to a process for removing fiber from macroalgae and/or microalgae to produce edible protein products.

BACKGROUND

Macroalgae and/or microalgae constitute a large source of available protein. Depending upon the identity, some macroalgae and/or microalgae contain a high amount of fiber, as well as other antinutritional factors and undesirable compounds, such as glucosinolates, phytic acid or phytates, sinapine and sinigrin. The fiber and antinutritional factors present in the protein render the macroalgae and/or microalgae unattractive as a source of protein for commercial uses.

One method of separating the protein from the fiber, antinutritional factors and other undesirable compounds has been to dissolve the macroalgae and/or microalgae protein in a high ionic strength (i.e. high salt content) aqueous solution. This results in the protein dissolving in the aqueous solution, while the fiber is insoluble. However, the salt is difficult and uneconomical to remove and recover from the resultant protein solution.

SUMMARY OF THE DISCLOSURE

Herein, a process for the production of protein concentrates and protein isolates is disclosed. In addition, protein concentrates and protein isolates produced in accordance with the processes of the disclosure are also disclosed. In particular, the disclosure relates to a process for the facile removal of fiber, antinutritional factors and other constituents from macroalgae and/or microalgae containing such, to produce protein concentrates and protein isolates of high quality.

In another embodiment of the present disclosure, a process for the production of a protein concentrate possessing a protein content of about 30% to about 75% is disclosed.

Accordingly, the disclosure includes a process for the production of a protein concentrate from macroalgae and/or microalgae, comprising:
1) removing fiber from the macroalgae and/or microalgae to form a fiber depleted meal, comprising either:
    i) mixing the macroalgae and/or microalgae with a mixing solvent to form a first mixture; and
        separating and removing fiber from the first mixture, optionally by using a mesh screen;
        optionally treating the mixture with phytase at a temperature and a pH suitable for phytase activity; or
    ii) mixing macroalgae and/or microalgae with water to form a second mixture; and
        optionally adjusting the pH of the second mixture to a pH suitable for enzyme activity, optionally about 3 to about 7, optionally 4 to 6; and
        adding cellulase complex or other enzyme having fiber hydrolysis activity to the second mixture and heating to a temperature suitable for enzyme activity, to hydrolyze the fiber;
        optionally treating the mixture with phytase at a temperature and a pH suitable for phytase activity,
2) washing the fiber depleted meal with an extraction solvent to form an extract and a washed defatted or protein-enriched meal;
3) separating the extract from the washed macroalgae and/or microalgae;
4) optionally repeating steps 2) and 3) at least once; and
5) optionally desolventizing the washed macroalgae and/or microalgae to form a protein concentrate.

In another embodiment, the mixing solvent comprises water, methanol, ethanol or isopropanol, and mixtures thereof. In a further embodiment, the solvent is water or ethanol, and mixtures thereof. In an embodiment of the disclosure, the macroalgae and/or microalgae is mixed with a mixing solvent in a ratio of about 3 to about 10 parts solvent to about 1 part of the macroalgae and/or microalgae, optionally about 4 to about 8, or about 4 to about 6, on a weight-to-weight basis.

In another embodiment of the disclosure, the mixture is screened through a mesh screen of typically about 10 to about 200 US mesh size, optionally a mesh screen of about 20 to about 200 US mesh size. In another embodiment, the mesh size is 40 US mesh size.

In an embodiment of the present disclosure, the macroalgae and/or microalgae is mixed thoroughly with water to form the second mixture. In an embodiment, the mixing of water and the macroalgae and/or microalgae comprises using a wet mill or an inline mixer.

In another embodiment of the present disclosure, the cellulase complex is added to the second mixture in an amount of about 1 gram to about 10 grams for about every 1 kg of dry solids of the macroalgae and/or microalgae (about 0.1% to about 1%). In a further embodiment, the cellulase complex is mixed with the second mixture for about 0.5 hours to about 5 hours. In another embodiment, the cellulase complex is mixed with the second mixture for about 1 to about 3 hours.

In another embodiment of the disclosure, the second mixture with the added cellulase complex is heated to a temperature of about 30° C. to about 60° C., suitably about 40° C. to about 60° C.

In an embodiment, the cellulase complex comprises at least one of endocellulase, exocellulase, cellobiohydrolase, cellobiase, endohemicellulase and exohemicellulase.

In an embodiment of the disclosure, the extraction solvent comprises methanol, ethanol or isopropanol, and mixtures thereof. In a further embodiment, the extraction solvent comprises ethanol or water, and mixtures thereof.

In an embodiment of the present disclosure, the first or second mixture is washed at least once with about 5% to about 100%, optionally about 25% to about 85%, or about 50% to about 85%, or about 60% to about 85%, of the extraction solvent (v/v) in water.

In an embodiment of the present disclosure, the ratio of the extraction solvent to the first or second mixture is about 5% to about 95%, optionally about 10% to about 90%, about 20% to about 70%, or about 40% to about 80% (v/v) (extraction solvent to first or second mixture).

In an embodiment of the present disclosure, the first or second mixture is washed with the extraction solvent at a temperature of about 10° C. to about 90° C. In another embodiment, the first or second mixture is washed with the extraction solvent at a temperature of about 20° C. to about 60° C. In a further embodiment, the first or second mixture is washed with the extraction solvent at a temperature of about 20° C. to about 25° C.

In another embodiment of the present disclosure, the extract is separated from the washed macroalgae and/or microalgae by centrifugation, vacuum filtration, pressure filtration, decantation or gravity draining in an extractor.

In another embodiment of the present disclosure, steps 2) and 3) are repeated at least twice.

In another embodiment of the present disclosure, the process further comprises the step of drying the washed macroalgae and/or microalgae to form the protein concentrate. In a further embodiment, the washed macroalgae and/or microalgae is dried in a vacuum dryer, fluidized bed dryer, ring dryer or spray dryer. In another embodiment, the washed macroalgae and/or microalgae is dried to a moisture content of about 0.5% to about 12%, optionally about 1% to about 10%, about 4% to about 8%. In a further embodiment, the washed macroalgae and/or microalgae is dried to a moisture content of about 6%.

In another embodiment of the present disclosure, the extract is desolventized and dried to form a high sugar fraction. In an embodiment, the extract is desolventized by spray drying, drum drying or vacuum drying.

In an embodiment of the present disclosure, a process for the production of a protein concentrate possessing a protein content of about 75% to about 90% is disclosed. In another embodiment, the protein concentrate is hydrolyzed to produce peptides and free amino acids. In another embodiment, the hydrolyzed protein concentrate comprises peptides and/or free amino acids.

The disclosure also includes a process for the production of a protein concentrate from macroalgae and/or microalgae, comprising:
  removing fiber from the macroalgae and/or microalgae, comprising:
    i) mixing the macroalgae and/or microalgae with a mixing solvent to form a mixture;
      separating fiber from the mixture, optionally by screening the mixture to remove fiber,
      optionally adjusting the pH of the mixture to a pH of about 4.5 to about 8.0, optionally about 6.5 to about 7.5, or optionally about 7;
      optionally treating the mixture with phytase at a temperature and a pH suitable for phytase activity,
      optionally milling the mixture;
      separating fiber, optionally by centrifuging the mixture, to remove fiber,
      thereby forming a protein slurry; and
    ii) separating the protein slurry, optionally by centrifuging the protein slurry, to form a protein precipitate and a soluble protein fraction;
    iii) washing the protein precipitate with an extraction solvent at least once and separating, optionally by centrifuging, to form a purified protein precipitate;
    iv) optionally drying the purified protein precipitate to form the protein concentrate.

In another embodiment of the disclosure, the mixing solvent comprises water, methanol, ethanol, or isopropanol, and mixtures thereof. In a further embodiment, the mixing solvent comprises water or ethanol, and mixtures thereof. In another embodiment, the ratio of macroalgae and/or microalgae to the mixing solvent is about 1:3 to about 1:20. In a further embodiment, the ratio is about 1:6 to about 1:10. In an embodiment, the ratio is about 1:6 to about 1:8.

In another embodiment of the disclosure, the mixture is screened through a mesh screen of typically about 10 to about 200 US mesh size, optionally a mesh screen of about 20 to about 200 US mesh size. In another embodiment, the mesh size is 40 US mesh size.

In another embodiment of the present disclosure, the pH of mixture is adjusted with aqueous sodium hydroxide. In an embodiment, the aqueous sodium hydroxide has a concentration of about 1% to about 40% by weight of sodium hydroxide. In a further embodiment, the concentration of sodium hydroxide is about 5% to about 30% sodium hydroxide.

In another embodiment, the optional milling step comprises using a wet mill.

In an embodiment, the mixture is centrifuged using a decanting centrifuge. In an embodiment, the mixture is centrifuged with a decanting centrifuge at a speed of about 500 rpm to about 6000 rpm. In another embodiment, the speed is about 1500 rpm.

In an embodiment of the disclosure, the protein slurry is centrifuged using a decanter or disc stack centrifuge. In a further embodiment, the protein slurry is centrifuged at a speed of about 2500 rpm to about 8500 rpm.

In another embodiment of the disclosure, the extraction solvent is water, methanol, ethanol or isopropanol, and mixtures thereof. In a further embodiment, the extraction solvent is water or ethanol, and mixtures thereof. In an embodiment, the extraction solvent is water. In an embodiment, the protein precipitate is washed at least twice with the extraction solvent.

In an embodiment of the present disclosure, the washed protein precipitate is centrifuged with a disc stack centrifuge at a speed of about 7500 rpm to about 8500 rpm.

In an embodiment of the disclosure, the purified protein precipitate is dried in a vacuum dryer, fluidized bed dryer, ring dryer or spray dryer to form the protein concentrate. In a further embodiment, the protein concentrate is dried to a moisture content of about 1% to about 10%. In another embodiment, the protein concentrate is dried to a moisture content of about 6%.

In another embodiment, the protein concentrate comprises a hydrolyzed protein concentrate. In another embodiment, the protein concentrate is hydrolyzed to produce peptides and free amino acids. In another embodiment, the hydrolyzed protein concentrate comprises peptides and/or free amino acids.

In another embodiment of the present disclosure, a process for the production of a protein isolate possessing a protein content of greater than about 90% is disclosed.

Accordingly, the disclosure includes a process for the production of a protein isolate from macroalgae and/or microalgae, comprising:
  removing fiber from the macroalgae and/or microalgae, comprising:
    i) mixing the macroalgae and/or microalgae with a mixing solvent to form a mixture;
      separating fiber from the mixture to remove fiber,
      optionally adjusting the pH of the mixture to a pH of about 6.0 to about 8.0, optionally about 6.5 to about 7.5, or optionally about 7;
      optionally milling the mixture;
      optionally treating the mixture with phytase at a temperature and a pH suitable for phytase activity, separating fiber, optionally by centrifuging the mixture, to remove fiber,
thereby forming a protein slurry;
ii) separating the protein slurry, optionally by centrifuging the protein slurry, to form a protein precipitate and a soluble protein fraction;
iii) filtering the soluble protein fraction to separate it from protein precipitate; and
iv) optionally drying the soluble protein to form the protein isolate.

In another embodiment of the disclosure, the mixing solvent comprises water or a salt solution. In an embodiment, the salt solution comprises less than 5%, optionally about 3% to about 4%, or 3.5% by weight of salt in solution. In a further embodiment, the mixing solvent comprises water. In another embodiment, the ratio of macroalgae and/or microalgae to the mixing solvent is about 1:3 to about 1:20. In a further embodiment, the ratio is about 1:6 to about 1:10. In an embodiment, the ratio is about 1:6 to about 1:8.

In another embodiment of the present disclosure, the pH of mixture is adjusted with aqueous sodium hydroxide. In an embodiment, the aqueous sodium hydroxide has a concentration of about 1% to about 40% by weight of sodium hydroxide. In a further embodiment, the concentration of sodium hydroxide is about 5% to about 30% sodium hydroxide.

In another embodiment of the disclosure, the mixture is screened through a mesh screen of about 10 to about 200 US mesh size, optionally a mesh screen of about 20 to about 200 US mesh size. In an embodiment, the mesh size is 40 US mesh size.

In an embodiment, the mixture is centrifuged using a decanting centrifuge. In an embodiment, the mixture is centrifuged with a decanting centrifuge at a speed of about 500 rpm to about 6000 rpm. In another embodiment, the speed is about 1500 rpm.

In another embodiment, the optional milling step comprises using a wet mill.

In an embodiment of the disclosure, the protein slurry is centrifuged using a disc stack centrifuge. In a further embodiment, the protein slurry is centrifuged at a speed of about 6500 rpm to about 8500 rpm.

In another embodiment of the disclosure, the soluble protein fraction is filtered using an ultrafiltration or diafiltration apparatus. In a further embodiment, the ultrafiltration or diafiltration apparatus comprises a membrane to filter proteins of larger than about 1,000 daltons, optionally 10,000 daltons, optionally about 30,000 daltons, or about 100,000 daltons. In another embodiment, the ultrafiltration or diafiltration is performed at a temperature of about 1° C. to about 60° C., optionally about 40° C. to about 55° C.

In another embodiment of the disclosure, the soluble protein is dried in a vacuum dryer, fluidized bed dryer, ring dryer or spray dryer to form the protein isolate. In an embodiment, the protein isolate is dried to a moisture content of about 1% to about 10%. In a further embodiment, the protein isolate is dried to a moisture content of about 6%.

In another embodiment, the protein isolate comprises a hydrolyzed protein isolate. In another embodiment, the protein isolate is hydrolyzed to produce peptides and free amino acids. In another embodiment, the hydrolyzed protein isolate comprises peptides and/or free amino acids.

In another embodiment of the present disclosure, a process for the production of a protein isolate possessing a protein content of greater than about 90% is disclosed.

Accordingly, the disclosure includes a process for the production of a protein isolate from macroalgae and/or microalgae, comprising:

removing fiber from the defatted or protein-enriched algae, comprising:
i) mixing the macroalgae and/or microalgae with a mixing solvent to form a mixture;
separating fiber from the mixture to remove fiber,
optionally adjusting the pH of the mixture to a pH of about 6.0 to about 8.0, optionally about 6.5 to about 7.5, or optionally about 7;
optionally milling the mixture;
optionally treating the mixture with phytase at a temperature and a pH suitable for phytase activity,
separating fiber, optionally by centrifuging the mixture, to remove fiber,
thereby forming a protein slurry; and
ii) separating the protein slurry, optionally by centrifuging the protein slurry, to form a protein precipitate and a soluble protein fraction;
iii) mixing the protein precipitate with water to form a protein precipitate mixture and optionally adjusting the pH to a pH suitable for enzyme activity, optionally about 3 to about 7, optionally about 4 to about 6;
iv) adding cellulase complex or other enzyme having fiber hydrolysis activity to the protein precipitate mixture to hydrolyze fiber, typically residual fiber;
v) washing the protein precipitate mixture with an extraction solvent at least once and separating, optionally by centrifuging, to form a protein isolate.

In another embodiment of the disclosure, the mixing solvent comprises water or a salt solution. In an embodiment, the salt solution comprises less than 5%, optionally about 3% to about 4%, or 3.5% by weight of salt in solution. In a further embodiment, the mixing solvent comprises water. In another embodiment, the ratio of macroalgae and/or microalgae to the mixing solvent is about 1:3 to about 1:20. In a further embodiment, the ratio is about 1:6 to about 1:10. In an embodiment, the ratio is about 1:6 to about 1:8.

In another embodiment of the disclosure, the mixture is screened through a mesh screen of about 10 to about 200 US mesh size, optionally a mesh screen of about 20 to about 200 US mesh size. In another embodiment, the mesh size is 40 US mesh size.

In another embodiment of the present disclosure, the pH of mixture is adjusted with aqueous sodium hydroxide. In an embodiment, the aqueous sodium hydroxide has a concentration of about 1% to about 40% by weight of sodium hydroxide. In a further embodiment, the concentration of sodium hydroxide is about 5% to about 30% sodium hydroxide.

In another embodiment, the optional milling step comprises using a wet mill.

In an embodiment, the mixture is centrifuged using a decanting centrifuge. In an embodiment, the mixture is centrifuged with a decanting centrifuge at a speed of about 500 rpm to about 6000 rpm. In another embodiment, the speed is about 1500 rpm.

In an embodiment of the disclosure, the protein slurry is centrifuged using a disc stack centrifuge. In a further embodiment, the protein slurry is centrifuged at a speed of about 6500 rpm to about 8500 rpm.

In another embodiment of the disclosure, the cellulase complex is added to the protein precipitate mixture in an amount of about 0.1% to about 1% by weight of the protein precipitate mixture. In a further embodiment, the cellulase complex is mixed with the protein precipitate mixture for about 0.5 hours to about 5 hours. In another embodiment, the cellulase complex is mixed with the protein precipitate mixture for about 1 to about 3 hours. In a further embodiment, the cellulase complex comprises at least one of endocellulase, exocellulase, cellobiohydrolase, cellobiase, endohemicellulase and exohemicellulase. In an embodiment, the protein precipitate mixture with cellulase complex is heated to a temperature of about 30° C. to about 60° C., optionally about 40° C. to about 60° C.

In another embodiment of the disclosure, the mixing solvent comprises water. In another embodiment, the ratio of macroalgae and/or microalgae to the mixing solvent is about 1:3 to about 1:20. In a further embodiment, the ratio is about 1:6 to about 1:10. In an embodiment, the ratio is about 1:6 to about 1:8.

In another embodiment of the present disclosure, the protein precipitate mixture is centrifuged using a decanter or disc stack centrifuge. In a further embodiment, the protein precipitate mixture is centrifuged at a speed of about 2500 rpm to about 8500 rpm.

In another embodiment of the present disclosure, the protein isolate is subjected to high pressure jet cooking.

In an embodiment of the present disclosure, the protein isolate is hydrolyzed using proteases to form a hydrolyzed protein extract. In a further embodiment, the proteases comprise Alcalase® (serine endopeptidase, typically from *Bacillus subtilis*), or Flavourzyme® (fungal protease/peptidase complex, typically produced from *Aspergillus oryzae* fermentation), both proteases from Novozymes® North America, Inc. In an embodiment, the ratio of Alcalase® to the protein isolate is about 0.1% to about 1%. In another embodiment, the ratio of Alcalase® to the protein isolate is about 0.5%. In a further embodiment, the ratio of Flavourzyme® to the protein isolate is about 0.1% to about 1%. In an embodiment, the ratio of Flavourzyme® to the protein isolate is about 0.5%.

In another embodiment, the protein isolate comprises a hydrolyzed protein isolate. In another embodiment, the protein isolate is hydrolyzed to produce peptides and free amino acids. In another embodiment, the hydrolyzed protein isolate comprises peptides and/or free amino acids.

In another embodiment of the disclosure, there is provided a process for the production of a protein concentrate from macroalgae and/or microalgae, comprising:
  i) mixing the macroalgae and/or microalgae with a mixing solvent to form a mixture and optionally treating the mixture with phytase at a temperature and a pH suitable for phytase activity,
  ii) optionally adjusting the pH of the mixture to a pH of about 2.0 to about 10.0;
  iii) separating fiber from the mixture to form a protein slurry, wherein the protein slurry comprises a soluble protein fraction and an insoluble protein fraction;
  iv) optionally repeating steps i)-iii) by mixing the protein slurry with additional partially defatted, fully defatted or protein-enriched algae;
  v) mixing the protein slurry with an extraction solvent to form an extract and a washed insoluble protein fraction;
  vi) separating the extract from the washed insoluble protein fraction;
  vii) optionally repeating steps v) and vi) at least once; and
  viii) optionally desolventizing the washed insoluble protein fraction to form a protein concentrate.

In another embodiment of the disclosure, the ratio of macroalgae and/or microalgae to mixing solvent is about 1:3 to about 1:30 (w/w).

In another embodiment, the ratio of macroalgae and/or microalgae to solvent is about 1:5 to about 1:20 (w/w). In a further embodiment, the ratio is about 1:6 to about 1:12 (w/w). In an embodiment, the ratio is about 1:8 to about 1:10 (w/w).

In a further embodiment of the disclosure, the mixing solvent comprises water or an aqueous solution comprising a polysaccharide, a salt, such as sodium chloride, potassium chloride, or calcium chloride, or an alcohol. In an embodiment, the mixing solvent is water. In another embodiment, the polysaccharide is guar gum.

In an embodiment, the pH of the protein slurry is adjusted to a pH of about 6.5 to about 10.0. In a further embodiment, the pH of the protein slurry is adjusted to a pH of about 7.0 to about 9.0.

In another embodiment of the disclosure, the mixture is separated by centrifugation or hydrocyclone to separate the fiber from the mixture and form the protein slurry. In a further embodiment, the mixture is separated by centrifugation to separate the fiber from the mixture and form the protein slurry. In an embodiment, the mixture is centrifuged at a speed of about 1,000 rpm to about 2,000 rpm. In a further embodiment, the mixture is centrifuged at a speed of about 1,400 to about 1,600 rpm. In an embodiment, the mixture is centrifuged using a decanter centrifuge.

In another embodiment of the disclosure, mixing the protein slurry with additional macroalgae and/or microalgae is repeated at least once. In a further embodiment, mixing the protein slurry with additional macroalgae and/or microalgae is repeated at least two to seven times.

In an embodiment of the disclosure, the extraction solvent comprises water, methanol, ethanol, isopropanol, or mixtures thereof. In an embodiment, the extraction solvent comprises ethanol. In another embodiment, the extraction solvent comprises at least about 50% ethanol. In an embodiment, the extraction solvent comprises at least about 70% ethanol. In a further embodiment, the extraction solvent comprises at least about 90% ethanol.

In a further embodiment, the extract is separated from the washed insoluble protein fraction using centrifugation, vacuum filtration, pressure filtration, decantation or gravity draining. In an embodiment, the extract is separated from the washed insoluble protein fraction using centrifugation.

In another embodiment of the disclosure, wherein steps iv) and v) are repeated at least twice.

In a further embodiment, the process further comprises the step of drying the washed insoluble protein fraction to form the protein concentrate. In an embodiment, the protein concentrate is dried in a vacuum dryer, fluidized bed dryer, hot air dryer ring dryer or spray dryer.

In another embodiment, the protein concentrate comprises a hydrolyzed protein concentrate. In another embodiment, the protein concentrate is hydrolyzed to produce peptides and free amino acids. In another embodiment, the hydrolyzed protein concentrate comprises peptides and/or free amino acids.

In an embodiment, the protein concentrate comprises a protein content of about 30% to about 90% on a dry weight basis.

In another embodiment of the disclosure, there is also provided a process for the production of a protein isolate from macroalgae and/or microalgae, comprising:
  i) mixing the macroalgae and/or microalgae with a blending solvent, optionally water or alkaline water, to form a mixture and optionally treating the mixture with phytase at a temperature and a pH suitable for phytase activity;
  ii) optionally adjusting the pH of the mixture to a pH of about 7.0 to about 10.0;
  iii) separating fiber from the mixture to form a first protein slurry, wherein the first protein slurry comprises a soluble protein fraction and an insoluble protein fraction;
  iv) separating the first protein slurry to form a protein solids fraction and a soluble protein fraction;

v) optionally mixing the protein solids fraction with a second blending solvent, optionally water, to form a second protein slurry;

vi) optionally separating the second protein slurry to form a second protein solids fraction and a second soluble protein fraction;

vii) optionally repeating steps v) and vi) at least once;

viii) separating the soluble protein fractions to form a clarified soluble protein fraction and a residual insoluble protein fraction;

ix) optionally adjusting the pH of the clarified soluble protein fraction to a pH of about 6 to about 9;

x) separating the clarified soluble protein fraction, optionally by filtering the clarified soluble protein fraction by membrane filtration; and xi) optionally drying the clarified soluble protein fraction.

In another embodiment of the disclosure, the ratio of macroalgae and/or microalgae to water or alkaline water is about 1:4 to about 1:30 (w/w). In another embodiment, the ratio of macroalgae and/or microalgae to water or alkaline water is about 1:5 to about 1:20 (w/w). In a further embodiment, the ratio is about 1:6 to about 1:12 (w/w). In an embodiment, the ratio is about 1:8 to about 1:10 (w/w).

In an embodiment of the disclosure, the pH of the alkaline water is about 7 to about 12. In another embodiment, the pH of the first protein slurry is adjusted to about 8.0 to about 9.5. In a further embodiment, the pH of the first protein slurry is adjusted to about 8.5 to about 9.0.

In another embodiment of the disclosure, the mixture is separated by centrifugation or hydrocyclone to separate the fiber from the mixture and form the protein slurry. In a further embodiment, the mixture is separated by centrifugation to separate the fiber from the mixture and form the protein slurry. In an embodiment, the mixture is centrifuged at a speed of about 1,000 rpm to about 2,000 rpm. In a further embodiment, the mixture is centrifuged at a speed of about 1,400 to about 1,600 rpm. In an embodiment, the mixture is centrifuged using a decanter centrifuge.

In another embodiment, the first protein slurry is centrifuged, optionally using a disc stack centrifuge, to separate the protein solids fraction from the soluble protein fraction. In a further embodiment, the first protein slurry is centrifuged at a speed of about 4,000 rpm to about 8,000 rpm. In a further embodiment, the first protein slurry is centrifuged at a speed of about 6,500 to about 7,500 rpm.

In another embodiment of the disclosure, the ratio of the protein solids fraction to water is about 1.0:0.5 to about 1.0:3.0 (w/w). In a further embodiment, the ratio of the protein solids fraction to water is about 1.0:1.0 to about 1.0:2.0 (w/w).

In an embodiment, the soluble protein fractions are centrifuged to form the clarified soluble protein fraction and the residual insoluble protein fraction. In an embodiment, the soluble protein fractions are centrifuged using a disc stack centrifuge at a speed of about 7,000 rpm to about 10,000 rpm. In a further embodiment, the soluble protein fractions are centrifuged using a disc stack centrifuge at a speed of about 7,500 rpm to about 8,500 rpm.

In another embodiment of the disclosure, the pH of the clarified soluble protein fraction is adjusted with alkali. In a further embodiment, the pH of the clarified soluble protein fraction is adjusted with sodium hydroxide.

In an embodiment, the clarified soluble protein fraction is filtered using an ultrafiltration apparatus. In a further embodiment, the ultrafiltration apparatus comprises a membrane to filter proteins larger than about 10,000 daltons.

In another embodiment of the disclosure, the process further comprises the step of filtering the clarified soluble protein fraction using a diafiltration apparatus.

In another embodiment, the clarified soluble protein fraction is dried in a vacuum dryer, fluidized bed dryer, ring dryer or spray dryer to form the protein isolate.

In another embodiment, the protein isolate comprises a hydrolyzed protein isolate. In another embodiment, the protein isolate is hydrolyzed to produce peptides and free amino acids. In another embodiment, the hydrolyzed protein isolate comprises peptides and/or free amino acids.

In another embodiment of the disclosure, the protein isolate comprises a protein content of greater than about 90% on a dry weight basis.

In another embodiment of the disclosure, there is also provided a process for the production of a hydrolyzed protein concentrate from macroalgae and/or microalgae, comprising:

i) mixing the macroalgae and/or microalgae with a blending solvent, optionally water, to form a first mixture and optionally treating the mixture with phytase at a temperature and a pH suitable for phytase activity;

ii) optionally adjusting the pH of the first mixture to a pH of about 6.5 to about 10.0;

iii) separating the first mixture to remove fiber from the first mixture and form a protein slurry and an insoluble fiber fraction, wherein the protein slurry comprises a soluble protein fraction and an insoluble protein fraction and the insoluble fiber fraction comprises insoluble fiber and a second insoluble protein fraction;

iv) optionally mixing the insoluble fiber fraction with a second blending solvent, optionally water, to form a washed insoluble fiber fraction and an extract;

v) separating the washed insoluble fiber fraction from the extract;

vi) optionally mixing the washed insoluble fiber fraction with a blending solvent, optionally water, to form a second mixture;

vii) optionally adjusting the pH of the second mixture to a pH suitable for enzymatic activity;

viii) mixing the second mixture with at least one protease to form a hydrolyzed protein extract;

ix) separating the hydrolyzed protein extract from the second mixture to form the hydrolyzed protein concentrate and a second insoluble fiber fraction; and x) optionally drying the hydrolyzed protein concentrate.

In another embodiment of the disclosure, the ratio of macroalgae and/or microalgae to water is about 1:4 to about 1:30 (w/w). In another embodiment, the ratio of macroalgae and/or microalgae to water is about 1:5 to about 1:20 (w/w). In a further embodiment, the ratio is about 1:6 to about 1:12 (w/w). In an embodiment, the ratio is about 1:8 to about 1:10 (w/w).

In another embodiment, the pH of the first mixture is adjusted to about 8.0 to about 9.5. In a further embodiment, the pH of the first mixture is adjusted to about 8.5 to about 9.0.

In another embodiment of the disclosure, the first mixture is separated by centrifugation or hydrocyclone to separate the fiber from the first mixture and form the protein slurry. In a further embodiment, the mixture is separated by centrifugation to separate the fiber from the mixture and form the protein slurry. In an embodiment, the first mixture is centrifuged at a speed of about 1,000 rpm to about 2,000 rpm. In a further embodiment, the first mixture is centrifuged at a speed of about 1,400 to about 1,600 rpm. In an embodiment, the mixture is centrifuged using a decanter centrifuge.

In another embodiment, the ratio of the insoluble fiber fraction or washed insoluble fiber fraction to water is about 1.0:0.5 to about 1.0:3.0 (w/w). In a further embodiment, the ratio of the insoluble fiber fraction or washed insoluble fiber fraction to water is about 1.0:1.0 to about 1.0:2.0 (w/w).

In another embodiment, the washed insoluble fiber fraction is centrifuged to separate the washed insoluble fiber fraction from extract. In a further embodiment, the washed insoluble fiber fraction is centrifuged at a speed of about 2,000 rpm to about 6,000 rpm. In a further embodiment, washed insoluble fiber fraction is centrifuged at a speed of about 3,000 to about 5,500 rpm.

In another embodiment of the disclosure, the pH of the second mixture is adjusted to about 8.0 to about 9.0.

In an embodiment of the disclosure, the ratio of the second mixture to the protease is about 100:1 to about 5000:1 (w/w).

In an embodiment of the disclosure, the second mixture is mixed with a protease at a temperature of about 40° C. to about 60° C. In another embodiment, the second mixture is mixed with a protease at a temperature of about 45° C. to about 55° C.

In another embodiment, the at least one protease comprises a protease from *Bacillus Licheniformis*.

In a further embodiment, the process further comprises the step of mixing the second mixture with a second protease.

In an embodiment, the ratio of the second mixture to the second protease is about 250:1 to about 5000:1 (w/w).

In another embodiment, the second mixture is mixed with the second protease at a temperature of about 50° C. to about 70° C. In an embodiment, the second mixture is mixed with the second protease at a temperature of about 55° C. to about 65° C.

In a further embodiment, the second protease comprises a fungal protease/peptidase complex from *Aspergillus oryzae*.

In another embodiment, the hydrolyzed protein concentrate is dried in a vacuum dryer, fluidized bed dryer, ring dryer or spray dryer to form the protein isolate.

In a further embodiment, the hydrolyzed protein concentrate comprises a protein content of about 30% to about 90% on a dry weight basis.

In another embodiment, the process further comprises mixing the hydrolyzed protein extract with water to form a third mixture. In a further embodiment, the process further comprises filtering the third mixture fraction and the filtering comprises ultrafiltration. In an embodiment, the ultrafiltration comprises contacting the third mixture with an ultrafiltration apparatus that comprises a membrane to filter proteins larger than about 1,000 daltons.

In another embodiment, the process further comprises mixing the second insoluble fiber fraction to form a washed hydrolyzed protein extract and a washed second insoluble fiber fraction and separating the form the washed hydrolyzed protein extract from the washed second insoluble fiber fraction. In another embodiment, the washed hydrolyzed protein extract is combined with the hydrolyzed protein extract.

In an embodiment of the disclosure, there is also provided a process for the production of a protein concentrate from macroalgae and/or microalgae comprising:

i) mixing the macroalgae and/or microalgae with a blending solvent, optionally water, a saline solution or a polysaccharide solution, to form a mixture and optionally treating the mixture with phytase at a temperature and a pH suitable for phytase activity;

ii) optionally adjusting the pH of the mixture to a pH of about 2.0 to about 10.0;

iii) separating fiber from the mixture to form a protein slurry, wherein the protein slurry comprises a first soluble protein fraction and an insoluble protein fraction;

iv) optionally repeating steps i)-iii) by mixing the protein slurry with additional algae;

v) separating the soluble protein fraction from the insoluble protein fraction;

vi) washing the insoluble protein fraction with a second blending solvent, optionally water, saline solution or polysaccharide solution, to form a washed insoluble protein fraction and a second soluble protein fraction;

vii) separating the washed insoluble protein fraction and the second soluble protein fraction;

viii) combining and separating the first and second soluble protein fractions to form a protein concentrate, optionally by filtering the first and second soluble protein fractions to form a protein concentrate or isolate;

ix) combining the washed insoluble protein fraction with the protein concentrate to form a combined protein concentrate or isolate; and x) optionally drying the combined protein concentrate.

In another embodiment of the disclosure, the ratio of macroalgae and/or microalgae to water is about 1:3 to about 1:30 (w/w). In another embodiment, the ratio of macroalgae and/or microalgae to water is about 1:5 to about 1:20 (w/w). In a further embodiment, the ratio is about 1:6 to about 1:12 (w/w). In an embodiment, the ratio is about 1:8 to about 1:10 (w/w).

In an embodiment, the pH of the mixture is adjusted to a pH of about 6.5 to about 10.0. In another embodiment, the pH of the mixture is adjusted to a pH of about 7.0 to about 9.0.

In another embodiment of the disclosure, the mixture is separated by centrifugation or hydrocyclone to separate the fiber from the mixture and form the protein slurry. In a further embodiment, the mixture is separated by centrifugation to separate the fiber from the mixture and form the protein slurry. In an embodiment, the mixture is centrifuged at a speed of about 1,000 rpm to about 2,000 rpm. In a further embodiment, the mixture is centrifuged at a speed of about 1,400 to about 1,600 rpm. In an embodiment, the mixture is centrifuged using a decanter centrifuge.

In another embodiment, the protein slurry is centrifuged to separate the protein solids fraction from the soluble protein fraction. In an embodiment, the protein slurry is centrifuged at a speed of about 6,000 rpm to about 8,500 rpm in a disc stack centrifuge. In another embodiment, the protein slurry is centrifuged at a speed of about 6,500 to about 7,500 rpm.

In another embodiment, the ratio of the insoluble protein fraction to water is about 1.0:0.5 to about 1.0:3.0 (w/w). In a further embodiment, the ratio of the insoluble protein fraction to water is about 1.0:1.0 to about 1.0:2.0 (w/w).

In another embodiment, the washed insoluble protein fraction and the second soluble protein fraction are separated using a centrifuge. In an embodiment, the washed insoluble protein fraction and the second soluble protein fraction are centrifuged at a speed of about 6,000 rpm to about 8,500 rpm in a disc stack centrifuge. In a further embodiment, the washed insoluble protein fraction and the second soluble protein fraction are centrifuged at a speed of about 6,500 to about 7,500 rpm.

In another embodiment, the first and second soluble protein fractions are filtered using an ultrafiltration apparatus. In a further embodiment, the ultrafiltration apparatus comprises a membrane to filter proteins larger than about 10,000 daltons. In an embodiment, the process further comprises the step of filtering the first and second soluble protein fractions using a diafiltration apparatus.

In another embodiment, the combined protein concentrate is dried in a vacuum dryer, fluidized bed dryer, ring dryer or spray dryer to form the dried protein concentrate.

In another embodiment, the protein concentrate comprises a hydrolyzed protein concentrate. In another embodiment, the protein concentrate is hydrolyzed to produce peptides and free amino acids. In another embodiment, the hydrolyzed protein concentrate comprises peptides and/or free amino acids.

In a further embodiment, the protein concentrate comprises a protein content of about 50% to about 90% on a dry weight basis.

In an embodiment of the disclosure, there is also provided a process for the production of a protein isolate from macroalgae and/or microalgae comprising:
i) mixing the macroalgae and/or microalgae with a blending solvent, optionally water, to form a mixture and optionally treating the mixture with phytase at a temperature and a pH suitable for phytase activity;
ii) optionally adjusting the pH of the mixture to a pH of about 2.0 to about 10.0;
iii) separating fiber from the mixture to form a protein slurry, wherein the protein slurry comprises a soluble protein fraction and an insoluble protein fraction;
iv) washing the fiber with a second blending solvent, optionally water, to form a washed fiber fraction;
vi) separating the washed fiber fraction to form a second protein slurry and washed fiber solids;
vii) combining and separating the first and second protein slurries to form a protein concentrate, optionally by filtering the first and second soluble protein fractions to form a protein concentrate; and
ix) optionally drying the protein concentrate.

In another embodiment of the disclosure, the ratio of macroalgae and/or microalgae to water is about 1:3 to about 1:30 (w/w). In another embodiment, the ratio of macroalgae and/or microalgae to water is about 1:5 to about 1:20 (w/w). In a further embodiment, the ratio is about 1:6 to about 1:12 (w/w). In an embodiment, the ratio is about 1:8 to about 1:10 (w/w).

In an embodiment, the pH of the mixture is adjusted to a pH of about 6.5 to about 10.0. In another embodiment, the pH of the mixture is adjusted to a pH of about 7.0 to about 9.0.

In another embodiment of the disclosure, the mixture is separated by centrifugation or hydrocyclone to separate the fiber from the mixture and form the protein slurry. In a further embodiment, the mixture is separated by centrifugation to separate the fiber from the mixture and form the protein slurry. In an embodiment, the mixture is centrifuged at a speed of about 1,000 rpm to about 2,000 rpm. In a further embodiment, the mixture is centrifuged at a speed of about 1,400 to about 1,600 rpm. In an embodiment, the mixture is centrifuged using a decanter centrifuge.

In another embodiment, the ratio of the fiber fraction to water is about 1.0:0.5 to about 1.0:3.0 (w/w). In a further embodiment, the ratio of the insoluble protein fraction to water is about 1.0:1.0 to about 1.0:2.0 (w/w).

In another embodiment of the disclosure, the washed fiber fraction is separated by centrifugation or hydrocyclone to separate the fiber solids and form second the protein slurry. In a further embodiment, the washed fiber fraction is separated by centrifugation to separate the fiber and form the second protein slurry. In an embodiment, the mixture is centrifuged at a speed of about 1,000 rpm to about 2,000 rpm. In a further embodiment, the fiber fraction is centrifuged at a speed of about 1,400 to about 1,600 rpm. In an embodiment, the fiber fraction is centrifuged using a decanter centrifuge.

In another embodiment, the first and second slurries are filtered using an ultrafiltration/microfiltration apparatus. In a further embodiment, the ultrafiltration/microfiltration apparatus comprises a membrane to filter proteins larger than about 10,000 daltons. In an embodiment, the process further comprises the step of filtering the first and second slurries using a diafiltration apparatus.

In another embodiment, the protein concentrate is dried in a vacuum dryer, fluidized bed dryer, ring dryer or spray dryer to form the dried protein concentrate.

In another embodiment, the protein isolate comprises a hydrolyzed protein isolate. In another embodiment, the protein isolate is hydrolyzed to produce peptides and free amino acids. In another embodiment, the hydrolyzed protein isolate comprises peptides and/or free amino acids.

In a further embodiment, the protein concentrate comprises a protein content of about 30% to about 90% on a dry weight basis.

In another embodiment of the disclosure, there is also provided a process for the removal of fiber from a partially defatted, fully defatted or protein-enriched algae, comprising:
i) mixing macroalgae and/or microalgae with a blending solvent, optionally water, an aqueous solution or protein containing solution, to form a mixture and optionally treating the mixture with phytase at a temperature and a pH suitable for phytase activity;
ii) optionally adjusting the pH of the protein slurry to a pH of about 2 to about 10; and
iii) separating the mixture to form a protein slurry comprising soluble and insoluble proteins and an insoluble fiber fraction.

The present disclosure relates to processes for the production of protein concentrates and protein isolates, in addition to hydrolyzed protein concentrates and isolates, in which the macroalgae and/or microalgae is subjected to low g-forces to separate the fiber from the insoluble and soluble protein fractions.

Accordingly, the present disclosure includes a process for the production of a protein concentrate from macroalgae and/or microalgae comprising:
i) mixing the macroalgae and/or microalgae with a first blending solvent to form a mixture;
ii) optionally treating the mixture with phytase at a temperature and a pH suitable for phytase activity;
iii) optionally adjusting the pH of the mixture to a pH between 6.0 and 10.0;
iv) subjecting the mixture to a g-force sufficient to separate the mixture to form
  a) a fiber fraction, and
  b) protein fractions comprising an insoluble protein fraction and a soluble protein fraction;
v) optionally mixing the fiber fraction with a second blending solvent and repeating step iv);
vi) optionally adjusting the pH of the protein fractions to a pH between 4.0 and 6.0;
vii) optionally heating the protein fractions to a temperature between 80° C. and 100° C. to precipitate the proteins; and
viii) separating the precipitated proteins from the protein fraction to form the protein concentrate.

In another embodiment, the first and second blending solvents comprise water, a saline solution or a polysaccharide solution. In a further embodiment, the first and second blending solvents comprise water.

In an embodiment of the disclosure, the ratio of the macroalgae and/or microalgae to the first blending solvent is 1:3 to 1:30 (w/w) of algae to solvent, optionally about 1:8 to about 1:10 (w/w).

In an embodiment of the disclosure, the phytase is added in an amount between 0.01% and 0.1% (w/w) based on the weight of the macroalgae and/or microalgae. In a further embodiment, the temperature suitable for phytase activity is between 20° and 60° C. In a further embodiment, the pH suitable for phytase activity is between 2.0 and 7.0.

In another embodiment of the disclosure, the mixture is subjected to a g-force of between 100 g and 500 g, optionally between 150 g and 400 g, suitably between 180 g and 350 g.

In another embodiment, separating the mixture comprises using a centrifuge or a hydrocyclone. In another embodiment, the centrifuge comprises a decanter centrifuge or disc stack centrifuge.

In a further embodiment, separating the precipitated proteins comprises using a centrifuge or a hydrocyclone. In another embodiment, separating the precipitated proteins comprises using a centrifuge. In another embodiment, centrifuging the precipitated proteins comprises a g-force between 2,500 g and 9,500 g.

In another embodiment of the disclosure, the process further comprises the step of drying the protein concentrate to a moisture content of between 4% and 8% (w/w).

In another embodiment, the protein concentrate comprises a hydrolyzed protein concentrate. In another embodiment, the hydrolyzed protein concentrate comprises peptides and/or free amino acids.

The present disclosure also includes a process for the production of a protein concentrate from macroalgae and/or microalgae comprising:

i) mixing the macroalgae and/or microalgae with a first blending solvent to form a mixture;
  ii) optionally treating the mixture with phytase at a temperature and a pH suitable for phytase activity;
  iii) optionally adjusting the pH of the mixture to a pH between 6.0 and 10.0;
  iv) subjecting the mixture to a g-force sufficient to separate the mixture to form
    a) a fiber fraction, and
    b) protein fractions comprising an insoluble protein fraction and a soluble protein fraction;
  v) optionally mixing the fiber fraction with a second blending solvent and repeating step iv);
  vi) optionally adjusting the pH of the protein fractions to a pH between 4.0 and 6.0;
  vii) mixing the protein fractions with a mixing solvent to form a protein slurry and precipitate the proteins;
  viii) separating the precipitated proteins from the protein slurry to form the protein concentrate; and
  viii) optionally repeating steps vi) and vii) with the precipitated proteins.

In another embodiment, the first and second blending solvents comprise water, a saline solution or a polysaccharide solution. In a further embodiment, the first and second blending solvents comprise water.

In an embodiment of the disclosure, the ratio of the macroalgae and/or microalgae to the first blending solvent is 1:3 to 1:30 (w/w) of algae to solvent, optionally about 1:8 to about 1:10 (w/w).

In an embodiment of the disclosure, the phytase is added in an amount between 0.01% and 0.1% (w/w) based on the weight of the macroalgae and/or microalgae. In a further embodiment, the temperature suitable for phytase activity is between 20° and 60° C. In a further embodiment, the pH suitable for phytase activity is between 2.0 and 7.0.

In another embodiment of the disclosure, the mixture is subjected to a g-force of between 100 g and 500 g, suitably between 150 g and 400 g, optionally between 180 g and 350 g.

In another embodiment, separating the mixture comprises using a centrifuge or a hydrocyclone. In another embodiment, the centrifuge comprises a decanter centrifuge or a disc stack centrifuge.

In another embodiment of the disclosure, the mixing solvent comprises an ethanol:water mixture, wherein the ethanol is present in an amount between 90% and 100% (v/v).

In another embodiment, separating the precipitated proteins comprises using a centrifuge or a hydrocyclone. In another embodiment, separating the precipitated proteins comprises using a centrifuge. In another embodiment, centrifuging the precipitated proteins comprises a g-force between 2,500 g and 9,500 g.

In another embodiment of the disclosure, steps vii) and viii) are repeated at least twice.

In another embodiment, the process further comprises the step of drying the protein concentrate to a moisture content of between 4% and 8% (w/w). In another embodiment, the protein concentrate comprises a hydrolyzed protein concentrate. In a further embodiment, the hydrolyzed protein concentrate comprises peptides and/or free amino acids.

The present disclosure also includes a process for the production of a protein isolate from macroalgae and/or microalgae comprising:

i) mixing the macroalgae and/or microalgae with a first blending solvent to form a mixture;
  ii) optionally treating the mixture with phytase at a temperature and a pH suitable for phytase activity;
  iii) optionally adjusting the pH of the mixture to a pH between 6.0 and 10.0;
  iv) subjecting the mixture to a g-force sufficient to separate the mixture to form
    a) a fiber fraction, and
    b) protein fractions comprising an insoluble protein fraction and a soluble protein fraction;
  v) optionally mixing the fiber fraction with a second blending solvent and repeating step iv);
  vi) separating the insoluble protein fraction from the soluble protein fraction to recover therefrom an insoluble protein concentrate and a soluble protein extract; and
  vii) subjecting the soluble protein extract to filtration to recover therefrom the protein isolate.

In another embodiment, the first and second blending solvents comprise water, a saline solution or a polysaccharide solution. In a further embodiment, the first and second blending solvents comprise water.

In an embodiment of the disclosure, the ratio of the macroalgae and/or microalgae to the first blending solvent is 1:3 to 1:30 (w/w) of algae to water, optionally about 1:8 to about 1:10 (w/w).

In an embodiment of the disclosure, the phytase is added in an amount between 0.01% to 0.1% (w/w) based on the weight of the macroalgae and/or microalgae. In a further embodiment, the temperature suitable for phytase activity is between 20° and 60° C. In a further embodiment, the pH suitable for phytase activity is between 2.0 and 7.0.

In another embodiment of the disclosure, the mixture is subjected to a g-force of between 100 g and 500 g, suitably between 150 g and 400 g, optionally between 180 g and 350 g.

In another embodiment, separating the mixture comprises using a centrifuge or a hydrocyclone. In an embodiment, the centrifuge comprises a decanter centrifuge or a disc stack centrifuge.

In another embodiment, separating the insoluble protein fraction from the soluble protein fraction comprises using a centrifuge or a hydrocyclone. In a further embodiment separating the insoluble protein fraction from the soluble protein fraction comprises using a centrifuge. In another embodiment, centrifuging to separate the insoluble protein fraction from the soluble protein fraction comprises a g-force between 2,500 g and 9,500 g.

In another embodiment, the process further comprises the step of drying the protein isolate to a moisture content of between 4% and 8% (w/w).

In a further embodiment, the protein isolate comprises a hydrolyzed protein concentrate. In another embodiment, the hydrolyzed protein concentrate comprises peptides and/or free amino acids.

In another embodiment of the disclosure, there is also provided a process for the production of a protein concentrate from macroalgae and/or microalgae comprising:
  i) mixing the macroalgae and/or microalgae with a first blending solvent to form a mixture;
  ii) optionally treating the mixture with phytase at a temperature and a pH suitable for phytase activity;
  iii) optionally adjusting the pH of the mixture to solubilize proteins in the mixture;
  iv) subjecting the mixture to a g-force sufficient to separate the mixture to form
    a) a fiber fraction, and
    b) a protein fraction comprising
      (i) an insoluble protein fraction, and
      (ii) a soluble protein fraction;
  v) separating the fiber fraction from the protein fraction and mixing the fiber fraction with a second blending solvent to form a fiber mixture;
  vi) treating the fiber mixture with a protease at a temperature and a pH suitable for protease activity;
  vii) subjecting the fiber mixture to a g-force sufficient to separate the fiber mixture to form:
    a) a second fiber fraction, and
    b) a hydrolyzed protein fraction, comprising
      (i) an insoluble protein fraction comprising partially hydrolyzed and un-hydrolyzed protein, and
      (ii) a soluble hydrolyzed protein fraction;
  viii) optionally adjusting the pH of the protein fraction from step iv(b) to a pH suitable to precipitate proteins;
  ix) separating the precipitated proteins from the protein fraction;
  x) optionally combining the precipitated proteins and the hydrolyzed protein fraction to form the protein concentrate.

In another embodiment, the process further comprises mixing the fiber fraction with the first blending solvent and repeating step iv) once, twice or three times and/or mixing the second fiber fraction with the second blending solvent and repeating step vii) once, twice or three times.

In another embodiment, the first and second blending solvents comprise water, a saline solution or a polysaccharide solution, optionally water, and wherein the ratio of the macroalgae and/or microalgae to the first blending solvent is 1:3 to 1:30 (w/w) of algae to water.

In another embodiment, the temperature suitable for phytase activity is between 20° and 60° C. and the pH suitable for phytase activity is between 2.0 and 7.0 and the temperature suitable for protease activity is between 30° and 70° C. and the pH suitable for protease activity is between 5.0 and 9.0.

In another embodiment, the mixture and/or the fiber mixture is subjected to a g-force of between 100 g and 500 g, optionally between 150 g and 400 g, or between 170 g and 350 g. In an embodiment, separating the mixture and/or the fiber mixture comprises using a centrifuge or a hydrocyclone.

In a further embodiment, the pH suitable to precipitate the proteins in the protein fraction is between 4.0 and 6.0.

In another embodiment, the process further comprises the step of drying the protein concentrate to a moisture of between 4% and 8% (w/w). In another embodiment, the protein concentrate also comprises peptides and free amino acids.

The present disclosure also includes a process for the production of a protein concentrate from macroalgae and/or microalgae comprising:
  i) mixing the macroalgae and/or microalgae with a first blending solvent to form a mixture;
  ii) optionally treating the mixture with phytase at a temperature and a pH suitable for phytase activity;
  iii) optionally adjusting the pH of the mixture to solubilize proteins in the mixture;
  iv) subjecting the mixture to a g-force sufficient to separate the mixture to form
    a) a fiber fraction, and
    b) a protein fraction comprising
      (i) an insoluble protein fraction, and
      (ii) a soluble protein fraction;
  v) separating the fiber fraction from the protein fraction and mixing the fiber fraction with a second blending solvent to form a fiber mixture;
  vi) treating the fiber mixture with a protease at a temperature and a pH suitable for protease activity;
  vii) subjecting the fiber mixture to a g-force sufficient to separate the fiber mixture to form:
    a) a second fiber fraction, and
    b) a hydrolyzed protein fraction, comprising
      (i) an insoluble protein fraction comprising partially hydrolyzed and un-hydrolyzed protein, and
      (ii) a soluble hydrolyzed protein fraction;
  viii) mixing the protein fraction with a mixing solvent to precipitate proteins;
  ix) separating the precipitated proteins from the protein fraction; and
  x) optionally combining the precipitated proteins and the hydrolyzed protein fraction to form the protein concentrate.

In another embodiment, the process further comprises mixing the fiber fraction with the first blending solvent and repeating step iv) once, twice or three times and/or mixing the second fiber fraction with the second blending solvent and repeating step vii) once, twice or three times.

In another embodiment, the first and second blending solvents comprise water, a saline solution or a polysaccharide solution, optionally water, and wherein the ratio of the macroalgae and/or microalgae to the first blending solvent is 1:3 to 1:30 (w/w) of algae to water.

In another embodiment, the temperature suitable for phytase activity is between 20° and 60° C. and the pH suitable for phytase activity is between 2.0 and 7.0 and the temperature suitable for protease activity is between 30° and 70° C. and the pH suitable for protease activity is between 5.0 and 9.0.

In another embodiment, the mixture and/or the fiber mixture is subjected to a g-force of between 100 g and 500 g, optionally between 150 g and 400 g, or between 170 g and 350 g. In an embodiment, separating the mixture and/or the fiber mixture comprises using a centrifuge or a hydrocyclone.

In another embodiment, the mixing solvent comprises an ethanol:water mixture, wherein the ethanol is present in an amount between 80% and 100% (v/v).

In another embodiment, the process further comprises the step of drying the protein concentrate to a moisture of between 4% and 8% (w/w). In another embodiment, the protein concentrate also comprises peptides and free amino acids.

In another embodiment, the present disclosure also includes a process for the production of a protein isolate from macroalgae and/or microalgae comprising:
i) mixing the macroalgae and/or microalgae with a first blending solvent to form a mixture;
ii) optionally treating the mixture with phytase at a temperature and a pH suitable for phytase activity;
iii) optionally adjusting the pH of the mixture to solubilize proteins in the mixture;
iv) subjecting the mixture to a g-force sufficient to separate the mixture to form
   a) a fiber fraction, and
   b) a protein fraction comprising
     (i) an insoluble protein fraction, and
     (ii) a soluble protein fraction;
vi) separating the insoluble protein fraction from the soluble protein fraction to recover therefrom an insoluble protein concentrate and a soluble protein extract; and
vii) subjecting the soluble protein extract to membrane filtration to recover therefrom the protein isolate.

In another embodiment, the process further comprises mixing the fiber fraction with the first blending solvent and repeating step iv) once, twice or three times.

In another embodiment, the first and second blending solvents comprise water, a saline solution or a polysaccharide solution, optionally water, and wherein the ratio of the macroalgae and/or microalgae to the first blending solvent is 1:3 to 1:30 (w/w) of algae to water.

In another embodiment, the temperature suitable for phytase activity is between 20° and 60° C. and the pH suitable for phytase activity is between 2.0 and 7.0 and the temperature suitable for protease activity is between 30° and 70° C. and the pH suitable for protease activity is between 5.0 and 9.0.

In another embodiment, the mixture and/or the fiber mixture is subjected to a g-force of between 100 g and 500 g, optionally between 150 g and 400 g, or between 170 g and 350 g. In an embodiment, separating the mixture and/or the fiber mixture comprises using a centrifuge or a hydrocyclone.

In another embodiment, the process further comprises the step of drying the protein concentrate to a moisture of between 4% and 8% (w/w). In another embodiment, the protein concentrate also comprises peptides and free amino acids.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

Embodiments of the invention will be described in relation to the drawings in which.

Figure 1:
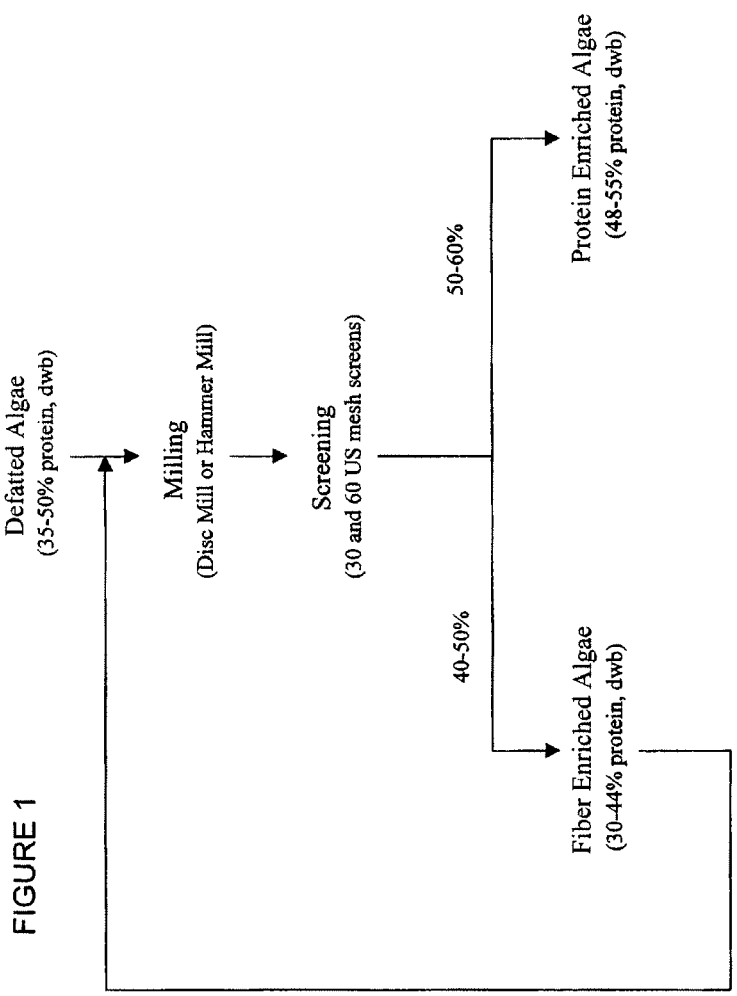
FIG. 1 is a schematic representation showing a preparation of a protein-enriched algae from a defatted algae.

DETAILED DESCRIPTION OF THE DISCLOSURE (I) Definitions

The term "peptide" as used herein refers to various natural compounds containing two or more amino acids linked by the carboxylic acid group of one amino acid to the amino group of another amino acid. Peptides generally have 4-100 amino acids (US Patent Office Classification Index Glossary) and a molecular weight of less than about 10,000 Daltons.

The term "protein" as used herein refers to peptides with more than about 50-100 amino acids and a molecular weight in excess of about 10,000 Daltons. The US Patent Office Classification Index Glossary defines protein as peptides with more then 100 amino acids.

The term "partially defatted macroalgae and/or microalgae" or "totally defatted macroalgae and/or microalgae" as used herein refers to algae which has been treated to remove some, or all, of the oil contained within. In an embodiment, to remove oil from macroalgae and/or microalgae, the algae are dried. Dried macroalgae and/or microalgae are mixed with solvent, such as hexane or methyl pentane, at a ratio of 1 to 3 to 1 to 10 by weight. The algae solvent slurry is milled (such as with a bead mill) to break the cell walls of the algae. This is followed by centrifugation to separate the oil in the solvent from the solids. The solvent extract is desolventized and dried to produce crude algae oil. The solids are desolventized and dried to produce defatted (partially or totally) macroalgae and/or microalgae, which can be used in the processes of the present disclosure. In another embodiment, wet macroalgae and/or microalgae are wet milled, and optionally enzymatic hydrolysis using cellulase, to break the cell walls. This is followed by centrifugation to separate oil layer from aqueous layer. The oil layer is processed into oil. The aqueous layer is used as starting material for the processes of the present disclosure. Depending on the identity of the macroalgae and/or microalgae, the oil content may be minimal, such that it is not necessary to perform an oil extraction step.

The term "protein-enriched macroalgae and/or microalgae" as used herein refers to a defatted (partially or totally) macroalgae and/or microalgae as described above, which has subsequently been treated to remove fiber. Accordingly, the macroalgae and/or microalgae is typically subjected to a milling step and a screening step to remove fiber and obtain algae having a higher protein content than the algae initially contained, on a dry weight basis, and about 5% to about 6.5% fiber, optionally less than about 6%. Collectively, the terms "algae" and "macroalgae and/or microalgae" may be used to refer to a defatted (partially or totally) algae starting material, as well as a protein-enriched material.

The term "macroalgae and/or microalgae" (collectively known as "algae") as used herein refers any aquatic photosynthetic organism, ranging from single cell organisms, to large aquatic plants such as kelp. Microalgae refers to (but not limited to) single-cell or groups of cells joined together from the Kingdom Protista and refers to all photosynthetic protists, such as phytoplankton, cyanobacteria, diatoms, dinoflagellates, etc. Macroalgae refers to for example, aquatic plants (having roots, stems and leaves) such as seaweed, chlorophyta, rhodophyta, phaeophya (kelps), etc. Different species of macroalgae and/or microalgae contain different amounts of protein initially in their cell structure, optionally greater than 10% (w/w), or 15% (w/w), or 20% (w/w), 40% (w/w), 50% (w/w) or 60% (w/w) or more. The macroalgae and/or microalgae that is useful to produce a protein concentrate or isolate using the processes of the present disclosure, are those species in which a protein concentrate having at least 30% (w/w) is produced.

The term "protein concentrate" as used herein refers to macroalgae and/or microalgae that has been treated to isolate protein using the processes of the present disclosure to increase the protein content, where the protein concentrate has greater than 30% protein content, optionally greater than 50%, optionally greater than 60% but less than 90% protein content on a dry weight basis. The balance may comprise carbohydrate, ash, fiber and oil. In an embodiment, the protein concentrate is generally produced from the insoluble protein fraction or soluble/insoluble protein fractions of a protein mixture. In one embodiment, the protein concentrate also includes hydrolyzed protein concentrate.

The term "hydrolyzed protein concentrate" as used herein refers to a protein concentrate that has been treated to hydrolyze the proteins within the protein concentrate into amino acids and smaller peptides. Proteins can be hydrolyzed using various chemicals, such as strong acids and bases, and enzymes, preferably proteases.

The term "protein isolate" as used herein refers to macroalgae and/or microalgae that has been treated to isolate protein using the processes of the present disclosure to increase the protein content, where the protein isolate has 90% or greater than 90% protein on a dry weight basis. The balance may comprise carbohydrate, ash, and oil. In an embodiment, the protein isolate is generally produced from the soluble protein fraction of a protein mixture.

The term "hydrolyzed protein isolate" as used herein refers to a protein isolate that has been treated with proteases to hydrolyze the proteins within the protein isolate into amino acids and smaller peptides.

The term "protease" as used herein refers to any enzyme that hydrolyzes proteins by hydrolysis of the peptide bonds that link amino acids together in the polypeptide chain forming the protein. Examples of proteases include, but are not limited to, Alcalase®, Flavourzyme® and Protamex®. The proteases solubilize and partially hydrolyse proteins trapped within the fiber fraction and to release insoluble proteins from the fiber fraction using a dosage of a single protease.

The term "mixing solvent" as used herein refers to a solvent that forms a protein slurry or mixture when mixed with macroalgae and/or microalgae. In addition, the fiber present in the algae possesses minimal solubility in the mixing solvent (eg. typically less than 1% (w/w) solubility, or about 0% solubility), and suitably, is not soluble in the mixing solvent. Examples of mixing solvents include, but are not limited to, water, alcohols, such as methanol, ethanol or isopropanol, polysaccharide solutions such as guar gum solution, saline solutions, or mixtures of any of the above.

The term "blending solvent" as used herein refers to any aqueous solvent (typically at least: 80%, 85%, 90%, 95%, 98% or 99% water by weight) that forms a slurry or mixture when mixed with macroalgae and/or microalgae. Typically the blending solvent is free from organic solvents, such as methanol, ethanol, propanol, iso-propanol, tetrahydrofuran since these solvents are not desirable as residues in a protein isolate, concentrate or hydrosylate for human consumption, however, if organic solvents are present, they are in the blending solvent in small amount (eg. typically equal to or less than: 20%, 10%, 10%, 5% or 1%) so that their presence in the final product is negligible. Examples of blending solvents include water, acidic water, alkaline water, saline salt solutions (such as sodium chloride, potassium chloride, calcium chloride), polysaccharide solutions (such as guar gum), and aqueous protein solutions.

The disclosure contemplates using a variety of solvents, which could include blending solvents, mixing solvents or other combinations or alcohols (eg. 80% ethanol), water and/or aqueous solvents. The use of the term blending solvents should not be construed as precluding the use of organic solvents in processes as disclosed herein.

The term "extraction solvent" as used herein refers to a solvent which is capable of solubilizing antinutritional compounds, or other constituents, that are present in the algae and which are desirably removed. Examples of antinutritionals include, but are not limited to, glucosinolates, phytic acid, phytates and other compounds that reduce the nutritional or commercial value of the protein concentrate or protein isolate. Antinutritional compounds are compounds that are, for example, not digestible by mammals (e.g humans), have adverse effects, such as toxicity or are bitter tasting, and are desirably removed from the protein product. Accordingly, the concentration of antinutritionals in a protein product produced in accordance with a process of the present disclosure is less than about 1% (w/w), optionally less than about 0.5% (w/w), optionally less than about 0.1% (w/w), and optionally less than about 0.05% (w/w). Examples of other compounds include, but are not limited to, materials that undesirably effect the quality, color, taste, odor, appearance or characteristics of the end product. Examples include compounds that cause a darkening or variation in the color, cause a bitter taste or a pungent odor, such as sinapine or sinigrin, or affect the handling or agglomeration of the end product. While the antinutritionals or other components are not desirable in the protein concentrates or isolates they may constitute commercially valuable side products which can have utility as medicinal or industrial ingredients or end products once separated from the protein concentrate or isolate. Examples of extraction solvents include, but are not limited to, water, alcohols, such as methanol, ethanol, isopropanol, or mixtures of any of the above. Other extractions solvents which are useful include tetrahydrofuran (THF), dimethylformamide (DMF), and ethers, such as methyl t-butyl ether. However, it will be known to those skilled in the art that solvents such as THF, DMF or ethers, as a result of their higher toxicity as compared to, for example, ethanol, require lower limits in the protein product. macroalgae and/or microalgae The term "homogeneous agitation" as used herein refers to the mixing of macroalgae and/or microalgae with a solvent to form a homogenous mixture or suspension. Such agitation is accomplished, for example, by mixing the slurry or mixture at a speed of about 30 rpm to about 300 rpm in a standard mixer.

The term "washed" used herein refers to a protein fraction that has been mixed with an extraction solvent, such as ethanol, to remove antinutritional compounds, or other constituents, from the protein fraction.

The term "protein slurry" as used herein refers to protein, for example, the protein in macroalgae and/or microalgae, that has been mixed with a mixing solvent to form a suspension of protein, and optionally fiber and other antinutritional compounds, in the mixing solvent.

The terms "soluble protein fraction" and "insoluble protein fraction" as used herein refer to specific protein fractions which are either soluble or insoluble, respectively, in a particular solvent, such as a blending solvent, mixing solvent or an extraction solvent. In an embodiment, the insoluble protein fraction is generally composed of insoluble globulin and denatured proteins. The insoluble protein fraction is generally composed of insoluble globulin proteins. In another embodiment, the soluble protein fraction is generally composed of albumin, soluble globulin and undenatured proteins. The soluble protein fraction is generally composed of soluble albumin and soluble globulin proteins.

The term "water" as used herein refers to any source of water, for example, tap water, distilled water or reverse osmosis water.

The term "alkaline water" as used herein refers to water which has a basic pH of greater than about 7.0, optionally about 7.0 to about 12.0. The alkalinity of the water results from the addition of a base to water, for example, an alkali hydroxide such as sodium hydroxide. For example, a solution of sodium hydroxide at a concentration of about 5% to about 15% (w/w), optionally 11%.

The term "suitable for phytase activity" as used herein refers to the conditions, such as the temperature and pH, and optionally includes the length of time, in which the phytase enzyme is able to hydrolyze the phosphate groups on phytate or phytic acid, and accordingly, reduce the amount of phytates or phytic acid in the mixture. In an embodiment, the temperature suitable for phytase activity is between 20° C. and 60° C., optionally between 40° C. and 55° C., suitably between 50° C. and 55° C. In another embodiment, the pH suitable for phytase activity is between 2.0 and 7.0, optionally between 4.0 and 6.0, suitably between 4.5 and 5.5, optionally 5.0 to 5.5. In another embodiment, the concentration of the phytase enzyme is between 0.01% to 1.0% (w/w) based on the weight of the macroalgae and/or microalgae, optionally 0.01% and 0.5% optionally 0.01% and 0.1%. It will be understood that the conditions suitable for phytase activity apply to all of the processes of the present disclosure.

The term "suitable for protease activity" as used herein refers to the conditions, such as the temperature and pH, and optionally includes the length of time, in which a protease enzyme is able to hydrolyze proteins. In an embodiment, the temperature suitable for protease activity is between 30° C. and 70° C., optionally between 35° C. and 70° C. In another embodiment, the pH suitable for protease activity is between 5.0 and 9.0, optionally between 5.5 and 8.5. In another embodiment, the concentration of the protease enzyme is between 0.01% to 1.0% (w/w) based on the weight of the macroalgae and/or microalgae, optionally 0.01% and 0.5% optionally 0.01% and 0.1%. It will be understood that the conditions suitable for protease activity apply to all of the processes of the present disclosure.

The term "g-force sufficient to separate the mixture" as used herein refers to the force necessary to separate the insoluble fiber fraction in the mixture from the protein fractions. In an embodiment, the g-force is between 100 g and 500 g, suitably between 150 g and 400 g, optionally between 170 g and 350 g. It will be understood that when the mixture is subjected to a sufficient g-force, the insoluble fiber, due to its relative higher density and/or greater particle size, will separate from the protein fractions. It should also be recognized that forces greater than the ranges necessary to separate the phases are not desirable as they can result in the high concentrations of the insoluble protein being deposited in the fiber phase. In addition, as a result of the insoluble protein fraction having a higher relative density and/or particle size compared to the soluble protein, the insoluble protein fraction will separate from the soluble protein fraction. It will be understood though that not all of the protein will separate from the insoluble fiber fraction, and likewise, not all of the insoluble fiber will separate from the protein fraction. Moreover, not all of the insoluble protein fraction will separate from the soluble protein fraction. Accordingly, when the mixture has been subjected to a g-force sufficient to separate the mixture, the insoluble fiber fraction will comprise at least 10% crude fiber, optionally 15%, 20%, 25, 30% crude fiber on a dry weight basis. Likewise, the protein fraction will comprise less than 10% crude fiber, optionally less than 5%, 4%, 3%, 2%, 1% and less than 1% crude fiber with the majority of other material comprising soluble and insoluble proteins, carbohydrate, ash and oil. In an embodiment, the g-force sufficient to separate the mixture is obtained by rotating a centrifuge at a speed of about 500 RPM to about 2,500 RPM. It will be understood that a centrifuge will have a rotational radius which will vary depending on the size of the centrifuge. In another embodiment, the g-force sufficient to separate the mixture is obtained by using a hydrocyclone with a g-force of between 50 g and 250 g.

(II) Protein Concentrates and Isolates

The present disclosure relates to processes for the production of a protein concentrate or a protein isolate from macroalgae and/or microalgae. A protein concentrate is an isolated protein extract of macroalgae and/or microalgae, wherein the extract has greater than 30% protein content but less than 90% protein content on a dry weight basis. A protein concentrate has been treated to separate protein in the macroalgae and/or microalgae from the fiber and other unwanted antinutritional factors. A protein isolate is an isolated protein extract of macroalgae and/or microalgae, wherein the extract has greater than or equal to 90% protein content on a dry weight basis. Typically, the protein isolate has up to 98%, 99%, 99.5% or 100% protein content on a dry weight basis. Typically, the non-protein content includes non-protein compounds such as antinutritional substances, fiber, and other components or impurities such as coloring agents.

In an embodiment, the disclosure provides a process for the removal of fiber, antinutritionals and other constituents, that are present within the algae. A person skilled in the art would recognize that antinutritionals include glucosinolates, phytic acid, phytates and other compounds that reduce the nutritional or commercial value of the protein concentrate or protein isolate. For example, antinutritional compounds may not be digestible by mammals (e.g humans), have adverse effects, such as toxicity, and are desirably removed from the protein product. Certain antinutritionals have other undesirable properties, such as undesirable organoleptic properties. Examples of such compounds are sinapine, which has a bitter taste, and sinigrin which has a pungent and very bitter flavor. Further, other antinutritional constituent of algae that are typically removed include, but are not limited to, coloring agents and/or other inert compounds. In an embodiment, the constituents which are removed or are reduced to safe or acceptable levels, are undesirable constituents or impurities using the processes of the present disclosure. A person skilled the art would recognize the safe and/or acceptable levels of particular antinutritionals in the final protein product.

In another embodiment of the disclosure, there is also included protein concentrates and protein isolates, produced in accordance with the processes of the disclosure.

In an embodiment, the protein concentrate possessing a protein content of about 30% to about 70% produced in accordance with the processes of the present disclosure are utilized as a protein ingredient in aquafeeds for fish, swine and pet foods.

In another embodiment, the protein concentrate possessing a protein content of about 30% to about 75% produced in accordance with the processes of the present disclosure are useful as a protein ingredient for baked food products such as bread, rolls, cake and pastry products (including mixtures for preparing baked food products), cookies, biscuits, crackers, pancakes, pastries, doughnuts, and other pasta products. In addition, this protein concentrate is useful as a protein ingredient in meat products such as baked meat, hot dogs, bologna, analogs, ham and sausages. Further, this protein concentrate is also useful as a protein ingredient in vegetarian foods. It will be understood by a person skilled in the art that this protein concentrate is also useful for other applications where a lower grade of protein concentrate is sufficient, such as in aquafeeds and pet foods as described above.

In another embodiment, the protein concentrate possessing a protein content of about 30% to less than 90% produced in accordance with the processes of the present disclosure is useful as a protein ingredient in breakfast cereals, and baked goods, as well as meat products such as bologna, frankfurters, luncheon loaves and ham. Further, this protein concentrate is useful in candies, confections, desserts, dietary items, Asian foods, soup mixes, gravies and other similar food items. Again, it will be understood by a person skilled in the art that this protein concentrate is also useful for other applications where a lower grade of protein concentrate is sufficient, such as in aquafeeds, pet foods, bakery products and meat products, as described above.

In another embodiment, the protein isolate possessing a protein content of greater than 90% produced in accordance with the processes of the present disclosure is useful as a protein ingredient in nutritional beverages such as protein fortified soft drinks, sports drinks, fruit juices and other high protein drinks. In addition, this protein isolate is useful as a protein ingredient for nutritional supplements, special diet products, and high protein nutritional tablets. In addition, the protein isolate is useful as a protein ingredient in infant formulas, as well as an ingredient in comminuted and emulsified meats, simulated meats, combination meat products and cured or uncured meat products. Further, the protein isolate is useful as a protein ingredient in pasta (eg. macaroni), bread and other bakery products, pancakes, waffles, crackers, donuts, pie crusts, soups, egg replacements, dried milk replacements and dairy analogs. Again, it will be understood by a person skilled in the art that this protein isolate is also useful for other applications where a lower grade of protein is sufficient, such as in aquafeeds, pet foods, and meat products, as described above.

In another embodiment, the hydrolyzed protein isolate possessing a protein content of greater than 90% produced in accordance with the processes of the present disclosure is useful as a protein ingredient in nutritional beverages such as protein fortified soft drinks, sports drinks, fruit juices and other high protein drinks. In addition, the hydrolyzed protein isolate is useful as a cosmetic ingredient. Further, the hydrolyzed protein isolate is useful as a protein ingredient for healthy food applications to improve absorption and digestibility. Again, it will be understood by a person skilled in the art that this hydrolyzed protein isolate is also useful for other applications where a lower grade of protein is sufficient, such as in aquafeeds, pet foods, bakery products and meat products, as described above.

(III) Processes of the Disclosure

A person skilled in the art would understand that depending on the identity of the macroalgae and/or microalgae, an oil extraction step may or may not be required. When an oil extraction is required, the algae are dried. Dried macroalgae and/or microalgae are mixed with solvent, such as hexane or methyl pentane, at a ratio of 1 to 3 to 1 to 10 by weight. The algae solvent slurry is milled (such as with a bead mill) to break the cell walls of the algae. This is followed by centrifugation to separate the oil in the solvent from the solids. The solvent extract is desolventized and dried to produce crude algae oil. The solids are desolventized and dried to produce defatted (partially or totally) macroalgae and/or microalgae, which are used in the processes of the present disclosure. In another embodiment, wet macroalgae and/or microalgae are wet milled, and optionally enzymatic hydrolysis using cellulase, to break the cell walls. This is followed by centrifugation to separate oil layer from aqueous layer. The oil layer is processed into oil. The aqueous layer is used as starting material for the processes of the present disclosure. Depending on the identity of the macroalgae and/or microalgae, the oil content may be minimal, such that it is not necessary to perform an oil extraction step.

Figure 2:
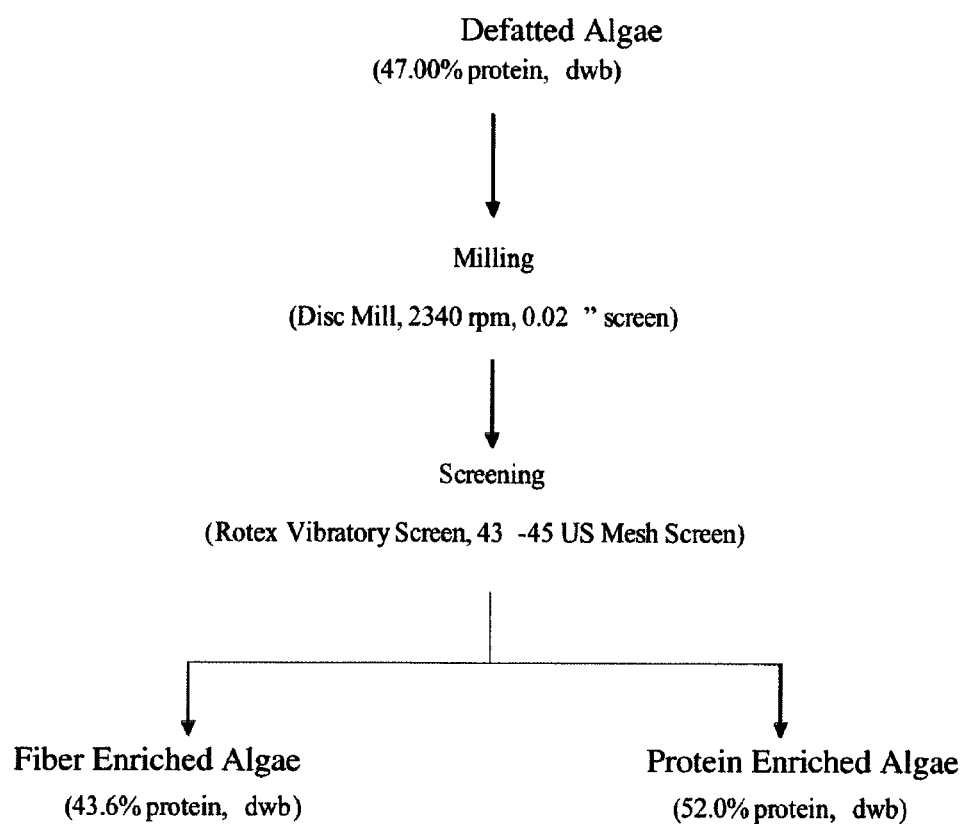
FIG. 2 is a schematic representation in a first embodiment showing the milling and screening of defatted algae.
Figure 3:
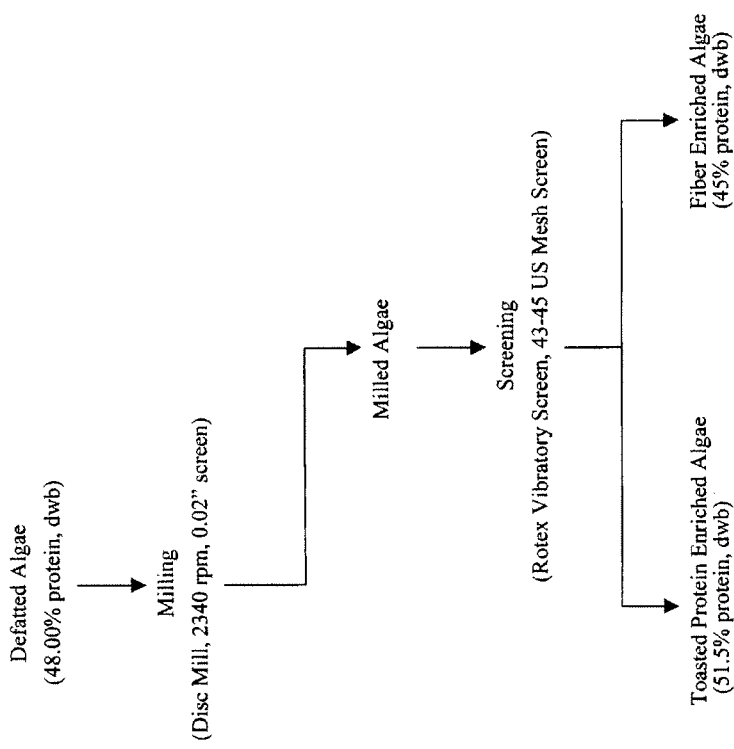
FIG. 3 is a schematic representation in a second embodiment illustrating a milling and screening process of defatted algae.

A general method for obtaining a protein-enriched algae is shown in FIGS. 1-3. For example, when beginning with algae, the moisture content of the algae is adjusted. The moisture adjusted algae is optionally exposed to a heat treatment. In an embodiment of the processes of the present disclosure, the algae is heat treated to a temperature of about 60° C. to about 120° C., optionally about 70° C. to about 100° C., or about 80° C. to about 90° C., or about 80° C. In another embodiment, the heat treatment is carried out at a temperature of 100° C. The heat treatment of the algae results in the inactivation of the enzymes present in the algae, for example, myrosinase, lipase, phospholipase. If the algae is not heat treated, the enzymes (such as myrosinase, lipase, phospholipase), as a result of their enzymatic action, can degrade the oil and breakdown glucosinolates releasing sulphur into oil. At a temperature of about 75-100° C., the enzymes are deactivated, and are therefore not able to degrade the oil and breakdown glucosinolates releasing sulphur into oil. Accordingly, in an embodiment, a heat treatment temperature of 75-100° C. results in a reasonably high protein dispersibility index (PDI), lower sulphur, FFA and phosphorus in pressed and butane/R134a extracted oils.

Alternatively, in an embodiment, the algae is not exposed to a heat treatment and its moisture content is not adjusted. It will be understood by a person skilled in the art that the moisture content of the algae is typically in the range of about 7% to about 10% for a pressing operation. If the moisture content of the algae is not in this range, the moisture of the algae is optionally adjusted to about 7% to about 10% by adding water or drying, which is followed by blending and tempering.

The algae is then subjected to a milling step and a screening step to obtain a protein-enriched algae.

The algae is typically milled, for example with a disc mill or a hammer mill, to reduce the particle size of the algae. When using a disc mill, the algae is forced through two rotating discs which crush the algae. When a hammer mill is used to reduce the particle size of the algae, the algae is loaded into the hammer mill, wherein the hammers reduce the particle size of the algae.

After the particle size of the algae has been sufficiently reduced, the milled algae is screened through mesh screens, which results in an initial separation of a fiber fraction from the algae, resulting in a protein-enriched algae. Fiber tends to have a larger particle size which is not able to pass through the screen. However, a portion of the fiber will be able to pass through the screen, and as such, only a portion of the fiber is removed by screening. Typically, about a 45 US mesh screen is used for the initial fiber separation. This is a dry screening process which results in a fiber enriched algae, which does not pass through the screen, and the protein-enriched algae, which does pass through the screen. The protein-enriched algae, however, still contains a significant amount of fiber and other antinutritional factors. In an embodiment of the disclosure, it is this protein-enriched algae that is utilized to produce the protein concentrates and protein isolates of the present disclosure. However, in another embodiment, it will be apparent to those skilled in the art that macroalgae and/or microalgae, a partially or totally defatted algae or a protein-enriched algae is utilized with the processes of the present disclosure. The use of such macroalgae and/or microalgae, and processing with a minimum amount of heat during conditioning, pressing, solvent extraction, desolventization and drying, leads to better protein concentrates and protein isolates.

In an embodiment of the present disclosure, there is a process for removing fiber from macroalgae and/or microalgae. In particular, the process relates to separating and removing fiber from algae based on the density and particle size differences between the fiber particles and the protein particles. The separation and removal of fiber is accomplished by using separation methods, at specific speeds, which can separate particles based on their density or particle size such as centrifugation, gravity sedimentation, a gravity table or hydrocyclone to separate the fiber from the mixture and form the protein slurry. In an embodiment, the separation is accomplished using centrifugation. In another embodiment, the separation is accomplished using a decanter centrifuge. In another embodiment, the separation is accomplished using a decanter centrifuge at a speed of about 1,000 rpm to about 2,000 rpm. In another embodiment, the separation is accomplished using a decanter centrifuge at a speed of about 1,500 rpm. In an embodiment, the centrifugation of a algae mixture results in three layers: i) an insoluble fiber layer and a protein slurry on top of the fiber, which is comprised of ii) an insoluble protein fraction and iii) a soluble protein fraction. Separation of the top and middle layers (the soluble protein extract and the insoluble fine protein fraction) from the bottom layer (coarse fiber solids), results in a protein slurry with fiber removed.

Figure 4:
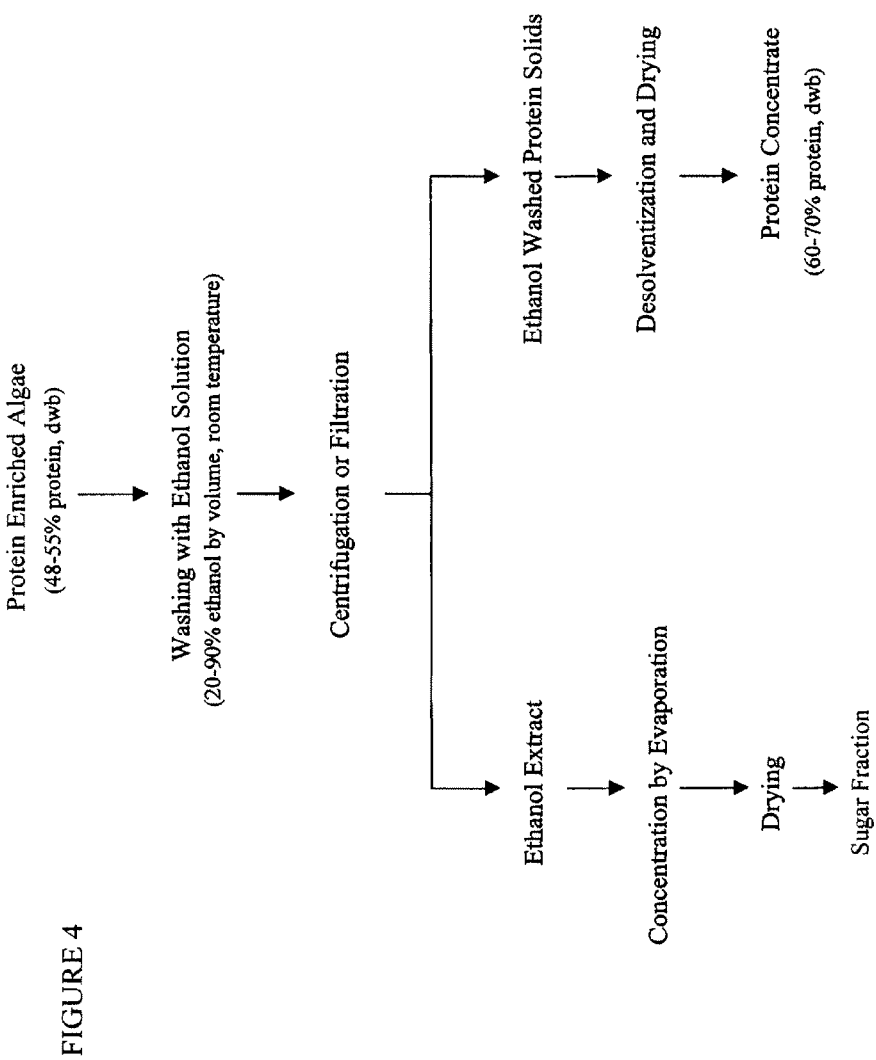
FIG. 4 is schematic representation showing a preparation of a protein concentrate from a protein-enriched algae.
Figure 5:
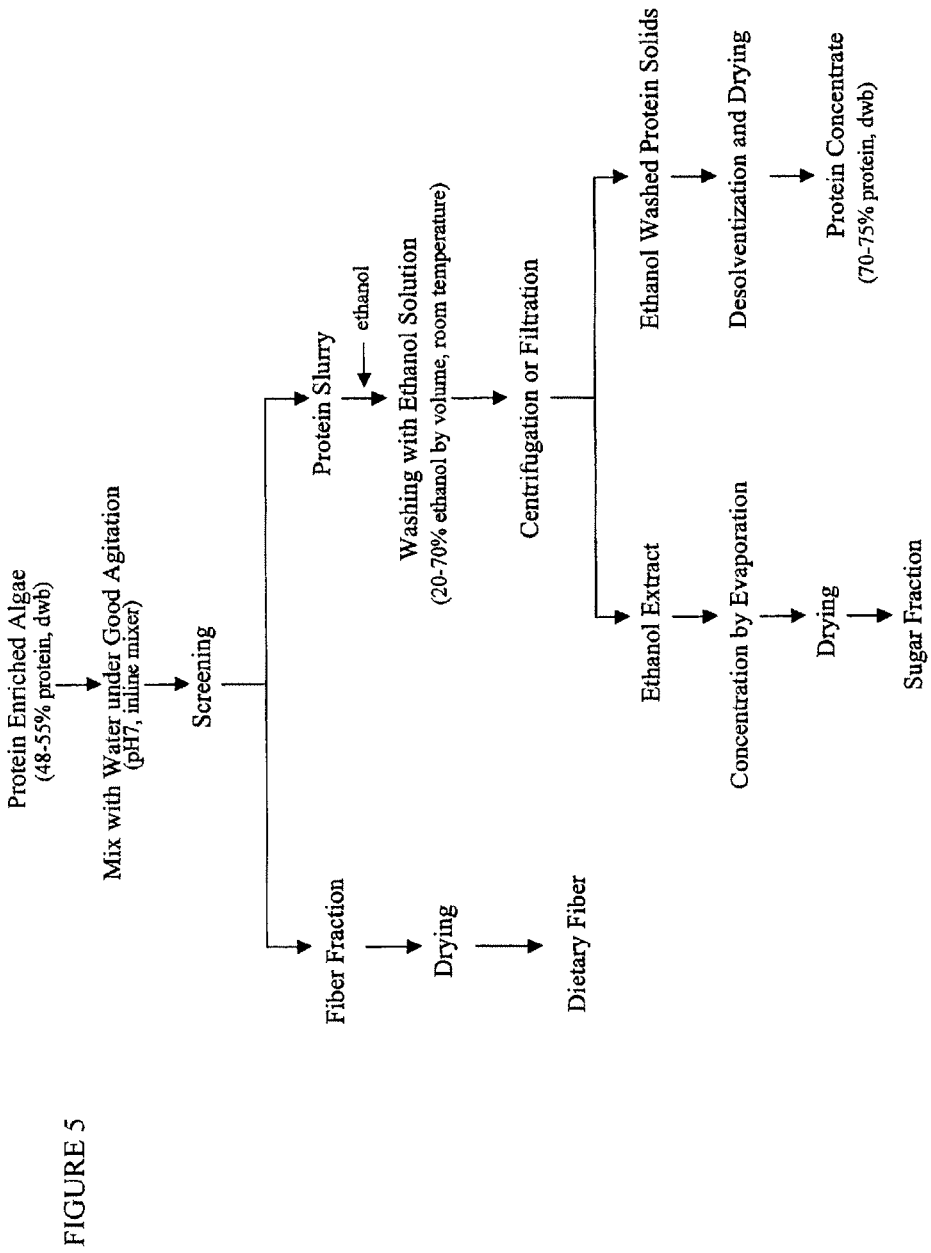
FIG. 5 is a schematic representation in a first embodiment showing the removal of fiber during a preparation of a protein concentrate from a protein-enriched algae.
Figure 6:
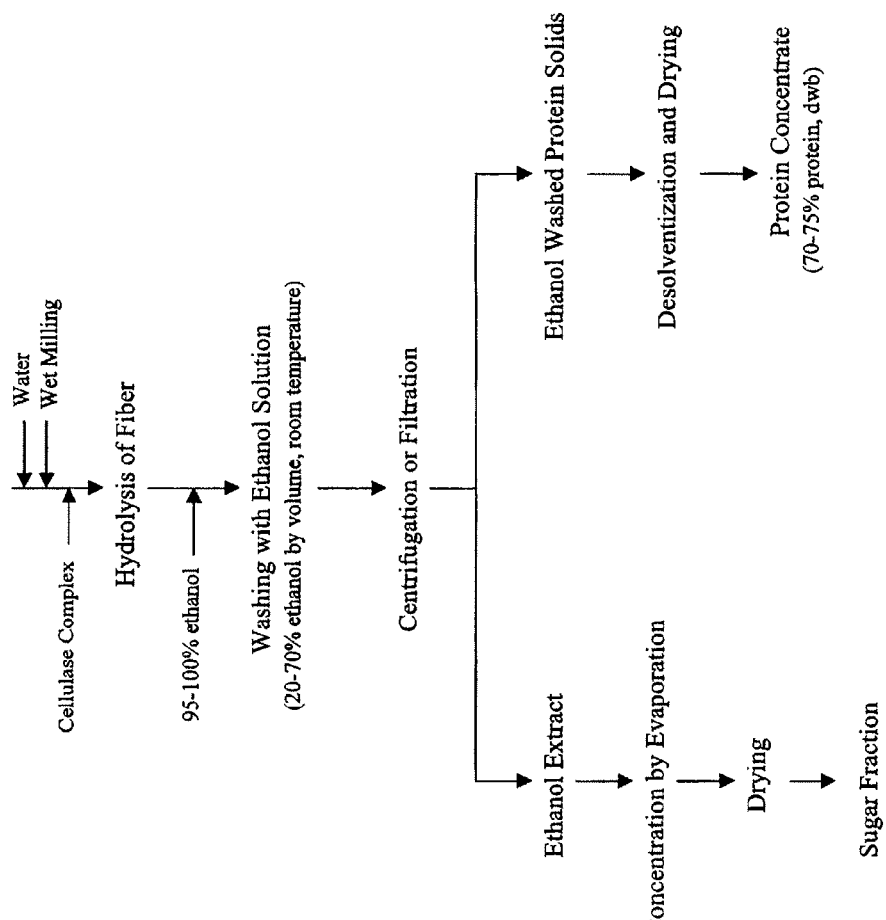
FIG. 6 is a schematic representation in a second embodiment showing the removal of fiber during a preparation of a protein concentrate from a protein-enriched algae.
Figure 7:
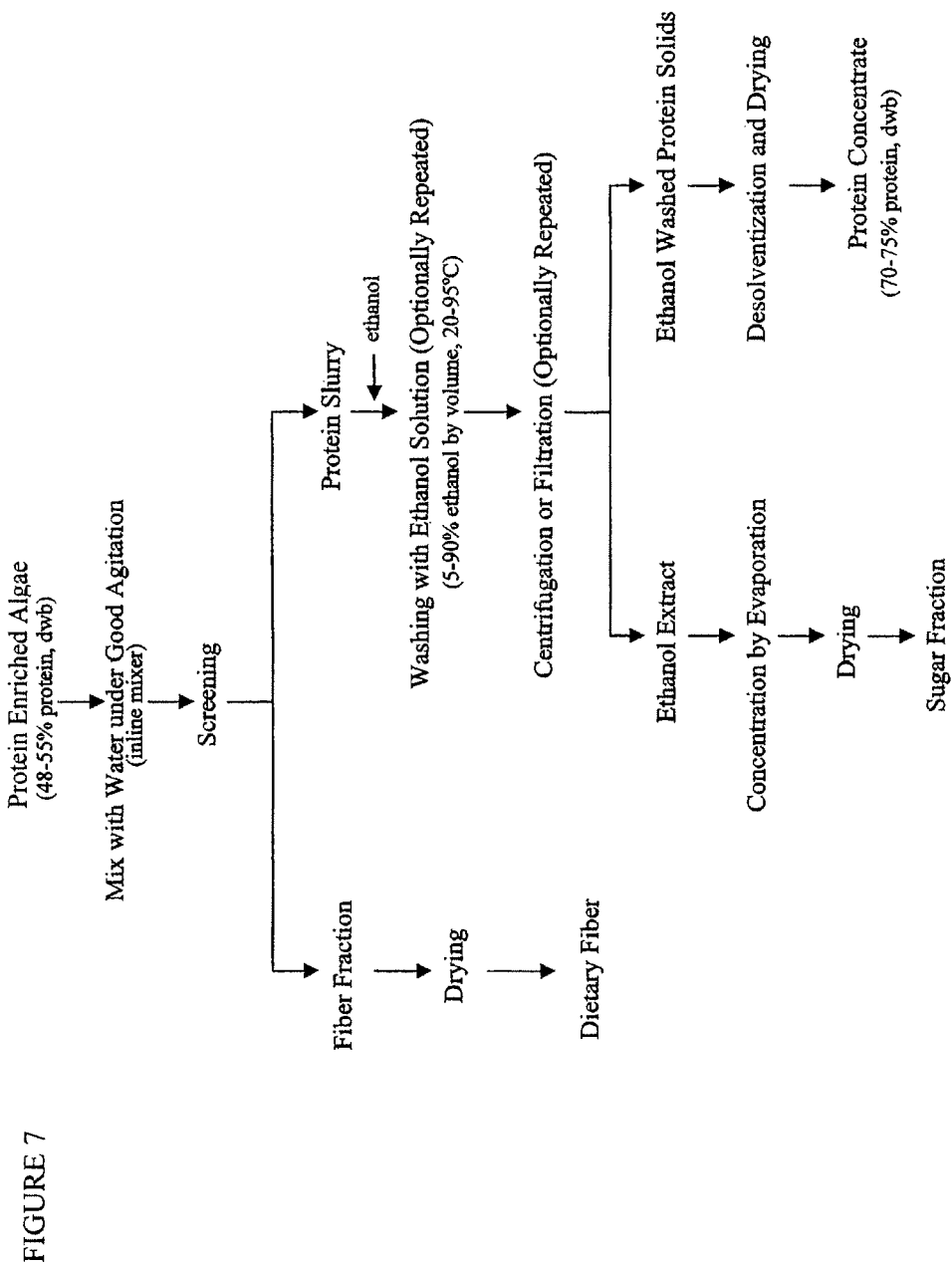
FIG. 7 is a schematic representation in a third embodiment showing the removal of fiber during a preparation of a protein concentrate from a protein-enriched algae.
Figure 8:
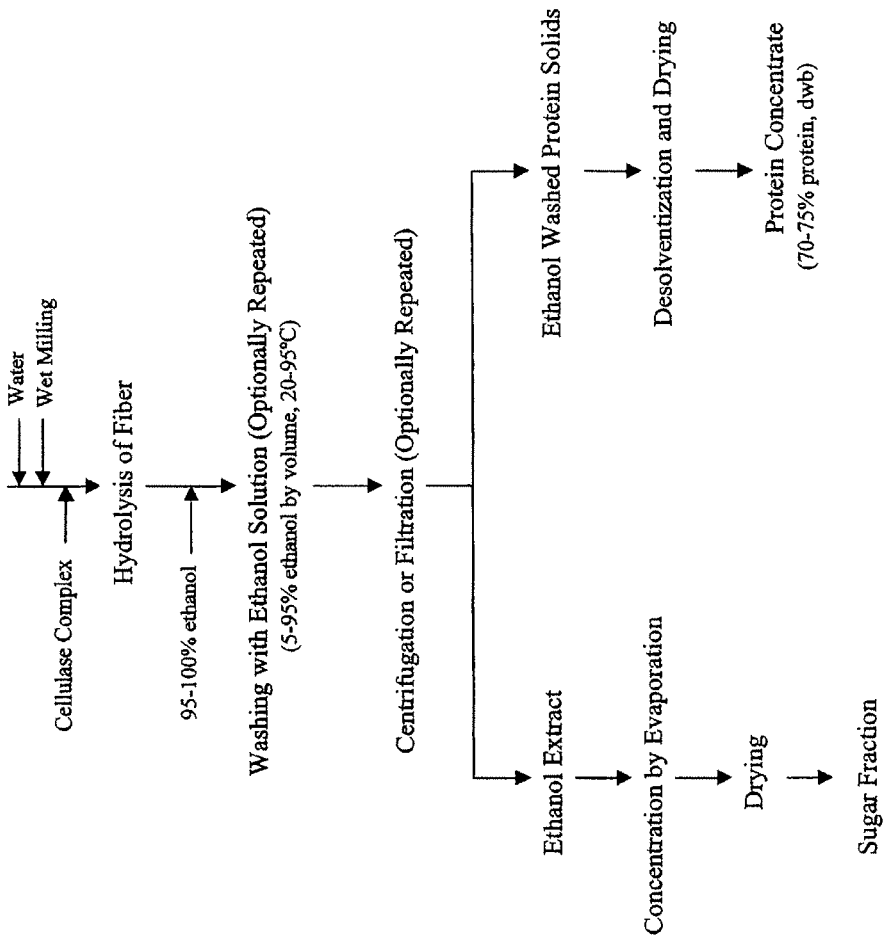
FIG. 8 is a schematic representation in a fourth embodiment showing the removal of fiber during the preparation of a protein concentrate from a protein-enriched algae.

In an embodiment of the present disclosure, a process for the production of a protein concentrate possessing a protein content of about 30% to about 60% is obtained from macroalgae and/or microalgae. An optional general process for the production of a protein concentrate is illustrated in FIG. 4.

In an embodiment, macroalgae and/or microalgae is produced by the process above, and is then washed at least once with about 5% to about 100%, optionally about 20% to about 90%, or about 40% to about 80% (v/v) ethanol in water, resulting in an ethanol extract and an ethanol washed macroalgae and/or microalgae. Other alcohols, such as methanol or isopropanol, can be utilized for washing the macroalgae and/or microalgae. In an embodiment, ethanol is used for washing the macroalgae and/or microalgae because it is less toxic than other alcohols, and a higher percentage of ethanol residue is allowed in the final product.

In another embodiment, the macroalgae and/or microalgae is washed once with ethanol, wherein the ratio of ethanol to the protein-enriched algae is about 1:3 to about 1:15, typically about 1:4 to about 1:8, optionally 1:6, on a weight-to-weight basis of protein-enriched algae to ethanol.

In another embodiment, the macroalgae and/or microalgae is washed twice with ethanol, wherein the amount of ethanol added to the protein-enriched algae results in a ratio of about 1:2 to about 1:15, typically about 1:5 to about 1:8, optionally 1:6, on a weight-to-weight basis of protein-enriched algae to ethanol. Typically, washing the macroalgae and/or microalgae at least twice results in the removal of more impurities from the macroalgae and/or microalgae and therefore increases the protein content in the protein concentrate.

In a further embodiment, the macroalgae and/or microalgae is washed in a counter-current extractor. In this embodiment, the macroalgae and/or microalgae is washed about 2 times to about 10 times, wherein the ratio of solvent to the macroalgae and/or microalgae is about 1 to about 10 of algae to about 1 of algae.

In another embodiment, the macroalgae and/or microalgae is washed with ethanol at a temperature of about 10° C. to about 90° C., optionally 20° C. to about 60° C., suitably at a temperature of about 40° C. to about 60° C.

The ethanol extract is optionally separated from the ethanol washed macroalgae and/or microalgae by centrifugation, filtration, vacuum filtration, pressure filtration, sedimentation, decantation or gravity draining. With respect to centrifugation, the ethanol mixture is typically fed to a decanter centrifuge or a basket centrifuge. The ethanol extract is then separated from the ethanol washed macroalgae and/or microalgae by centrifugal force. For the decanter centrifuge, a screw conveyer is contained within a solid bowl and both rotate at high speeds. Solids settling on the bowl are conveyed by the screw conveyer out of the centrifuge. For a basket centrifuge, which consists of a perforated basket rotating inside a stationary housing, the ethanol mixture is fed into the basket and centrifugal force pushes it against the filter liner. The solids are retained by the liner while the liquid passes through. For filtration, the ethanol extract is typically separated from the ethanol washed macroalgae and/or microalgae by draining through a perforated belt or basket in a reactor. For vacuum filtering or pressure filtering, the separation is aided by vacuum or pressure. In an embodiment, the ethanol extract is concentrated by evaporation of the ethanol to form a high sugar fraction, optionally containing antinutritional factors that can be further purified. The antinutritional compounds may be purified into valuable pharmaceutical, medicinal or chemical compounds, such as glucosinolates, phytic acid or phytates, sinapine and sinigrin. In an embodiment, the ethanol extract is heated under vacuum at about 30° C. to about 90° C., which results in the evaporation of ethanol and water, and soluble solids are left behind. Ethanol is further separated from water by distillation and re-used in the process. The concentrated high-sugar fraction is dried by spray drying, rotary drum drying, vacuum drying, flash drying, ring drying, microwave drying, freeze drying or using a fluidized bed dryer.

In another embodiment, the washed macroalgae and/or microalgae is dried to form the protein concentrate, possessing a protein content of about 30% to about 70%. In a further embodiment, the washed protein-enriched algae is dried in a spray dryer, drum dryer, vacuum dryer, fluidized bed dryer or ring dryer to form the protein concentrate possessing a protein content of about 30% to about 70%. These dryers remove the solvent by drying the protein concentrate under a vacuum or at atmospheric pressure at elevated temperatures of about 30° C. to about 100° C.

In an embodiment, the protein concentrate is dried to a moisture content of about 1% to about 10%, optionally about 4% to about 8%.

In another embodiment, the ethanol that is removed through drying is recovered and recycled so it can be used again in further ethanol extractions. The ethanol is recovered through evaporation and distillation.

In another embodiment, the dried protein concentrate possessing a protein content of about 30% to about 70% is further milled into powder form without coarse particles.

In another embodiment of the present disclosure, there is provided a process for producing a protein concentrate possessing a protein content of about 30% to about 75% on a dry weight basis. In an embodiment, a general process for the production of a protein concentrate possessing a protein content of about 30% to about 75% is illustrated in FIGS. 5-8, where the removal of fiber is also detailed. In an embodiment, the use of an extraction solvent, such as ethanol, leads to a protein concentrate or protein isolate having superior organoleptic properties, as well as superior water solubility properties, which therefore possesses better functional properties.

Accordingly, in an embodiment of the present disclosure, a process for the production of a protein concentrate from macroalgae and/or microalgae is disclosed, comprising:
1) removing fiber from the defatted or protein-enriched macroalgae and/or microalgae, comprising either:
   i) mixing the macroalgae and/or microalgae with a mixing solvent to form a first mixture;
      screening the first mixture through a mesh screen of about 10 to about 200 US mesh size to remove the fiber; or
   ii) mixing the macroalgae and/or microalgae with water to form a second mixture;
      optionally adjusting the pH of the second mixture to a pH of about 3 to about 7; and
      adding cellulase complex to the second mixture and heating to a temperature of about 30° C. to about 60° C. to hydrolyze the fiber;
2) washing the first or second mixture with an extraction solvent to form an extract and a washed macroalgae and/or microalgae;
3) separating the extract from the washed defatted or protein-enriched algae;

4) optionally repeating steps 2) and 3) at least one more time; and
5) desolventizing the washed macroalgae and/or microalgae to form a protein concentrate.

In an embodiment of the present disclosure, the mixing solvent is any solvent which forms a slurry with the macroalgae and/or microalgae when mixed together and is able to suspend the protein within the mixture. In another embodiment, the mixing solvent comprises water, methanol, ethanol, or isopropanol, or mixtures thereof. In a further embodiment, the mixing solvent comprises water or ethanol, and mixtures thereof.

In an embodiment of the disclosure, the macroalgae and/or microalgae is mixed with a mixing solvent in a ratio of about 3 to about 10 parts solvent to about 1 part of the macroalgae and/or microalgae, on a weight-to-weight basis.

In an embodiment of the present disclosure, the pH of the first mixture is adjusted to a pH of about 3.0 to about 10.0, optionally about 6.8 to about 7.2 with a solution of an alkali metal base or an acid, such as phosphoric, hydrochloric or sulphuric acid. In a further embodiment, a solution of an alkali metal base comprising about 1% to about 40% by weight, optionally about 5% to about 30%, of the alkali metal base and water is added to the first mixture. In another embodiment, the alkali metal base comprises sodium hydroxide (NaOH).

In another embodiment of the present disclosure, the first mixture is thoroughly agitated. In another embodiment, an inline mixer is used for thorough mixing of the first mixture. Thorough mixing of the first mixture disperses the protein particles and releases natural sugar compounds that are trapped inside the insoluble protein particles in the mixing solvent. In addition, the agitation suspends the solids of the protein-enriched algae in the mixing solvent.

In a further embodiment, the thoroughly mixed first mixture is wet screened resulting in a separation of the fiber from the mixture which contains the protein. In another embodiment of the disclosure, the mesh screen comprises a US mesh screen of about 20 to about 200 US mesh. In a further embodiment, the mesh screen is a vibratory screen. A person skilled in the art would recognize that other screens, for example revolving screens, shaking screens or oscillating screens, could be used in place of vibratory screens to perform substantially the same function of vibrating the mixture which aids in separation of the first mixture from the fiber. In an embodiment of the disclosure, the fiber in the algae swells upon addition of the mixing solvent, increasing the particle size of the fiber. Consequently, the mesh screen prevents the fiber from passing through, while the protein in the first mixture passes through the screen, resulting in a separation of the fiber from the protein. In an embodiment, the fiber fraction is dried and can be used in dietary fiber products. The fiber fraction optionally contains protein and carbohydrates.

In another embodiment of the present disclosure, the macroalgae and/or microalgae is thoroughly mixed with water to form the second mixture. In an embodiment, wet milling is used to mix the second mixture. In another embodiment, an inline mixer is used to thoroughly mix the second mixture. In an embodiment, the mixing of the macroalgae and/or microalgae in water, results in the internal fiber structure being exposed, which allows for the cellulase complex to efficiently hydrolyze the fiber.

In a further embodiment of the disclosure, the pH of the second mixture is optionally adjusted with an acid. In an embodiment, the pH of the second mixture is adjusted to a pH that is suitable for the activity of an enzyme within the second mixture. In an embodiment, the pH of the second mixture is adjusted to a pH of about 3 to about 7. The pH of the second solution is adjusted with an acid solution. In an embodiment, the acid solution is phosphoric acid, hydrochloric acid or sulfuric acid. In an embodiment, the natural pH of the second mixture is about 6.8 to about 7.2, and therefore the pH of the second mixture is not adjusted.

In another embodiment of the present disclosure, the cellulase complex is added to the second mixture in an amount of about 1 to about 10 grams (about 0.1% to about 1%) to about 1 kg of dried solids in the second mixture. In a further disclosure, the cellulase complex is mixed with the second mixture for about 0.5 hours to about 5 hours. In another embodiment, the cellulase complex is mixed with the second mixture for about 1 to about 3 hours. It will be apparent to those skilled in the art that cellulase complex contains different types of cellulase enzyme. For example, cellulase complex contains at least one of endocellulase, exocellulase, cellobiohydrolase, cellobiase, endohemicellulase and exohemicellulase. Cellulase enzymes possess enzymatic activity which are able to hydrolyze the fiber to constituent sugars within the second mixture.

In another embodiment of the present disclosure, the first or second mixture is washed at least once with about 5% to about 100%, optionally about 25% to about 85%, or about 50% to about 85%, or about 60% to about 85%, of the extraction solvent (v/v) in water. The addition of the extraction solvent precipitates proteins in the first or second mixture, while the carbohydrates from the algae from the hydrolyzation of the fiber remain in the extraction solvent, which allows for separation. It will be understood that an extraction solvent will be any solvent which dissolves the carbohydrates and other undesirable compounds, but precipitates the protein. In embodiment, the extraction solvent is water, methanol, ethanol or isopropanol, and mixtures thereof. In another embodiment, the extraction solvent is ethanol. It will be understood by a person skilled in the art that if the extraction solvent comprises 100% extraction solvent, no water will be present in the extraction solvent. For example, the extraction solvent could be 100% ethanol. In another embodiment, the extraction solvent is 60% ethanol in water.

In an embodiment of the present disclosure, the extraction solvent is added in an amount to adjust the ratio of the extraction solvent to the first or second mixture of about 5% to about 95%, optionally about 10% to about 90%, or about 40% to about 80% (v/v) of the extraction solvent.

In an embodiment of the present disclosure, the first or second mixture is washed with an extraction solvent at a temperature of about 10° C. to about 90° C. In another embodiment, the first or second mixture is washed with the extraction solvent at a temperature of about 20° C. to about 60° C. In a further embodiment, the first or second mixture is washed with the extraction solvent at a temperature of about 20° C. to about 25° C.

In another embodiment of the present disclosure, the extract is separated from the washed macroalgae and/or microalgae by centrifugation, vacuum filtration, pressure filtration, decantation or gravity draining. In an embodiment, the extract is concentrated by evaporation of the extraction solvent dried to form a high sugar fraction, as is performed above.

In another embodiment of the disclosure, steps 2) and 3) are optionally repeated at least once. In an embodiment, steps 2) and 3) are repeated at least twice. Repeating steps 2) and 3) results in a protein product containing less impurities, such as fiber and other antinutritional factors.

In another embodiment, the washed macroalgae and/or microalgae is dried to form the protein concentrate, possessing a protein content of about 50% to about 75% on a dry weight basis. In a further embodiment, the washed macroalgae and/or microalgae is dried in a vacuum dryer, fluidized bed dryer, spray dryer or ring dryer to form the protein concentrate possessing a protein content of about 30% to about 75%.

In another embodiment, the washed macroalgae and/or microalgae is dried to a moisture content of about 0.5% to about 12%, optionally about 1% to about 10%, or about 4% to about 8%. In a further embodiment, the washed macroalgae and/or microalgae is dried to a moisture content of about 6%.

In another embodiment of the disclosure, the extraction solvent that is removed through drying is recovered and recycled so it can be used again in further extractions.

In another embodiment, the dried protein concentrate possessing a protein content of about 30% to about 75% is further milled into powder form.

Figure 9:
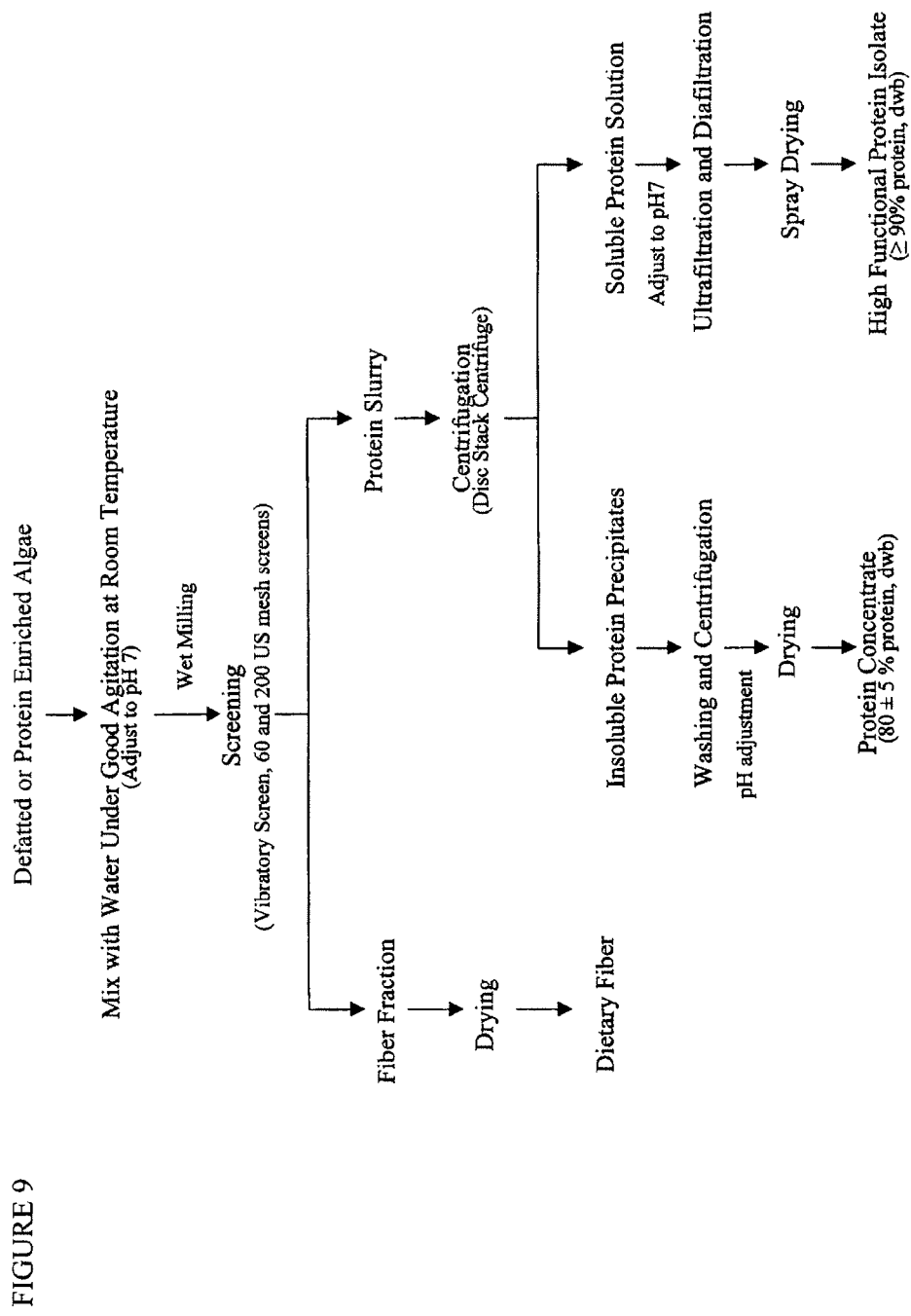
FIG. 9 is a schematic representation in a first embodiment showing a preparation of a protein concentrate and a protein isolate from a protein-enriched algae.
Figure 10:
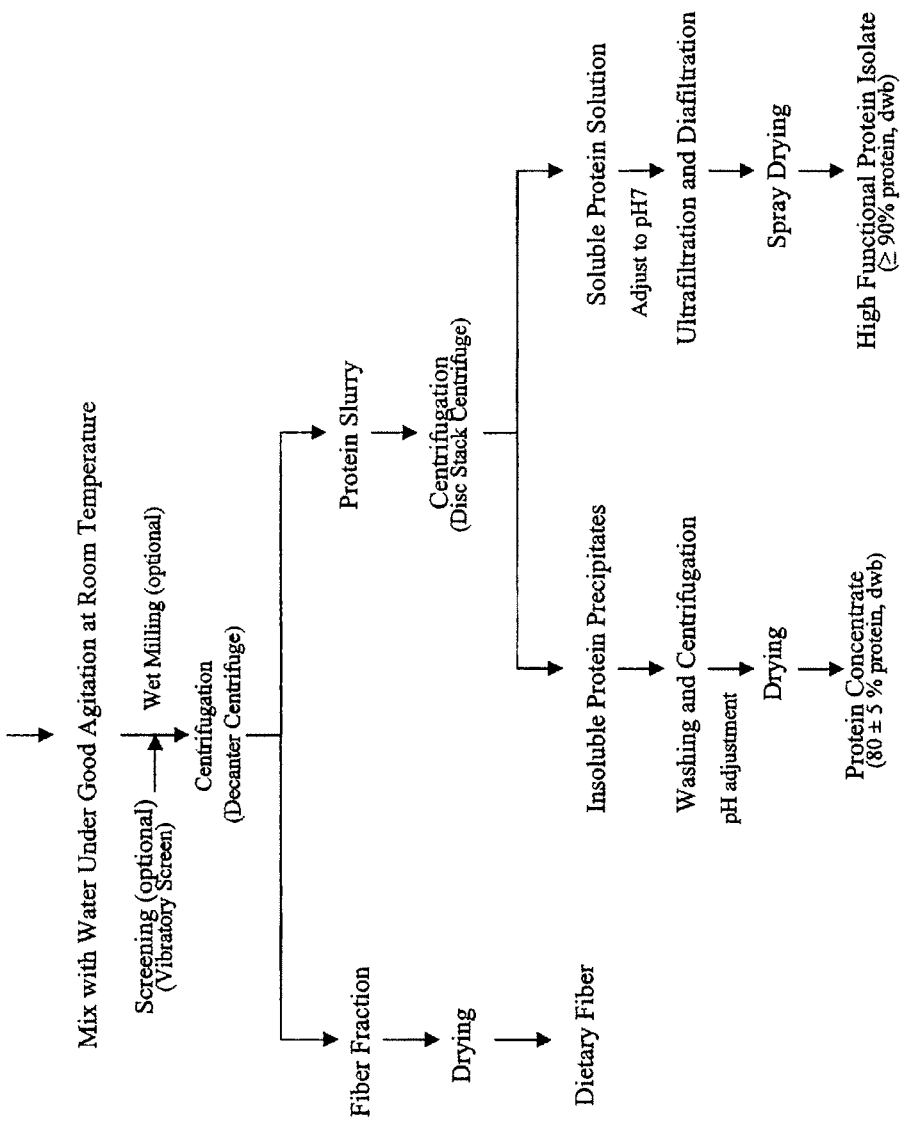
FIG. 10 is a schematic representation in a second embodiment showing a preparation of a protein concentrate and a protein isolate from a protein-enriched algae.

In another embodiment of the present disclosure, there is disclosed a process for the production of a protein concentrate comprising a protein content of about 30% to less than 90% on a dry weight basis. In an embodiment, a general process for the production of a protein concentrate possessing a protein content of about 30% and a protein isolate having a protein content greater than 90% is illustrated in FIGS. 9-10.

Accordingly, a process for the production of a protein concentrate from macroalgae and/or microalgae is disclosed, comprising:

removing fiber from the defatted or protein-enriched macroalgae and/or microalgae, comprising:
i) mixing the macroalgae and/or microalgae with a mixing solvent to form a mixture;
   optionally screening the mixture through a mesh screen of about 10 to about 200 US mesh size to remove fiber,
   optionally adjusting the pH of the mixture to a pH of about 7;
   optionally milling the mixture;
   centrifuging the mixture to remove fiber,
   and forming a protein slurry; and
ii) centrifuging the protein slurry to form a protein precipitate and a soluble protein fraction;
iii) washing the protein precipitate with an extraction solvent at least once and centrifuging to form a purified protein precipitate;
iv) drying the purified protein precipitate to form the protein concentrate.

It will be understood by a person skilled in the art that the steps of the process do not have to be followed exactly. For example, a person skilled in the art would recognize that the milling step could be performed before the screening step.

In an embodiment of the disclosure, the mixing solvent is any solvent which forms a slurry with the macroalgae and/or microalgae and is able to suspend the protein within the mixture. In another embodiment, the mixing solvent comprises water, methanol, ethanol, or isopropanol, and mixtures thereof. In a further embodiment, the solvent comprises water or ethanol, and mixtures thereof.

In an embodiment, the macroalgae and/or microalgae is mixed with the mixing solvent to form a mixture in a ratio of macroalgae and/or microalgae to mixing solvent of about 1:3 to about 1:20, optionally about 1:6 to about 1:10, or about 1:6 to about 1:8.

In a further embodiment, the mixture is wet screened resulting in a separation of the fiber from the mixture which contains the protein. In another embodiment of the disclosure, the mesh screen comprises a US screen of size about 20 to about 200 mesh. In a further embodiment, the mesh size is 40 US mesh size. In another embodiment, the mesh screen is a vibratory screen. The mesh screen prevents the fiber from passing through, while the protein in the mixture passes through the screen, resulting in a separation of the fiber from the protein. In an embodiment, the fiber fraction is dried and can be used in dietary fiber products. In an embodiment, protein and carbohydrates are present in the fiber fraction.

In another embodiment, the pH of the mixture is adjusted to about 7 with the addition of aqueous sodium hydroxide. In a further embodiment, the aqueous sodium hydroxide is a solution of about 1% to about 40%, optionally about 5% to about 30%, by weight of sodium hydroxide in water.

In another embodiment, the mixture is optionally milled using a wet milling process. In an embodiment, the wet milling of the mixture results in thorough mixing of the macroalgae and/or microalgae with the mixing solvent. Thorough mixing of the mixture disperses the protein particles and releases natural sugar compounds that are trapped inside the insoluble protein particles in the mixing solvent. In addition, the mixing suspends the solids of the protein-enriched algae in the mixing solvent.

In another embodiment of the present disclosure, the mixture is centrifuged using a decanting centrifuge. In an embodiment, the mixture is centrifuged with a decanting centrifuge at a speed of about 1000 rpm to about 2000 rpm. In another embodiment, the speed is about 1500 rpm.

In another embodiment, the protein slurry is then centrifuged using a disc stack centrifuge to separate insoluble proteins from soluble proteins, forming a protein precipitate and a soluble protein fraction. In an embodiment, the protein slurry is pumped to a disc centrifuge. The centrifuge has a bowl which spins at about 7500 rpm. As the slurry enters the centrifuge bowl, the slurry is brought up to the same speed as the bowl, which results in high centrifugal forces, about 6500 times the force of gravity acting on the mixture. The heavier protein precipitate is forced to the outside of the bowl. The soluble protein fraction is forced towards the axis of the bowl. The heavy precipitate collects around the outside of the bowl which are removed from the bowl periodically or continuously. The protein slurry is fed to the centrifuge continuously while the liquid soluble protein fraction is pumped out continuously. In an embodiment, the disc centrifuge operates at a speed of about 6500 rpm to about 8500 rpm.

In a further embodiment, the protein precipitate is washed with an extraction solvent to purify the protein precipitate and dissolve residual sugars and other non-desirable compounds. It will be understood that an extraction solvent will be any solvent which dissolves the carbohydrates and other non-desirable compounds. In an embodiment, the extraction solvent is water, methanol, ethanol or isopropanol, and mixtures thereof. In another embodiment, the extraction solvent is water or ethanol, and mixtures thereof. In another embodiment, the extraction solvent is water. In an embodiment, the protein precipitate is washed at least twice with the extraction solvent.

In another embodiment, the washed protein precipitate is then centrifuged again with a disc stack centrifuge at a speed of about 6500 rpm to about 8500 rpm to obtain a protein precipitate. In another embodiment, the washing extracts from the centrifugation are added to the soluble protein fraction.

In another embodiment, the washed protein precipitate is dried to form a protein concentrate comprising a protein content of about 30% to about 90% on a dry weight basis. In a further embodiment, the washed protein precipitate is dried in a vacuum dryer, fluidized bed dryer or ring dryer to form the protein concentrate possessing a protein content of about 30% to less than 90%. It will be understood by a person skilled in the art that the washed protein precipitate can be used as a protein isolate without drying. However, the dried protein isolate has a better shelf life as removal of the solvent, for example water, results in a more stable protein isolate.

Figure 11:
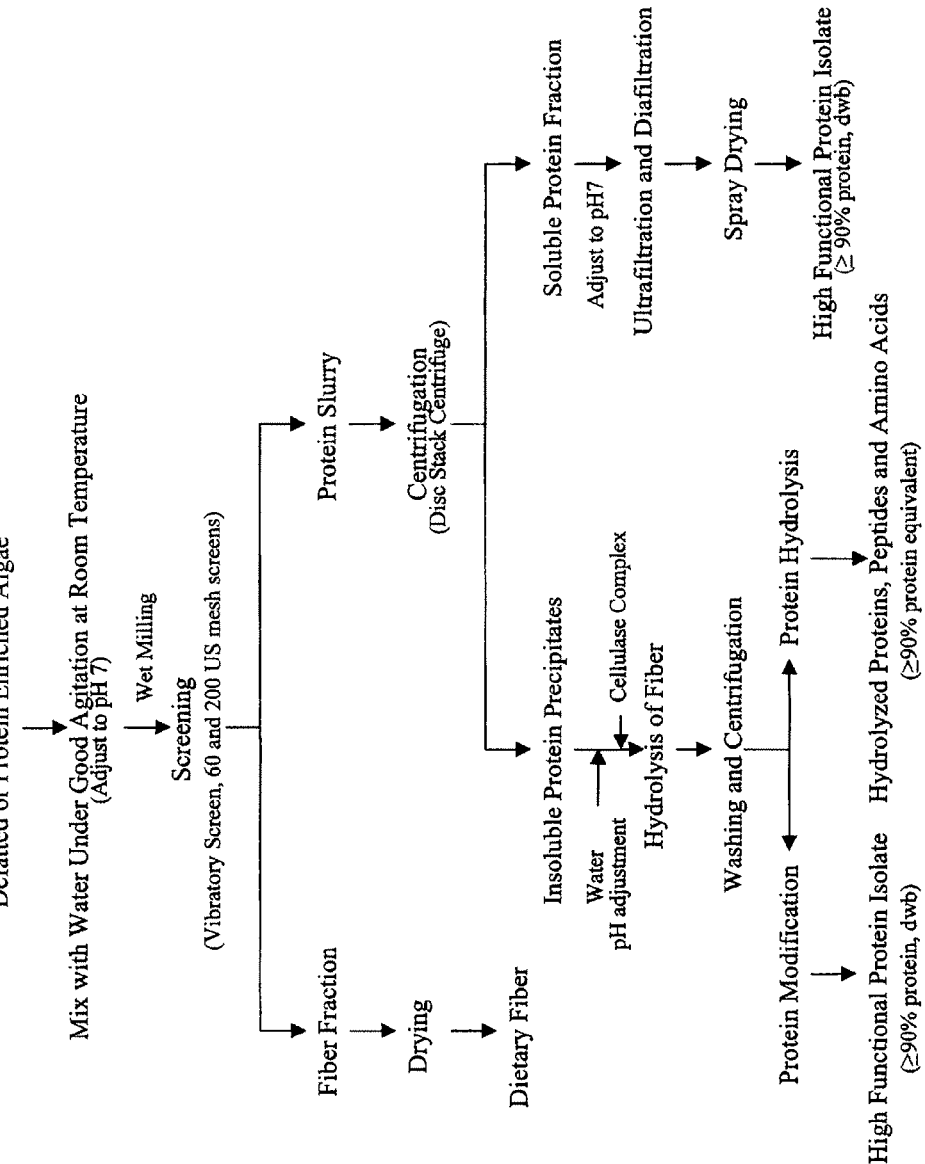
FIG. 11 is a schematic representation in a first embodiment showing a preparation of a protein isolate from a protein-enriched algae.
Figure 12:
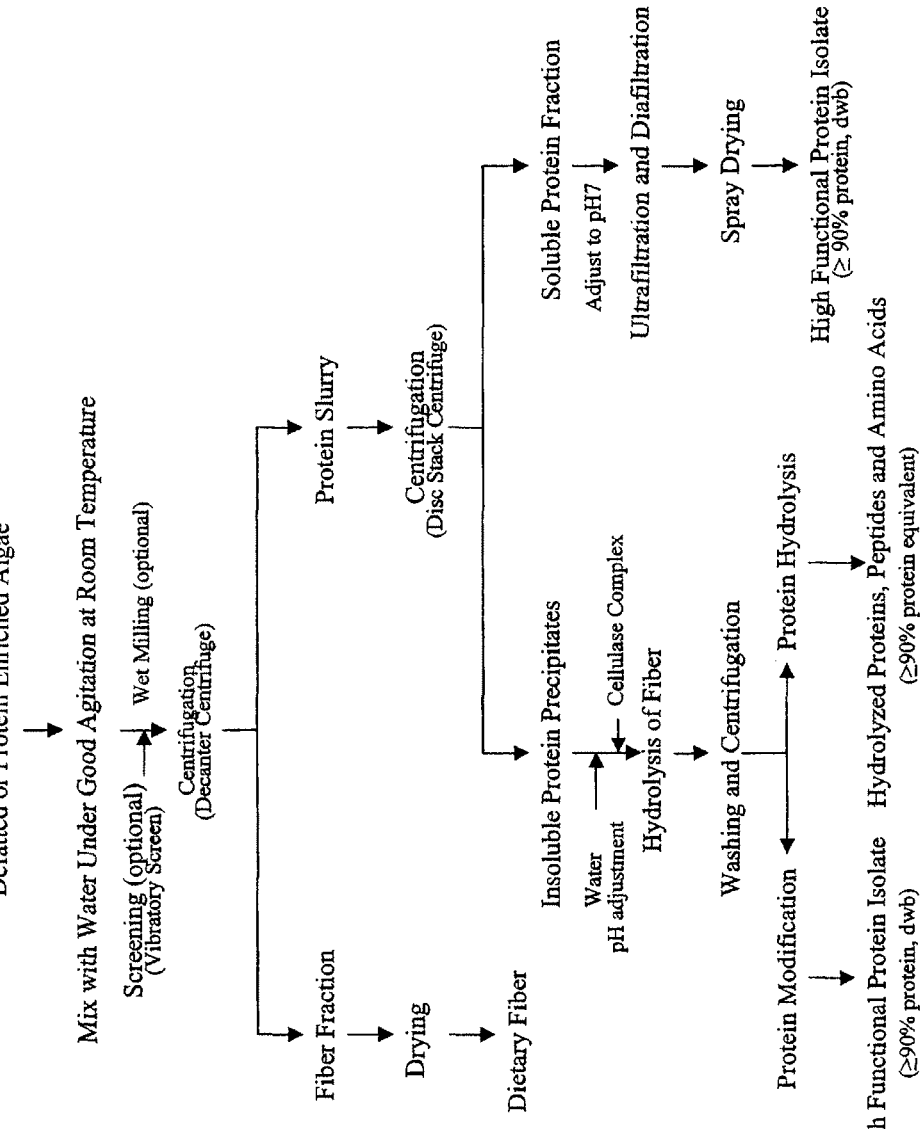
FIG. 12 is a schematic representation in a second embodiment showing a preparation of a protein isolate from a protein-enriched algae.
Figure 13:
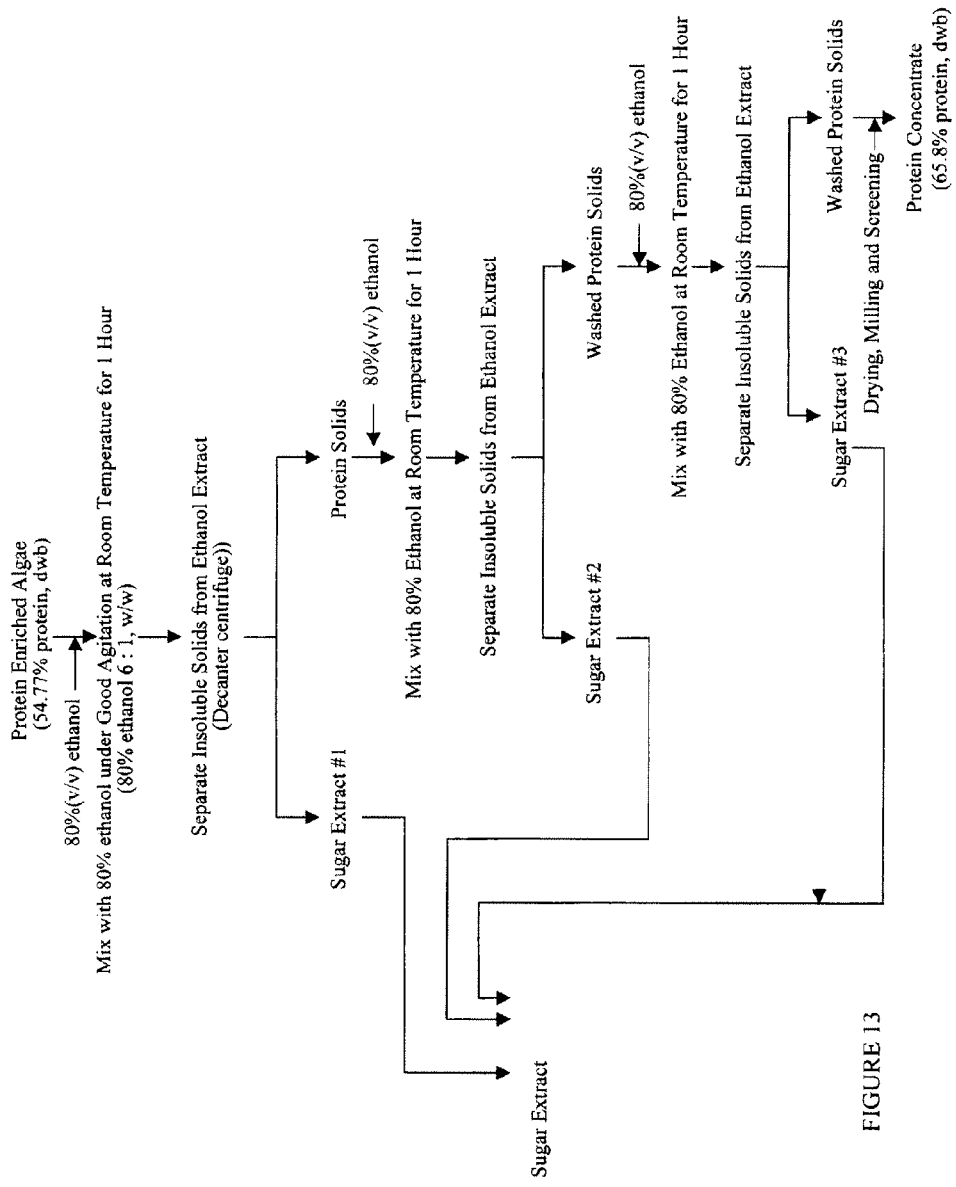
FIG. 13 is a schematic representation in a first embodiment showing a preparation of a protein concentrate from a protein-enriched algae.
Figure 14:
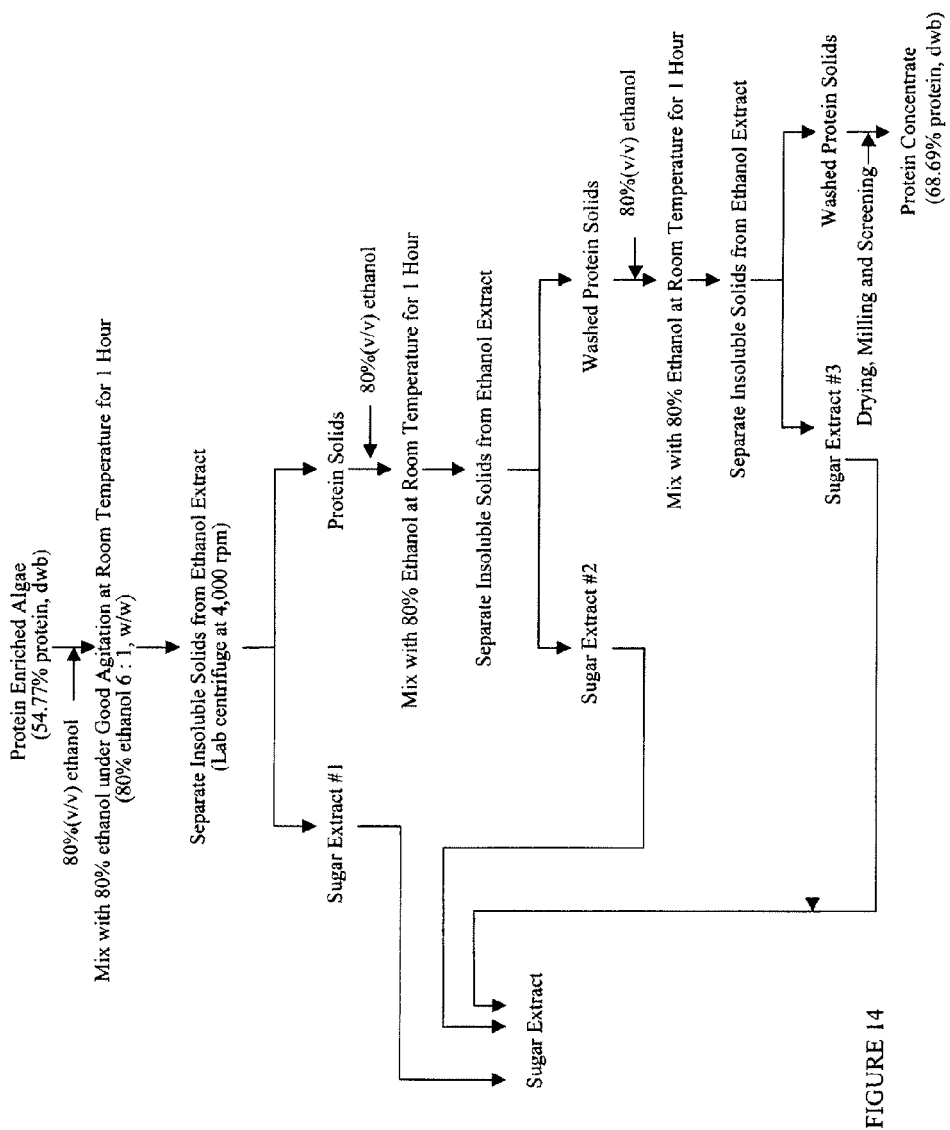
FIG. 14 is a schematic representation in a second embodiment showing a preparation of a protein concentrate from a protein-enriched algae.
Figure 15:
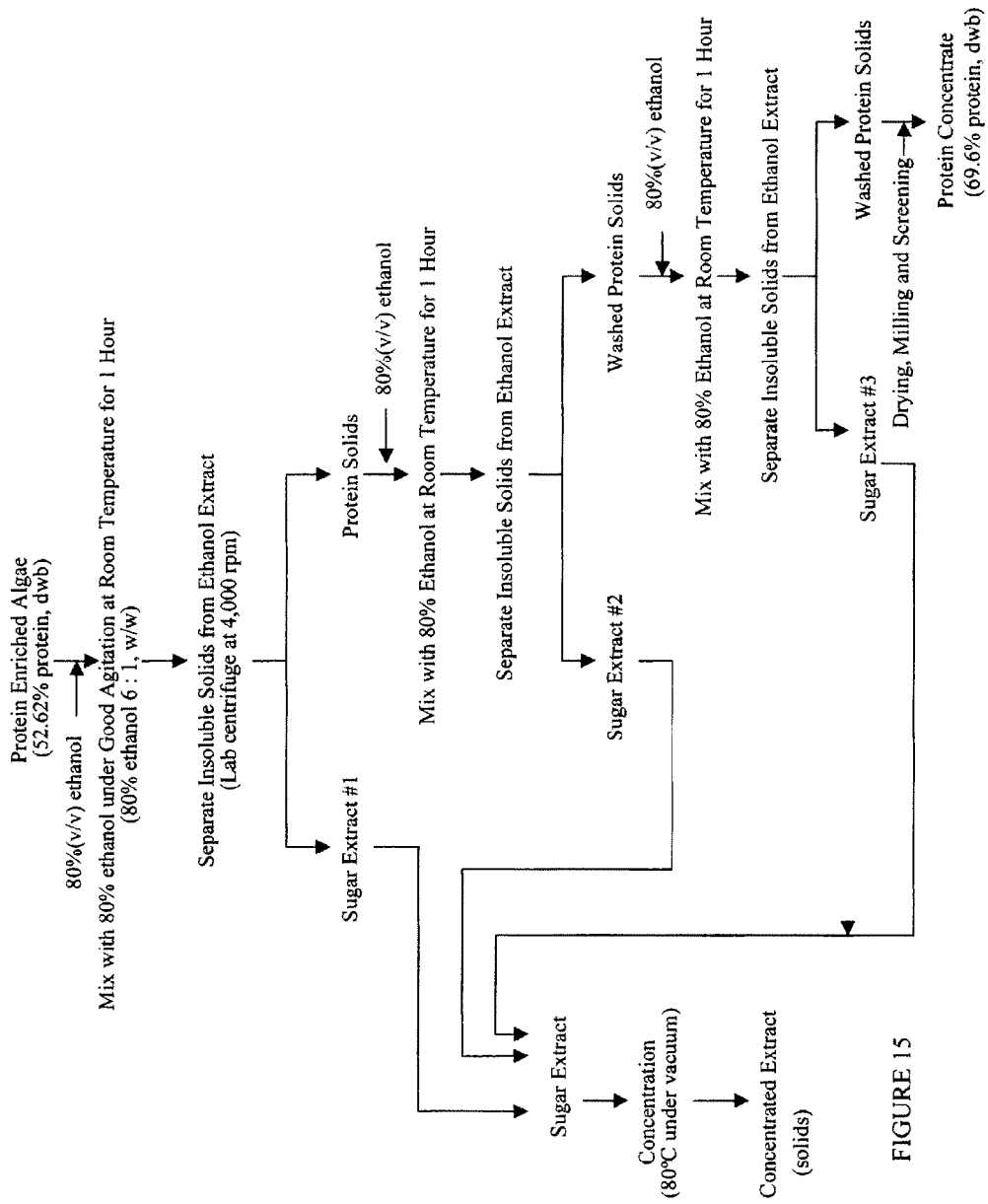
FIG. 15 is a schematic representation in a third embodiment showing a preparation of a protein concentrate from a protein enriched algae.
Figure 16:
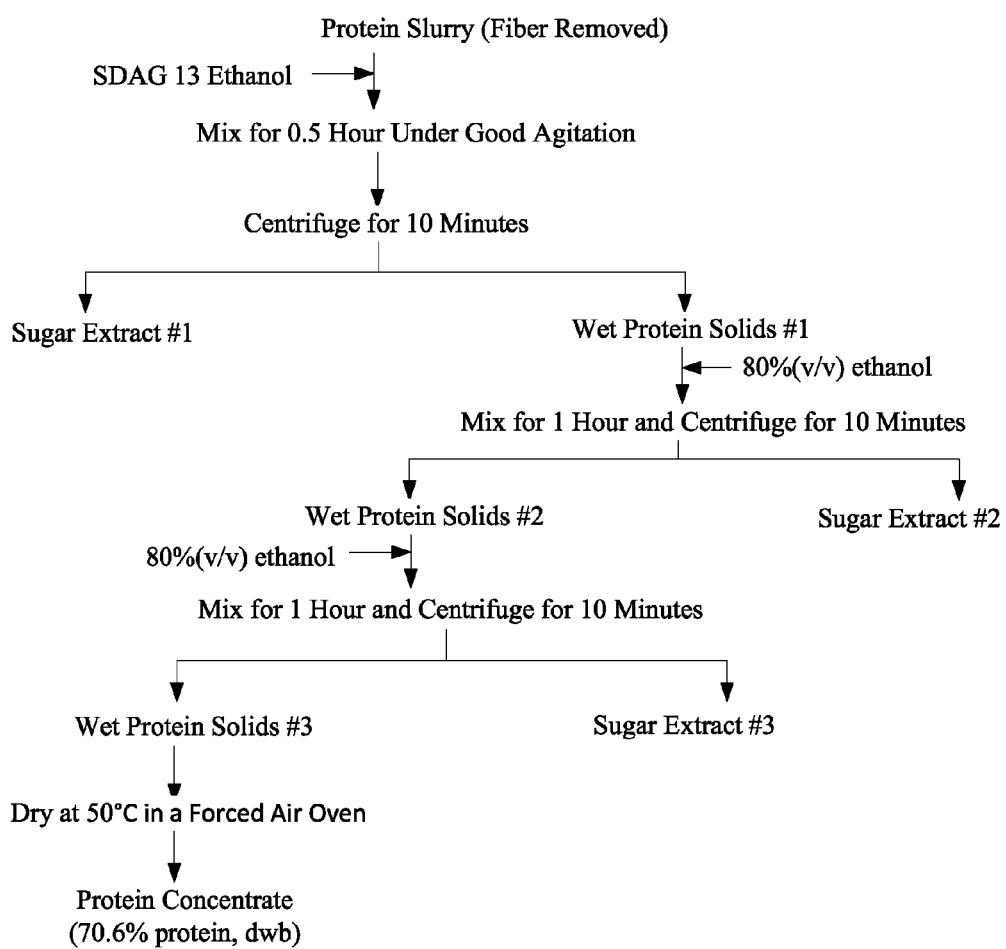
FIG. 16 is a schematic representation illustrating a preparation of a protein concentrate from a protein slurry with fiber removed.
Figure 17:
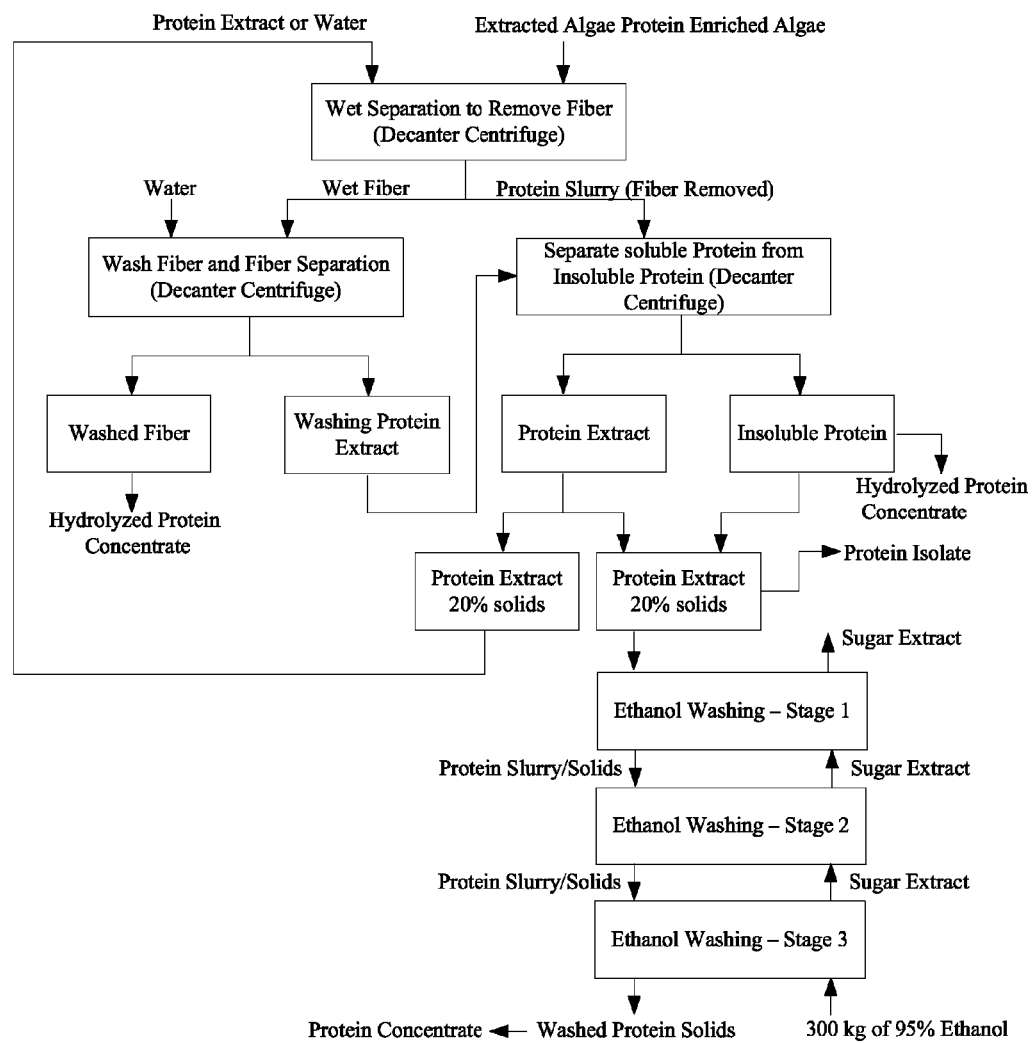
FIG. 17 is a schematic representation illustrating a wet fiber removal process.
Figure 18:
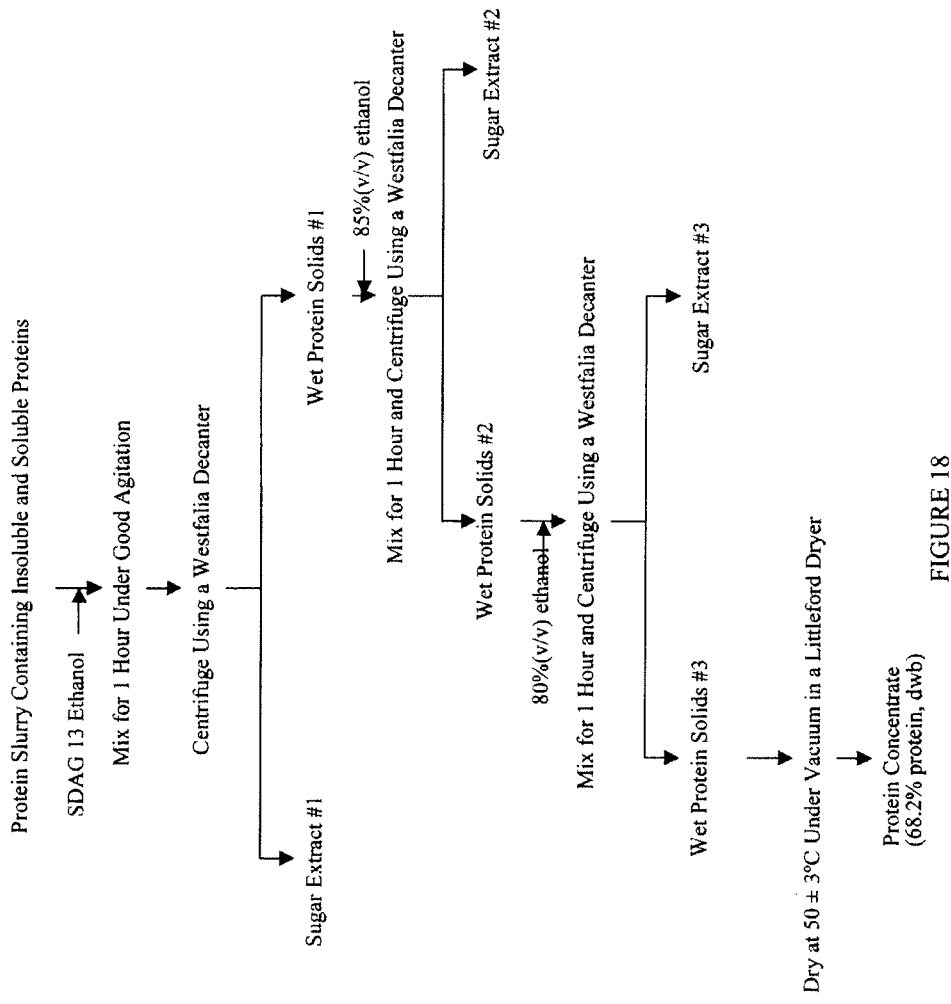
FIG. 18 is a schematic representation illustrating a preparation of a protein concentrate from a protein slurry after the removal of fiber.
Figure 19:
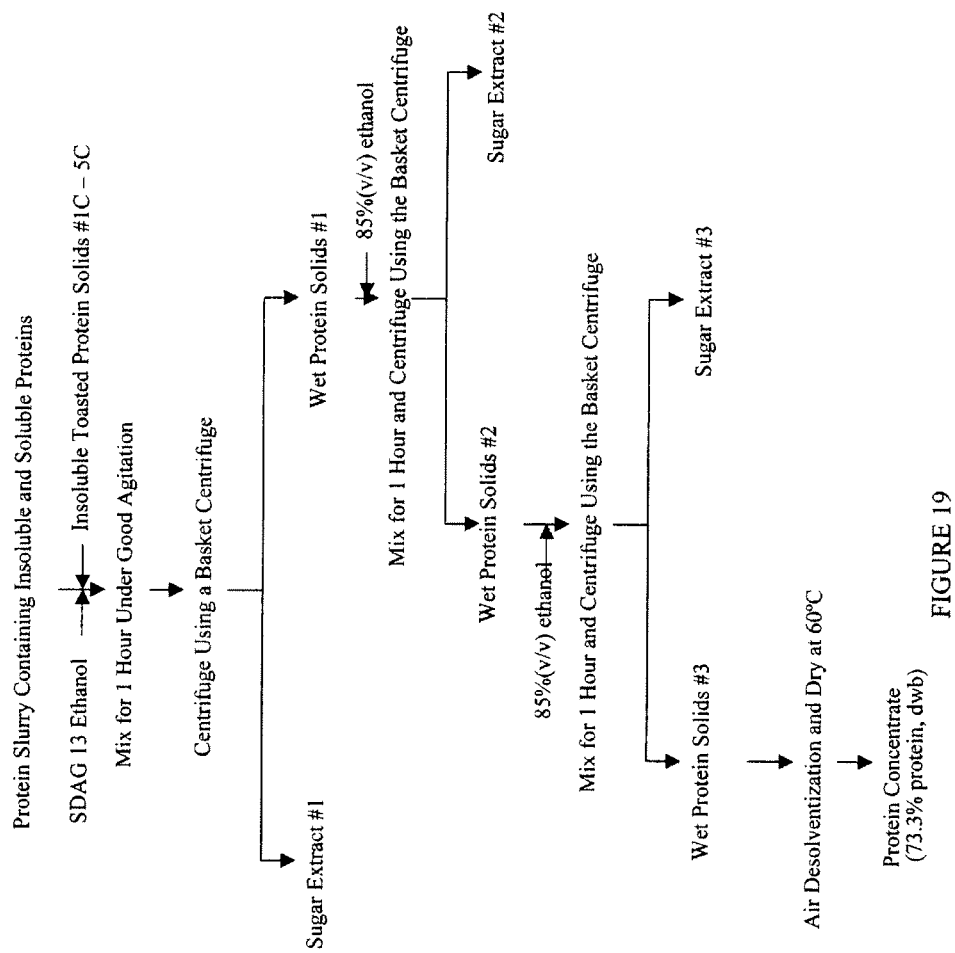
FIG. 19 is schematic representation illustrating a preparation of a protein concentrate produced by recycling a protein fraction.
Figure 20:
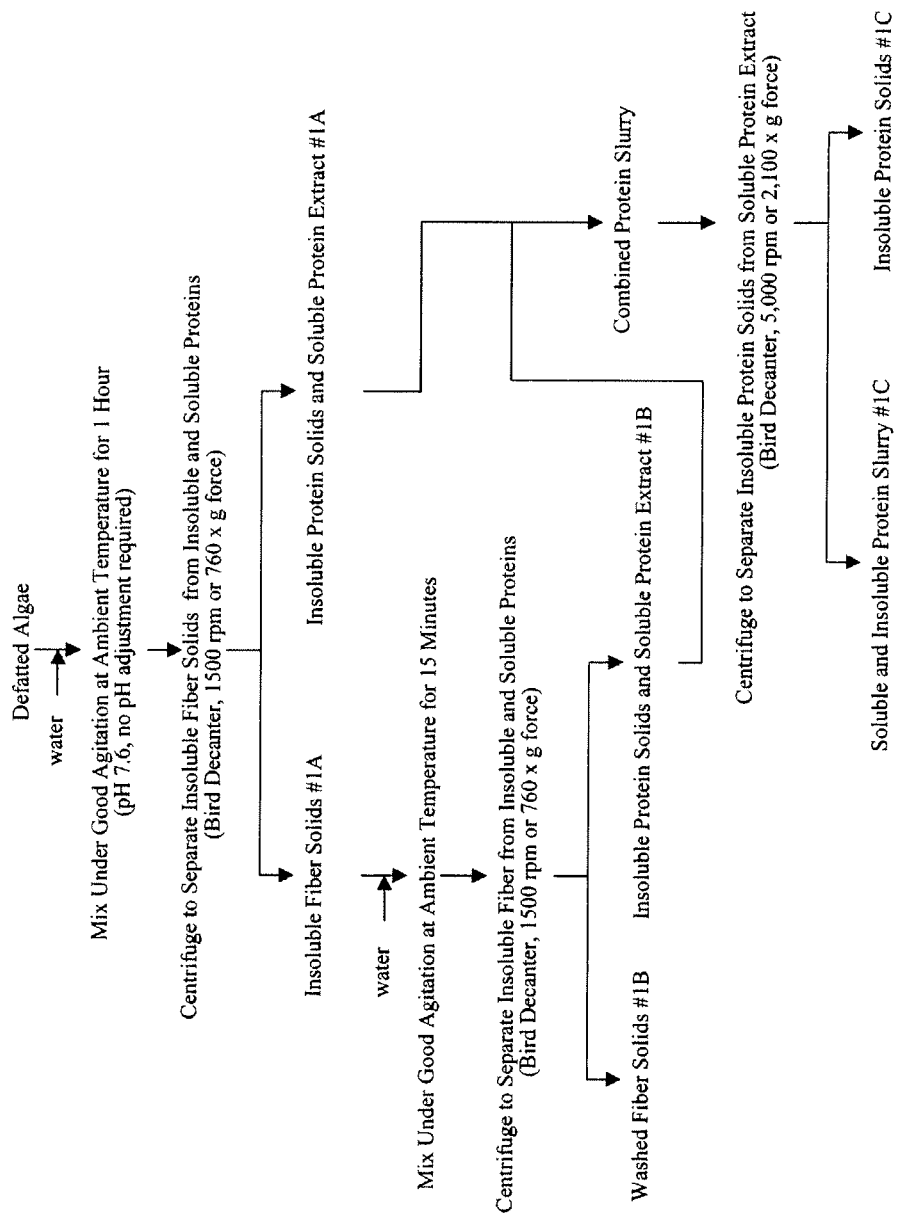
FIG. 20 is a schematic representation illustrating a wet fiber removal process.
Figure 21:
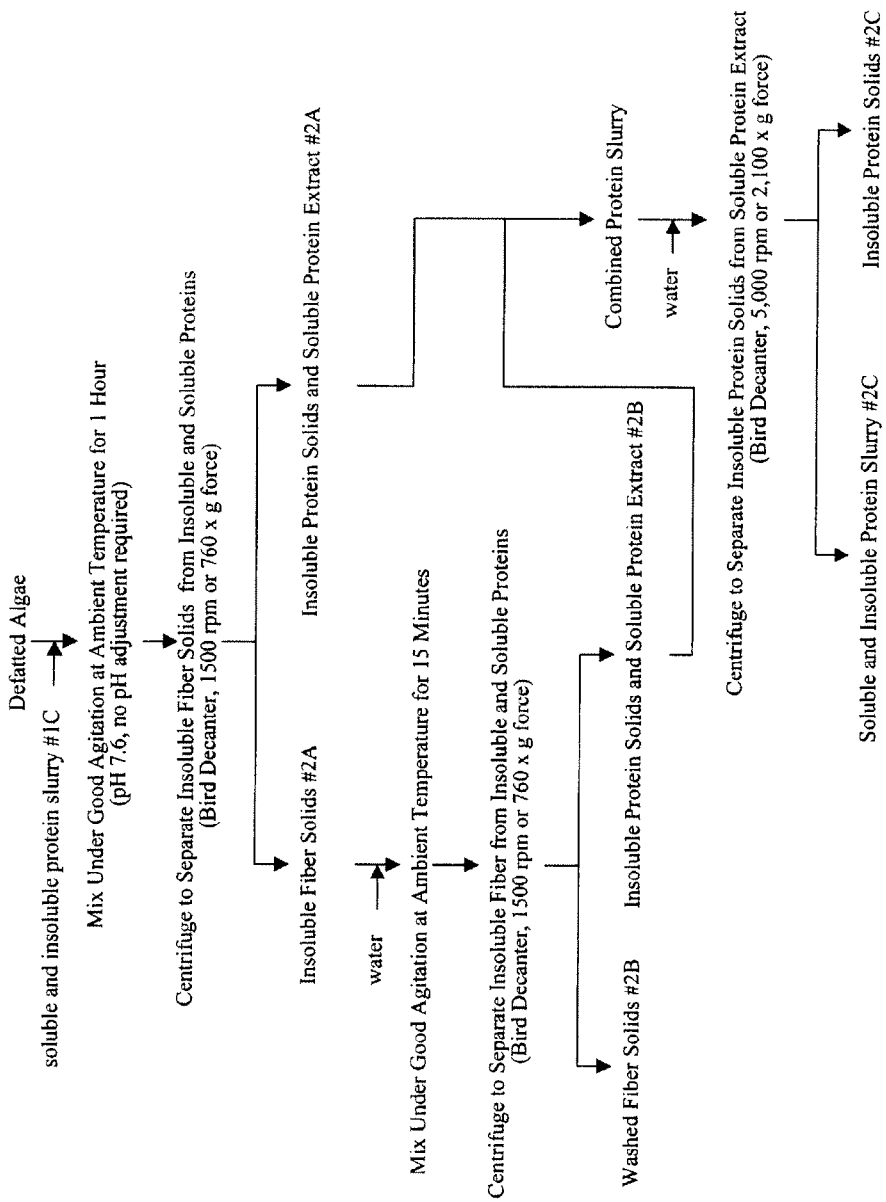
FIG. 21 is a schematic representation illustrating a first recycling of a protein fraction and a wet fiber removal process.
Figure 22:
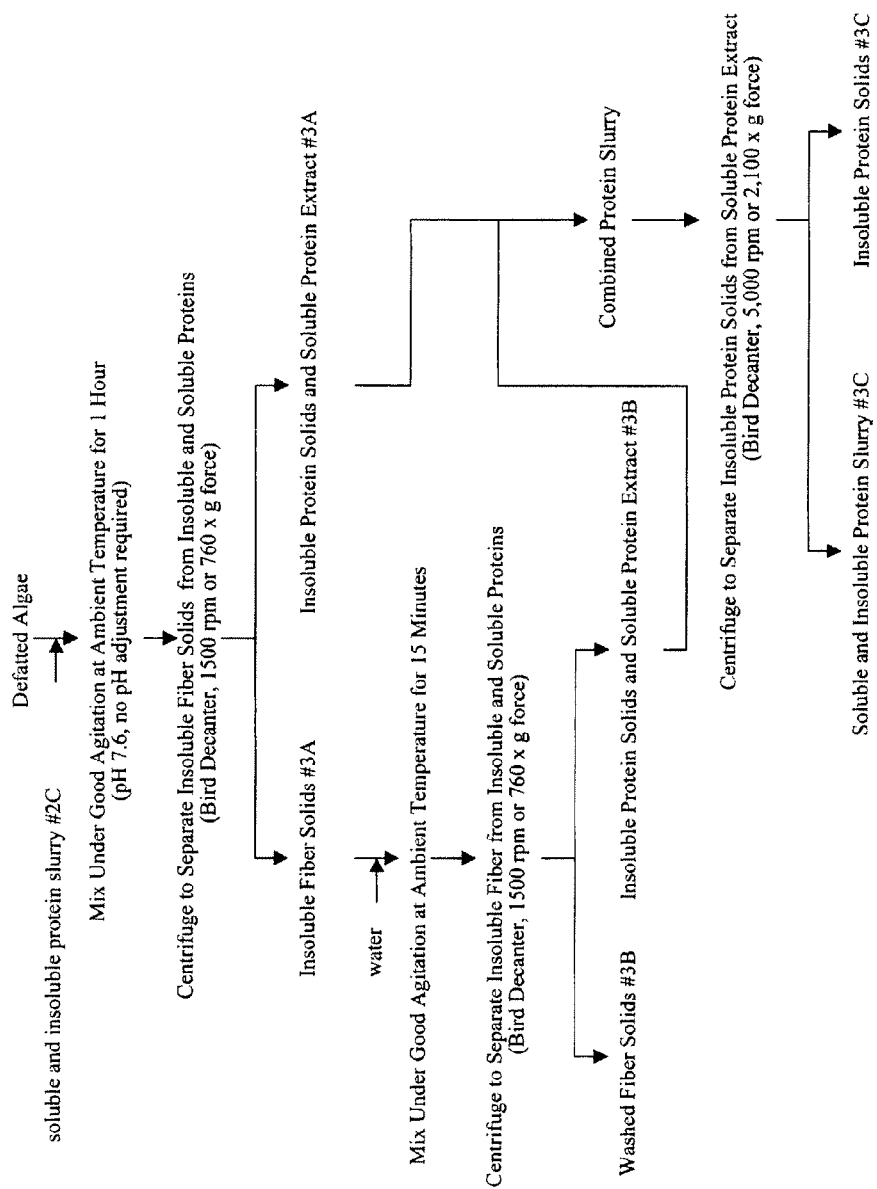
FIG. 22 is a schematic representation illustrating a second recycling of a protein fraction and a wet fiber removal process.
Figure 23:
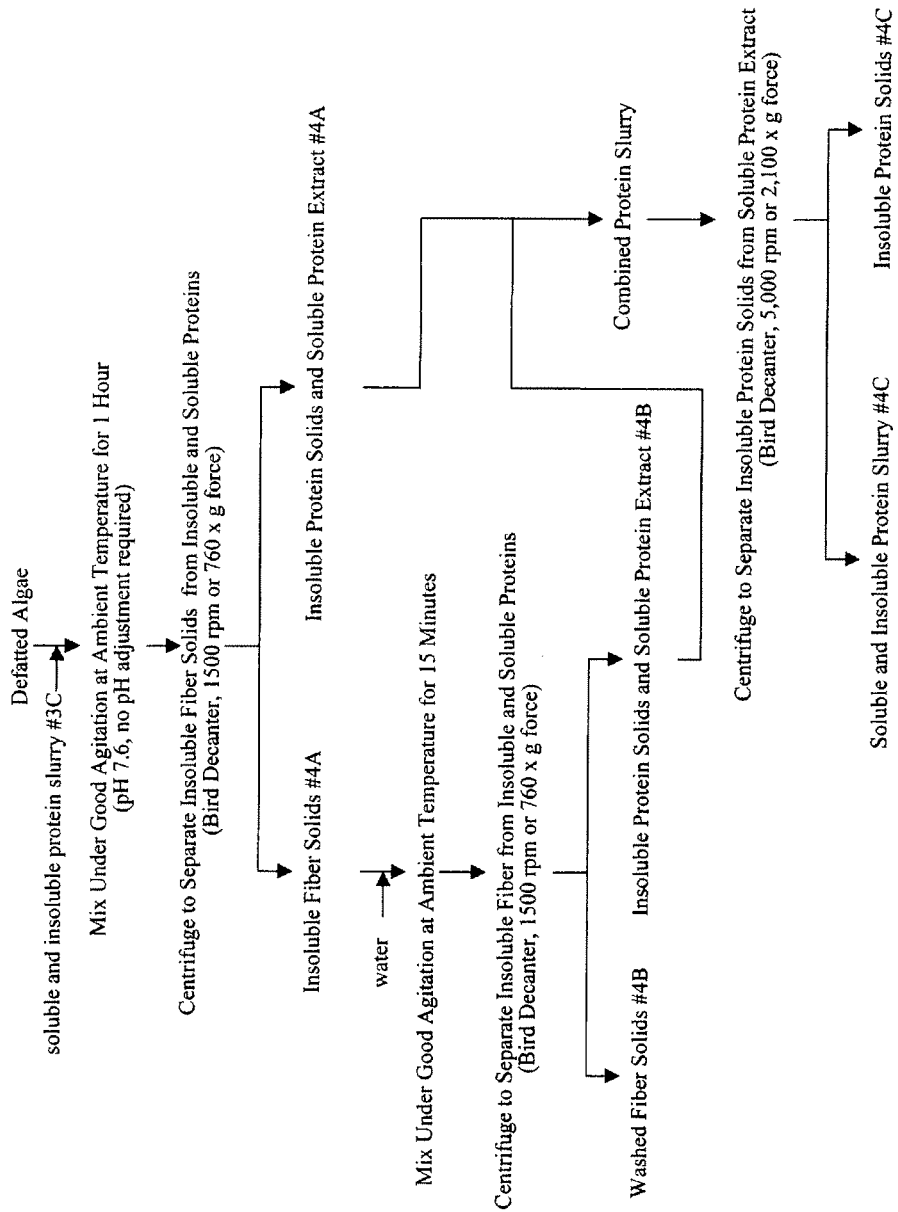
FIG. 23 is a schematic representation illustrating a third recycling of a protein fraction and a wet fiber removal process.
Figure 24:
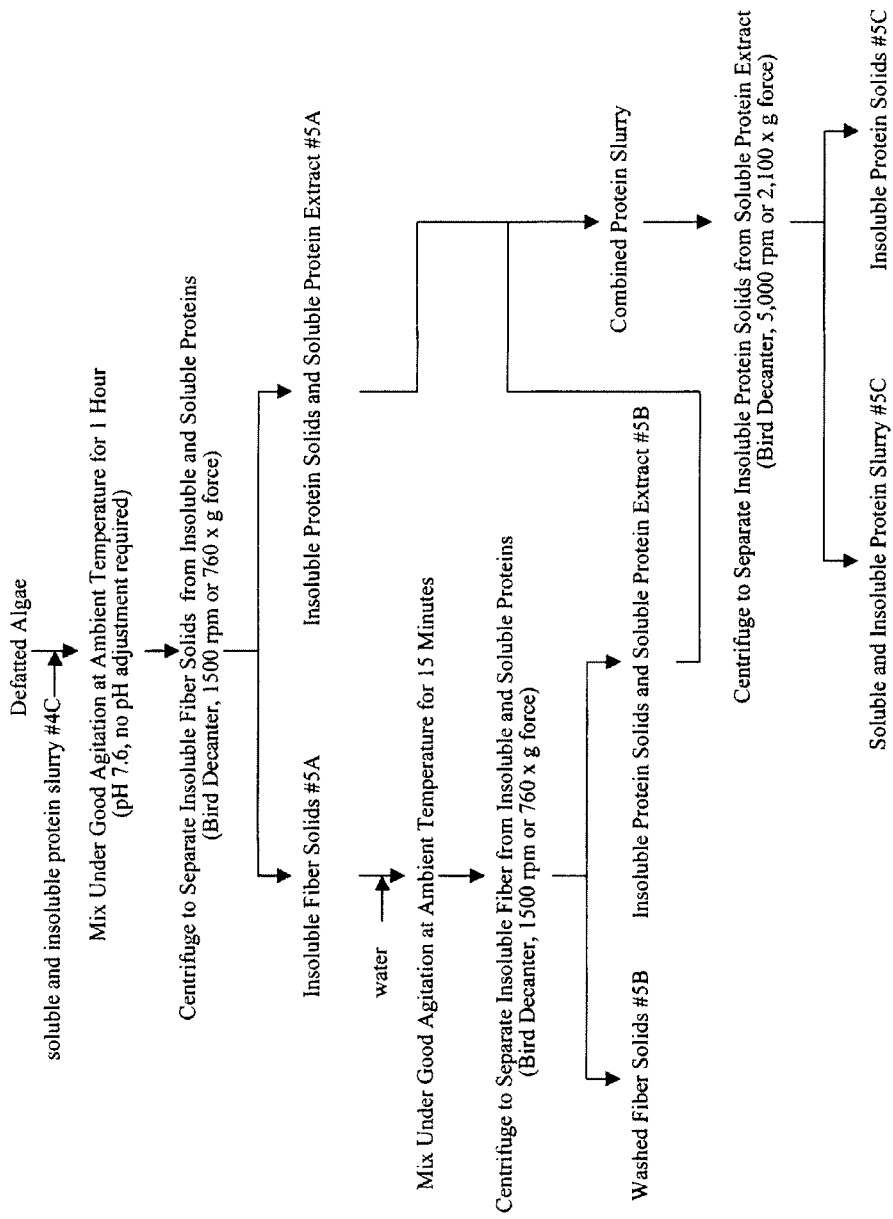
FIG. 24 is a schematic representation illustrating a fourth recycling of a protein fraction and a wet fiber removal process.

In another embodiment of the present disclosure, there is provided a process for the production of a protein isolate comprising a protein content of greater than 90% on a dry weight basis. In an embodiment, a general process for the production of a protein isolate and hydrolyzed proteins having a protein content greater than 90% is illustrated in FIGS. 11-12.

Accordingly, a process for the production of a protein isolate from macroalgae and/or microalgae is disclosed, comprising:
  removing fiber from the defatted or protein-enriched macroalgae and/or microalgae, comprising:
    i) mixing the macroalgae and/or microalgae with a mixing solvent to form a mixture;
      screening the mixture through a mesh screen of about 10 to about 200 US mesh size to remove fiber,
      optionally adjusting the pH of the mixture to a pH of about 7;
      optionally milling the mixture; and
      centrifuging the mixture to remove fiber,
      and forming a protein slurry;
    ii) centrifuging the protein slurry to form a protein precipitate and a soluble protein fraction;
    iii) filtering the soluble protein fraction; and
    iv) drying the soluble protein to form the protein isolate.

In an embodiment, the soluble protein fraction is obtained using the same process as described above.

It will be understood by a person skilled in the art that the steps of the process do not have to be followed exactly. For example, a person skilled in the art would recognize that the milling step could be performed before the screening step.

In an embodiment of the disclosure, the mixing solvent comprises water or a salt solution. In an embodiment, the salt solution comprises less than 5%, optionally about 3% to about 4%, or 3.5% by weight of salt in solution. In a further embodiment, the mixing solvent comprises water. In another embodiment, the ratio of macroalgae and/or microalgae to the mixing solvent is about 1:3 to about 1:20. In a further embodiment, the ratio is about 1:6 to about 1:10. In an embodiment, the ratio is about 1:6 to about 1:8.

In an embodiment, the soluble protein fraction is purified by ultrafiltration and diafiltration using a membrane filtration apparatus. In an embodiment, when ultrafiltration is utilized, the soluble protein fraction is heated to a temperature of about 1° C. to about 60° C., optionally 40° C. to about 55° C., before being passed through an ultrafiltration apparatus fitted with membranes to filter proteins larger than about 10,000 daltons, optionally about 30,000, or about 100,000 daltons. The filtered protein is recycled back to the feed tank while the liquid is discarded. The ultrafiltration process is continued until the amount of protein that has been filtered in the feed tank is equal to about 30% to about 40% of its initial weight of the soluble protein fraction.

In a further embodiment, when diafiltration is utilized, it is conducted at about 1° C. to about 60° C., optionally about 40° C. to about 55° C., using the diafiltration unit, which is fitted with the membranes to filter proteins larger than about 10,000 daltons, optionally about 30,000, or about 100,000 daltons. The original volume of soluble protein fraction in the feed tank is held constant by adding water to make up for the removed liquid. The filtered protein is recycled back to the feed tank. The amount of water added to maintain the original volume of protein solution is about 2 times the original volume of soluble protein fraction. For example, if 100 L of soluble protein fraction is used, 200 L of water is added to the soluble protein fraction in the feed tank during the cycle of diafiltration. The volume of the feed tank is kept constant at 100 L with the continued addition of water to the feed tank while the liquid is removed from the system through diafiltration.

In an embodiment, after the soluble protein fraction has been filtered, the filtered soluble protein is spray dried to form a high functional protein isolate comprising a protein content of greater than about 90% on a dry weight basis. It will be understood by a person skilled in the art that spray drying is the transformation of a feed from a fluid state into a dried form by spraying the feed into a circulating hot air medium. Generally, spray drying transforms the filtered protein into many droplets which are then exposed to a fast current of hot air. As a result of the very large surface area of the droplets the water in the protein evaporates almost instantaneously and the droplets are transformed into powdery dry protein particles. In an embodiment, the inlet temperature is about 180° C. to about 220° C. which is the temperature of the hot air entering the spray dryer chamber, the outlet temperature is about 75° C. to about 90° C., which is the temperature of the exhaust, and the feed temperature is about 40° C. to about 50° C. It will be understood by a person skilled in the art that the washed protein precipitate can be used as a protein isolate without drying. However, the dried protein isolate has a better shelf life as removal of the solvent, for example water, results in a more stable protein isolate.

In another embodiment of the present disclosure, there is provided a process for the production of a protein isolate which is subsequently modified or hydrolyzed to form a high functional protein isolate or a mixture of hydrolyzed proteins, peptides and amino acids comprising a protein content of greater than 90% on a dry weight basis.

Accordingly, in an embodiment of the present disclosure, a process for the production of a protein isolate from macroalgae and/or microalgae is disclosed, comprising:
  removing fiber from the defatted or protein-enriched macroalgae and/or microalgae, comprising:
    i) mixing the macroalgae and/or microalgae with a mixing solvent to form a mixture;
      optionally screening the mixture through a mesh screen of about 10 to about 200 US mesh size to remove fiber,
      optionally adjusting the pH of the mixture to a pH of about 7;
      optionally milling the mixture; and
      centrifuging the mixture to remove fiber,
      and forming a protein slurry;
    ii) centrifuging the protein slurry to form a protein precipitate and a soluble protein fraction;
    iii) mixing the protein precipitate with water to form a protein precipitate mixture and optionally adjusting the pH of the mixture to a pH of about 3 to about 7;
    iv) adding cellulase complex to the protein precipitate mixture to hydrolyze residual fiber;
    v) washing the protein precipitate with an extraction solvent and centrifuging to form a protein isolate.

It will be understood by a person skilled in the art that the steps of the process do not have to be followed exactly. For example, a person skilled in the art would recognize that the milling step could be performed before the screening step.

In another embodiment of the disclosure, the mixing solvent comprises water or a salt solution. In an embodiment, the salt solution comprises less than 5%, optionally about 3% to about 4%, or 3.5% by weight of salt in solution. In a further embodiment, the mixing solvent comprises water. In another embodiment, the ratio of macroalgae and/or microalgae to the mixing solvent is about 1:3 to about 1:20. In a further embodiment, the ratio is about 1:6 to about 1:10. In an embodiment, the ratio is about 1:6 to about 1:8.

In a further embodiment, the mixture is wet screened resulting in a separation of the fiber from the mixture which contains the protein. In another embodiment of the disclosure, the mesh screen comprises a US mesh screen of size about 20 to about 200 mesh. In an embodiment, the mesh screen is of size 40 US mesh size. In a further embodiment, the mesh screen is a vibratory screen. The mesh screen prevents the fiber from passing through, while the protein in the mixture passes through the screen, resulting in a separation of the fiber from the protein. This results in a mixture of protein which passes through the screen and a fiber fraction which is trapped by the screen. In an embodiment, the fiber fraction is dried and can be used in dietary fiber products. In an embodiment, some protein and carbohydrates are present in the fiber fraction.

In another embodiment, the pH of the mixture is optionally adjusted to about 7 with the addition of aqueous sodium hydroxide. In a further embodiment, the aqueous sodium hydroxide is a solution of about 1% to about 40%, optionally about 5% to about 30%, by weight of sodium hydroxide in water.

In another embodiment, the mixture is optionally milled using a wet milling process. In an embodiment, the wet milling of the mixture results in thorough mixing of the macroalgae and/or microalgae with the mixing solvent.

In another embodiment of the present disclosure, the mixture is centrifuged using a decanting centrifuge. In an embodiment, the mixture is centrifuged with a decanting centrifuge at a speed of about 1000 rpm to about 2000 rpm. In another embodiment, the speed is about 1500 rpm.

In another embodiment, the protein slurry is centrifuged using a disc stack centrifuge to separate insoluble proteins from soluble proteins, forming a protein precipitate and a soluble protein fraction. In an embodiment, the soluble protein fraction is filtered as described above. In an embodiment, the disc centrifuge operates continuously at a speed of about 6500 rpm to about 8500 rpm at a temperature of about 1° C. to about 60° C., optionally about 20° C. to about 40° C., or optionally at about 20° C. to about 25° C.

In an embodiment of the disclosure, the precipitated protein is mixed with water and its pH optionally adjusted for the addition of cellulase complex, in a similar manner as described above. This additional enzymatic step hydrolyzes residual fiber and allows the removal of fiber from the protein precipitate.

In another embodiment, after treatment with the cellulase complex, the protein precipitate is washed at least once with an extraction solvent to remove water-soluble sugar compounds as a result of the fiber hydrolyzation by the cellulase complex. In an embodiment, the extraction solvent is water. In an embodiment, the protein precipitate mixture is washed at least twice with the extraction solvent. In an embodiment, the ratio of extraction solvent to the precipitated protein is about 10:1 to about 1:1, optionally about 4:1 to about 2:1. The mixture is then further centrifuged to obtain a protein precipitate that has been further purified.

In an embodiment, the further purified protein precipitate is then subjected to high pressure jet cooking to obtain a high functional protein isolate having a protein content of greater than about 90% on a dry weight basis. In an embodiment, the jet cooking of the protein isolate occurs at a temperature of about 90° C. to about 120° C. for about 1 second to about 2 minutes, optionally about 3 seconds to about 30 seconds. As will be understood by a person skilled in the art, jet cooking involves the injection of steam into the purified protein, and results in the pasteurization of the protein and improves the functional properties of the protein isolate.

In another embodiment, the further purified protein precipitate is hydrolyzed using proteases to form a hydrolyzed protein extract containing hydrolyzed proteins, peptides and amino acids having a protein content of greater than about 90% on a dry weight basis. In an embodiment, the proteases are, for example, Alcalase® and Flavourzyme®. Alcalase® and Flavourzyme® were obtained from Novozymes North America, Inc., Franklinton, N.C. USA. This step hydrolyzes the protein in the protein precipitate into smaller peptides and amino acids, which are soluble in nutritional drinks and are easily adsorbed. In an embodiment, the purified protein precipitate is mixed with water to form a protein slurry, which is optionally followed by pH adjustment to a pH of about 6.0 to about 10.0, optionally about 7.5 to about 8.5. In an embodiment, the Alcalase® is added in a ratio of about 0.5% based on the dry weight of the protein slurry. In a further embodiment, the temperature is adjusted to about 20° C. to about 65° C., optionally about 50° C. to about 60° C., or about 60° C., for about 1 to about 4 hours. The hydrolyzed protein slurry is then cooled to about 30° C. to about 50° C., or about 40° C. to about 50° C., or about 50° C. The pH of the mixture is then adjusted to a pH of about 5.0 to about 7.0, or about 6.0 to about 7.0, or about 6.5, and a protease to form a hydrolyzed protein extract, such as Flavourzyme®, is then added to the mixture. In an embodiment, the protease to form a hydrolyzed protein extract, such as Flavourzyme®, is added in a ratio of about 0.5% based on the dry weight of the protein slurry. In a further embodiment, the mixture is then heated to a temperature of about 20° C. to about 60° C., optionally about 40° C. to about 60° C., or about 45° C. to about 55° C., for about 1 to about 4 hours. The hydrolyzed protein mixture is then centrifuged to separate the hydrolyzed protein extract from the insoluble solids. The soluble hydrolyzed protein extract is then spray dried as described above, while the extract from the centrifugation is added to the soluble protein fraction as described above.

In another embodiment of the disclosure, there is a provided a process for the production of a protein concentrate from a macroalgae and/or microalgaeas shown in FIGS. 13-19, comprising:
i) mixing the macroalgae and/or microalgae with a mixing solvent to form a mixture;
ii) optionally adjusting the pH of the mixture to a pH of about 2.0 to about 10.0;
iii) separating fiber from the mixture to form a protein slurry, wherein the protein slurry comprises a soluble protein fraction and an insoluble protein fraction;
iv) optionally repeating steps i)-iii) by mixing the protein slurry with additional partially defatted, fully defatted or protein-enriched algae;
v) mixing the protein slurry with an extraction solvent to form an extract and a washed insoluble protein fraction;
vi) separating the extract from the washed insoluble protein fraction;
vii) optionally repeating steps v) and vi) at least once; and
viii) desolventizing the washed insoluble protein fraction to form a protein concentrate.

In another embodiment of the disclosure, the ratio of macroalgae and/or microalgae to mixing solvent is about 1:3 to about 1:30 (w/w). In another embodiment, the ratio of macroalgae and/or microalgae to solvent is about 1:5 to about 1:20 (w/w). In a further embodiment, the ratio is about 1:6 to about 1:12 (w/w). In an embodiment, the ratio is about 1:8 to about 1:10 (w/w).

In a further embodiment of the disclosure, the mixing solvent comprises water or an aqueous solution comprising a polysaccharide, a salt or an alcohol. In an embodiment, the mixing solvent is water. In another embodiment, the polysaccharide is guar gum.

In an embodiment, the pH of the protein slurry is adjusted to a pH of about 6.5 to about 10.0. In a further embodiment, the pH of the protein slurry is adjusted to a pH of about 7.0 to about 9.0.

In an embodiment, the mixture is centrifuged to separate the fiber from mixture and form the protein slurry. In an embodiment, the mixture is centrifuged at a speed of about 1,000 rpm to about 2,000 rpm. In a further embodiment, the mixture is centrifuged at a speed of about 1,400 to about 1,600 rpm. In an embodiment, the mixture is centrifuged using a decanter centrifuge.

The centrifugation of the mixture results in three layers: i) an insoluble fiber layer and a protein slurry on top of the fiber, which was comprised of ii) an insoluble protein fraction and iii) a soluble protein fraction. Separation of the top and middle layers (the soluble protein extract and the insoluble fine protein fraction) from the bottom layer (coarse fiber solids), resulted in the protein slurry with fiber removed. In an embodiment, the bird decanter was operated at a low pool depth with a bowl speed of between about 1,000 rpm and about 2,000 rpm, optionally 1,400 to about 1,600 rpm, suitably about 1,500 rpm. It was determined that when the speed of the centrifugation is too high, for example at 5,000 rpm, the insoluble protein fraction settles with the fiber. If the speed of the centrifugation is too low, fiber will remain in the protein slurry. Accordingly, in an embodiment, when the speed of the centrifugation is between about 1,000 rpm and about 2,000 rpm, optionally 1,400 to about 1,600 rpm, suitably about 1,500 rpm, the fiber in the mixture is separated from both the soluble and insoluble protein.

In another embodiment of the disclosure, mixing the protein slurry with additional macroalgae and/or microalgae repeated at least once. In a further embodiment, mixing the protein slurry with additional macroalgae and/or microalgae is repeated at least two to seven times. In an embodiment, recycling the protein slurry with additional macroalgae and/or microalgae increases the solid content of the algae being processed, and accordingly, reduces the overall processing volume.

In an embodiment of the disclosure, the extraction solvent comprises water, methanol, ethanol, isopropanol, or mixtures thereof. In an embodiment, the extraction solvent comprises ethanol. In another embodiment, the extraction solvent comprises at least about 50% ethanol. In an embodiment, the extraction solvent comprises at least about 70% ethanol. In a further embodiment, the extraction solvent comprises at least about 90% ethanol.

In a further embodiment, the extract is separated from the washed insoluble protein fraction using centrifugation, vacuum filtration, pressure filtration, decantation or gravity draining. In an embodiment, the extract is separated from the washed insoluble protein fraction using centrifugation.

In another embodiment of the disclosure, wherein steps iv) and v) are repeated at least twice.

In a further embodiment, the process further comprises the step of drying the washed insoluble protein fraction to form the protein concentrate. In an embodiment, the protein concentrate is dried in a vacuum dryer, fluidized bed dryer, hot air dryer ring dryer or spray dryer.

In an embodiment, the protein concentrate comprises a protein content of about 30% to about 90% on a dry weight basis.

In another embodiment of the disclosure, there is also provided a process for the production of a protein isolate from a partially defatted, fully defatted or protein enriched algae, comprising:
  i) mixing the macroalgae and/or microalgae with alkaline water to form a mixture;
  ii) optionally adjusting the pH of the mixture to a pH of about 6.0 to about 10.0;
  iii) separating fiber from the mixture to form a first protein slurry, wherein the first protein slurry comprises a soluble protein fraction and an insoluble protein fraction;
  iv) separating the first protein slurry to form a protein solids fraction and a soluble protein fraction;
  v) mixing the protein solids fraction with water to form a second protein slurry;
  vi) separating the second protein slurry to form a second protein solids fraction and a second soluble protein fraction;
  vii) optionally repeating steps v) and vi) at least once;
  viii) separating the soluble protein fractions to form a clarified soluble protein fraction and a residual insoluble protein fraction;
  ix) optionally adjusting the pH of the clarified soluble protein fraction to a pH of about 7;
  x) separating the clarified soluble protein fraction, optionally by filtering the clarified soluble protein fraction by membrane filtration; and
  xi) optionally drying the clarified soluble protein fraction.

In another embodiment of the disclosure, the ratio of macroalgae and/or microalgae to alkaline water is about 1:3 to about 1:30 (w/w). In another embodiment, the ratio of macroalgae and/or microalgae to alkaline water is about 1:5 to about 1:20 (w/w). In a further embodiment, the ratio is about 1:6 to about 1:12 (w/w). In an embodiment, the ratio is about 1:8 to about 1:10 (w/w).

In an embodiment of the disclosure, the pH of the alkaline water is about 7 to about 12. In another embodiment, the pH of the first protein slurry is adjusted to about 8.0 to about 9.5. In a further embodiment, the pH of the first protein slurry is adjusted to about 8.5 to about 9.0.

In an embodiment, the mixture is centrifuged to separate the fiber from the protein slurry and form the protein extract. In an embodiment, the mixture is centrifuged at a speed of about 1,000 rpm to about 2,000 rpm. In a further embodiment, the mixture is centrifuged at a speed of about 1,400 to about 1,600 rpm. In an embodiment, the mixture is centrifuged using a decanter centrifuge.

In another embodiment, the first protein slurry is centrifuged to separate the protein solids fraction from the soluble protein fraction. In a further embodiment, the first protein slurry is centrifuged at a speed of about 4,000 rpm to about 8,500 rpm. In a further embodiment, the first protein slurry is centrifuged at a speed of about 5,000 to about 8,500 rpm.

In another embodiment of the disclosure, the ratio of the protein solids fraction to water is about 1.0:0.5 to about 1.0:3.0 (w/w). In a further embodiment, the ratio of the protein solids fraction to water is about 1.0:1.0 to about 1.0:2.0 (w/w).

In an embodiment, the soluble protein fractions are centrifuged to form the clarified soluble protein fraction and the residual insoluble protein fraction. In an embodiment, the soluble protein fractions are centrifuged using a disc stack centrifuge at a speed of about 7,000 rpm to about 10,000 rpm.

In a further embodiment, the soluble protein fractions are centrifuged using a disc stack centrifuge at a speed of about 8,400 rpm to about 8,600 rpm.

In another embodiment of the disclosure, the pH of the clarified soluble protein fraction is adjusted with alkali. In a further embodiment, the pH of the clarified soluble protein fraction is adjusted with sodium hydroxide.

In an embodiment, the clarified soluble protein fraction is filtered using an ultrafiltration apparatus. In a further embodiment, the ultrafiltration apparatus comprises a membrane to filter proteins larger than about 10,000 daltons. In another embodiment, the separation of the clarified soluble protein fraction is accomplished by adjusting the pH of the solution to the isoelectric point of the proteins (about pH of 4.5), and consequently, the proteins are precipitated out of solution. In another embodiment, the proteins are cooked to precipitate the proteins from solution.

In another embodiment of the disclosure, the process further comprises the step of filtering the clarified soluble protein fraction using a diafiltration apparatus.

In another embodiment, the clarified soluble protein fraction is dried in a vacuum dryer, fluidized bed dryer, freeze dryer, ring dryer or spray dryer to form the protein isolate.

In another embodiment of the disclosure, the protein concentrate comprises a protein content of greater than about 90% on a dry weight basis.

In another embodiment of the disclosure, there is also provided a process for the production of a hydrolyzed protein concentrate from a partially defatted, fully defatted or protein-enriched algae, comprising:

i) mixing the macroalgae and/or microalgae with water to form a mixture;
ii) optionally adjusting the pH of the mixture to a pH of about 6.0 to about 10.0;
iii) separating the mixture to remove fiber from the mixture and form a first protein slurry, wherein the first protein slurry comprises a soluble protein fraction and an insoluble protein fraction;
iv) optionally adjusting the pH of the first protein slurry to a pH of about 7.0;
v) separating the first protein slurry to form a first protein solids fraction and a first soluble protein fraction;
vi) mixing the first protein solids fraction with water to form a second protein slurry;
vii) separating the second protein slurry to form a second protein solids fraction and a second soluble protein fraction;
viii) mixing the second protein solids fraction with water to form a third protein slurry;
ix) adjusting the pH of the third protein slurry to a pH of about 7.0 to about 9.0;
x) mixing the third protein slurry with at least one protease to form a hydrolyzed protein extract;
xi) separating the hydrolyzed protein extract from the third protein slurry to form the hydrolyzed protein concentrate.

In another embodiment of the disclosure, the ratio of macroalgae and/or microalgae to water is about 1:3 to about 1:30 (w/w). In another embodiment, the ratio of macroalgae and/or microalgae to water is about 1:5 to about 1:20 (w/w). In a further embodiment, the ratio is about 1:6 to about 1:12 (w/w). In an embodiment, the ratio is about 1:8 to about 1:10 (w/w).

In another embodiment, the pH of the mixture is adjusted to about 8.0 to about 9.0. In a further embodiment, the pH of the mixture is adjusted to about 8.5 to about 9.0.

In an embodiment, the mixture is centrifuged to separate the fiber from the protein slurry and form the protein extract. In an embodiment, the mixture is centrifuged at a speed of about 1,000 rpm to about 2,000 rpm. In a further embodiment, the mixture is centrifuged at a speed of about 1,400 to about 1,600 rpm. In an embodiment, the mixture is centrifuged using a decanter centrifuge.

In another embodiment, the first protein slurry is centrifuged to separate the protein solids fraction from the soluble protein fraction. In a further embodiment, the first protein slurry is centrifuged at a speed of about 4,000 rpm to about 8,000 rpm. In a further embodiment, the first protein slurry is centrifuged at a speed of about 5,000 to about 8,500 rpm.

In another embodiment, the ratio of the first and second protein solids fraction to water is about 1.0:0.5 to about 1.0:3.0 (w/w). In a further embodiment, the ratio of the first and second protein solids fraction to water is about 1.0:1.0 to about 1.0:2.0 (w/w).

In another embodiment of the disclosure, the pH of the third protein slurry is adjusted to about 8.0 to about 8.5.

In an embodiment of the disclosure, the ratio of the third protein slurry to the protease is about 100:1 to about 5000:1 (w/w).

In an embodiment of the disclosure, the third protein slurry is mixed with a protease at a temperature of about 50° C. to about 70° C. In another embodiment, the third protein slurry is mixed with a protease at a temperature of about 55 to about 65° C.

In another embodiment, the at least one protease comprises a protease from *Bacillus Licheniformis*.

In a further embodiment, the process further comprises the step of mixing the third protein slurry with a second protease.

In an embodiment, the ratio of the third protein slurry to the second protease is about 100:1 to about 5000:1 (w/w).

In another embodiment, the third protein slurry is mixed with the second protease at a temperature of about 40° C. to about 60° C. In an embodiment, the third protein slurry is mixed with the second protease at a temperature of about 45° C. to about 55° C.

In a further embodiment, the second protease comprises a fungal protease/peptidase complex from *Aspergillus oryzae*.

In an embodiment, the hydrolyzed protein extract is separated using a centrifuge. In a further embodiment, the hydrolyzed protein extract is separated using a decanter centrifuge at a speed of about 3,800 to about 5,200 rpm.

In another embodiment, the clarified soluble protein fraction is dried in a vacuum dryer, fluidized bed dryer, ring dryer or spray dryer to form the protein isolate.

In a further embodiment, the hydrolyzed protein concentrate comprises a protein content of greater than about 30% on a dry weight basis.

In an embodiment, the use of an extraction solvent, such as ethanol, leads to a protein concentrate or protein isolate having superior organoleptic properties, as well as superior protein solubility properties, which therefore possesses better functional properties. In an embodiment, the use of an extraction solvent, such as ethanol, results in the protein concentrates containing fewer impurities. Consequently, the protein concentrates are generally of higher quality and have better functional properties.

In another embodiment of the disclosure, there is also provided a process for the production of a protein isolate from macroalgae and/or microalgae as shown in FIGS. 20-25, comprising:

i) mixing the macroalgae and/or microalgae with a blending solvent, optionally water or alkaline water, to form a mixture and optionally treating the mixture with phytase at a temperature and a pH suitable for phytase activity;

ii) optionally adjusting the pH of the mixture to a pH of about 7.0 to about 10.0;

iii) separating fiber from the mixture to form a first protein slurry, wherein the first protein slurry comprises a soluble protein fraction and an insoluble protein fraction;

iv) separating the first protein slurry to form a protein solids fraction and a soluble protein fraction;

v) optionally mixing the protein solids fraction with a second blending solvent, optionally water, to form a second protein slurry;

vi) optionally separating the second protein slurry to form a second protein solids fraction and a second soluble protein fraction;

vii) optionally repeating steps v) and vi) at least once;

viii) separating the soluble protein fractions to form a clarified soluble protein fraction and a residual insoluble protein fraction;

ix) optionally adjusting the pH of the clarified soluble protein fraction to a pH of about 6 to about 9;

x) separating the clarified soluble protein fraction, optionally by filtering the clarified soluble protein fraction by membrane filtration; and xi) optionally drying the clarified soluble protein fraction.

In another embodiment of the disclosure, the ratio of macroalgae and/or microalgae to water or alkaline water is about 1:4 to about 1:30 (w/w). In another embodiment, the ratio of macroalgae and/or microalgae to water or alkaline water is about 1:5 to about 1:20 (w/w). In a further embodiment, the ratio is about 1:6 to about 1:12 (w/w). In an embodiment, the ratio is about 1:8 to about 1:10 (w/w).

In an embodiment of the disclosure, the pH of the alkaline water is about 7 to about 12. In another embodiment, the pH of the first protein slurry is adjusted to about 8.0 to about 9.5. In a further embodiment, the pH of the first protein slurry is adjusted to about 8.5 to about 9.0.

In another embodiment of the disclosure, the mixture is separated by centrifugation, gravity sedimentation, a gravity table or hydrocyclone to separate the fiber from the mixture and form the protein slurry. In a further embodiment, the mixture is separated by centrifugation to separate the fiber from the mixture and form the protein slurry. In an embodiment, the mixture is centrifuged at a speed of about 1,000 rpm to about 2,000 rpm. In a further embodiment, the mixture is centrifuged at a speed of about 1,400 to about 1,600 rpm. In an embodiment, the mixture is centrifuged using a decanter centrifuge.

In another embodiment, the first protein slurry is centrifuged, optionally using a disc stack centrifuge, to separate the protein solids fraction from the soluble protein fraction. In a further embodiment, the first protein slurry is centrifuged at a speed of about 4,000 rpm to about 8,000 rpm. In a further embodiment, the first protein slurry is centrifuged at a speed of about 6,500 to about 7,500 rpm.

In another embodiment of the disclosure, the ratio of the protein solids fraction to water is about 1.0:0.5 to about 1.0:3.0 (w/w). In a further embodiment, the ratio of the protein solids fraction to water is about 1.0:1.0 to about 1.0:2.0 (w/w).

In an embodiment, the soluble protein fractions are centrifuged to form the clarified soluble protein fraction and the residual insoluble protein fraction. In an embodiment, the soluble protein fractions are centrifuged using a disc stack centrifuge at a speed of about 7,000 rpm to about 10,000 rpm. In a further embodiment, the soluble protein fractions are centrifuged using a disc stack centrifuge at a speed of about 7,500 rpm to about 8,500 rpm.

In another embodiment of the disclosure, the pH of the clarified soluble protein fraction is adjusted with alkali. In a further embodiment, the pH of the clarified soluble protein fraction is adjusted with sodium hydroxide.

In an embodiment, the clarified soluble protein fraction is filtered using an ultrafiltration apparatus. In a further embodiment, the ultrafiltration apparatus comprises a membrane to filter proteins larger than about 10,000 daltons.

In another embodiment of the disclosure, the process further comprises the step of filtering the clarified soluble protein fraction using a diafiltration apparatus.

In another embodiment, the clarified soluble protein fraction is dried in a vacuum dryer, fluidized bed dryer, ring dryer or spray dryer to form the protein isolate.

In another embodiment, the protein isolate comprises a hydrolyzed protein isolate. In another embodiment, the protein isolate is hydrolyzed to produce peptides and free amino acids. In another embodiment, the hydrolyzed protein isolate comprises peptides and/or free amino acids.

In another embodiment of the disclosure, the protein isolate comprises a protein content of greater than about 90% on a dry weight basis.

Figure 25:
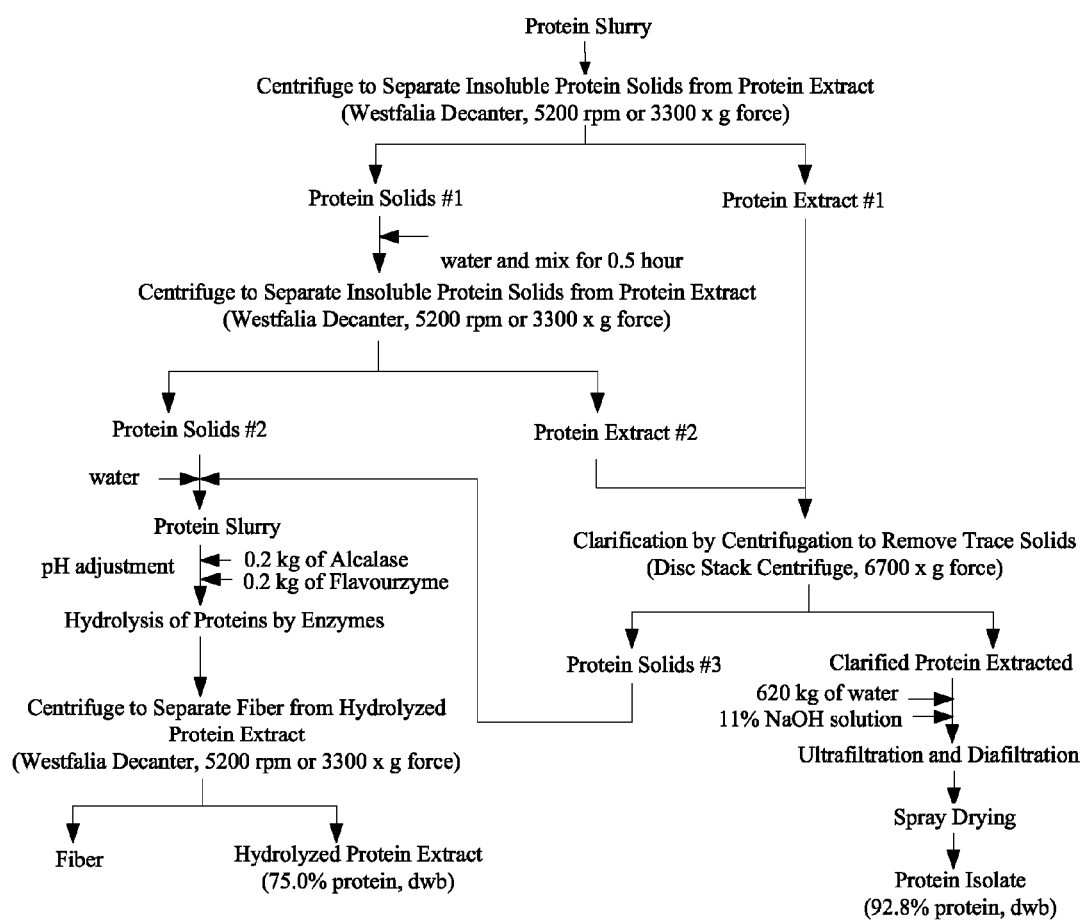
FIG. 25 is a schematic representation illustrating a preparation of a protein isolate and a hydrolyzed protein extract.
Figure 26:
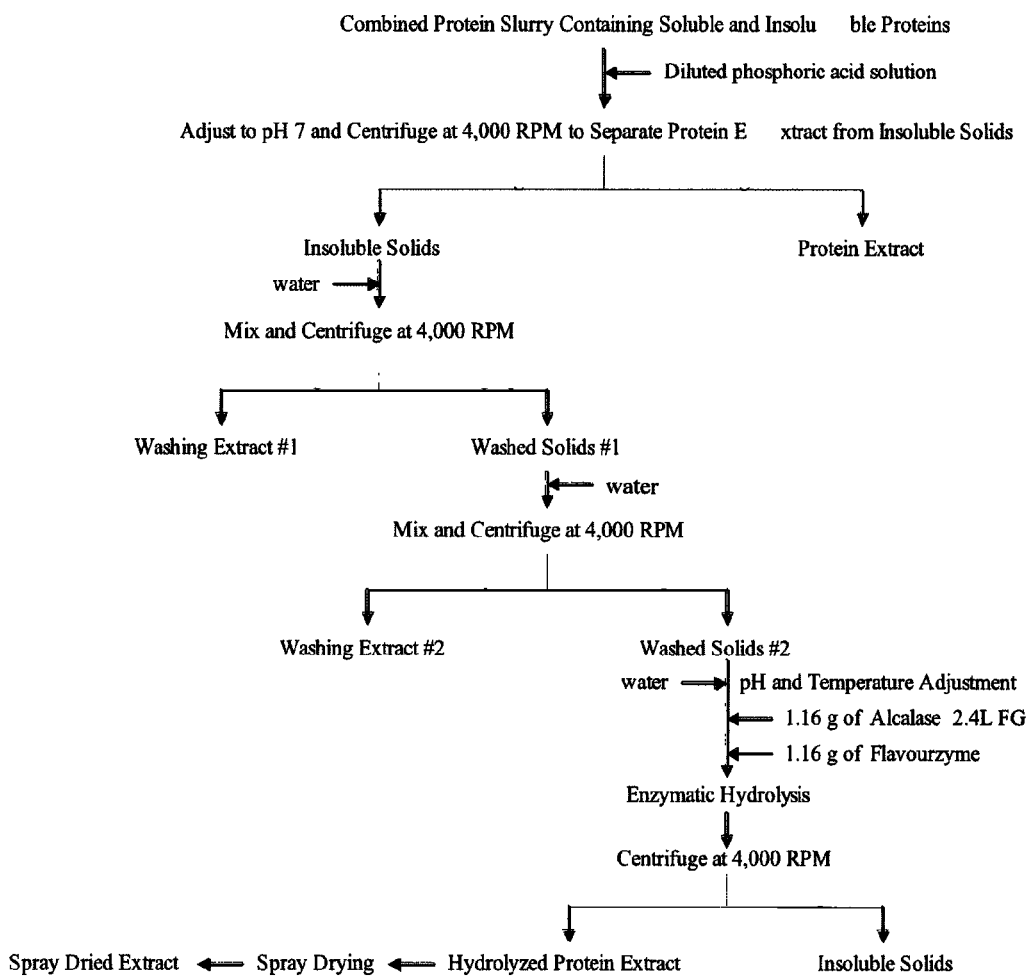
FIG. 26 is a schematic representation illustrating a preparation of a hydrolyzed protein extract.
Figure 27:
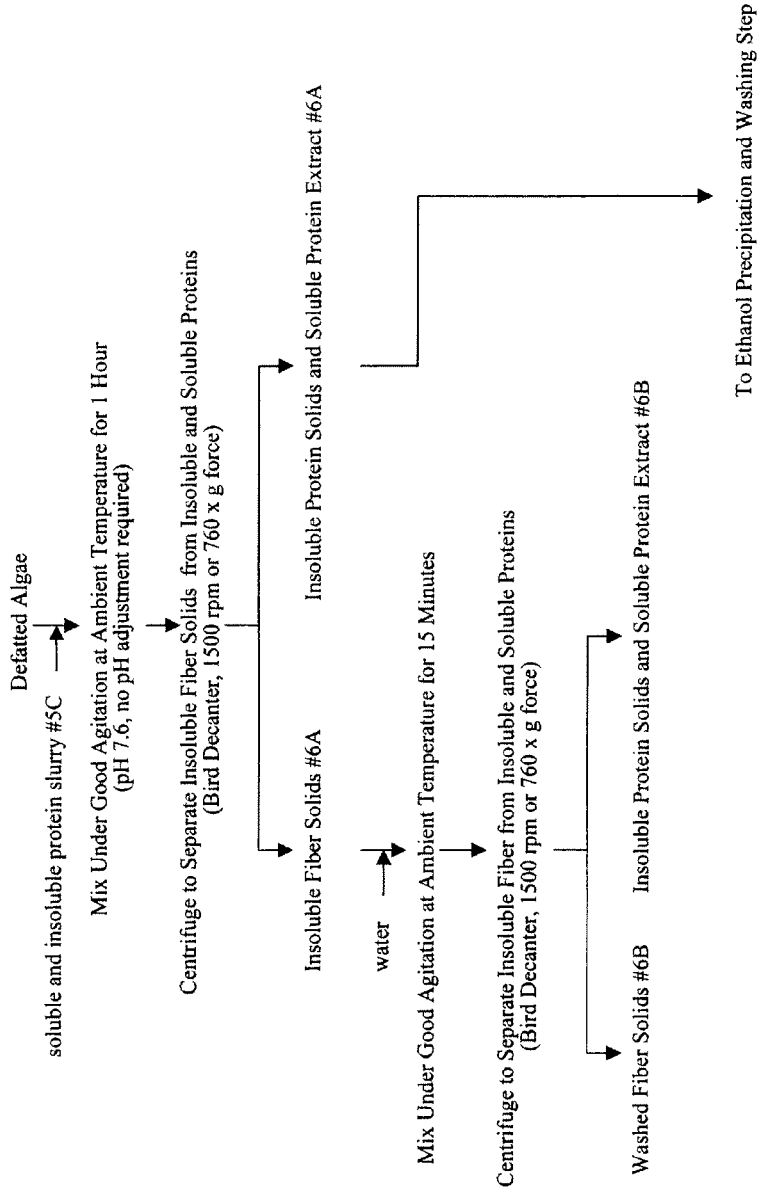
FIG. 27 is a schematic representation illustrating a fifth recycling of a protein fraction and a wet fiber removal process.
Figure 28:
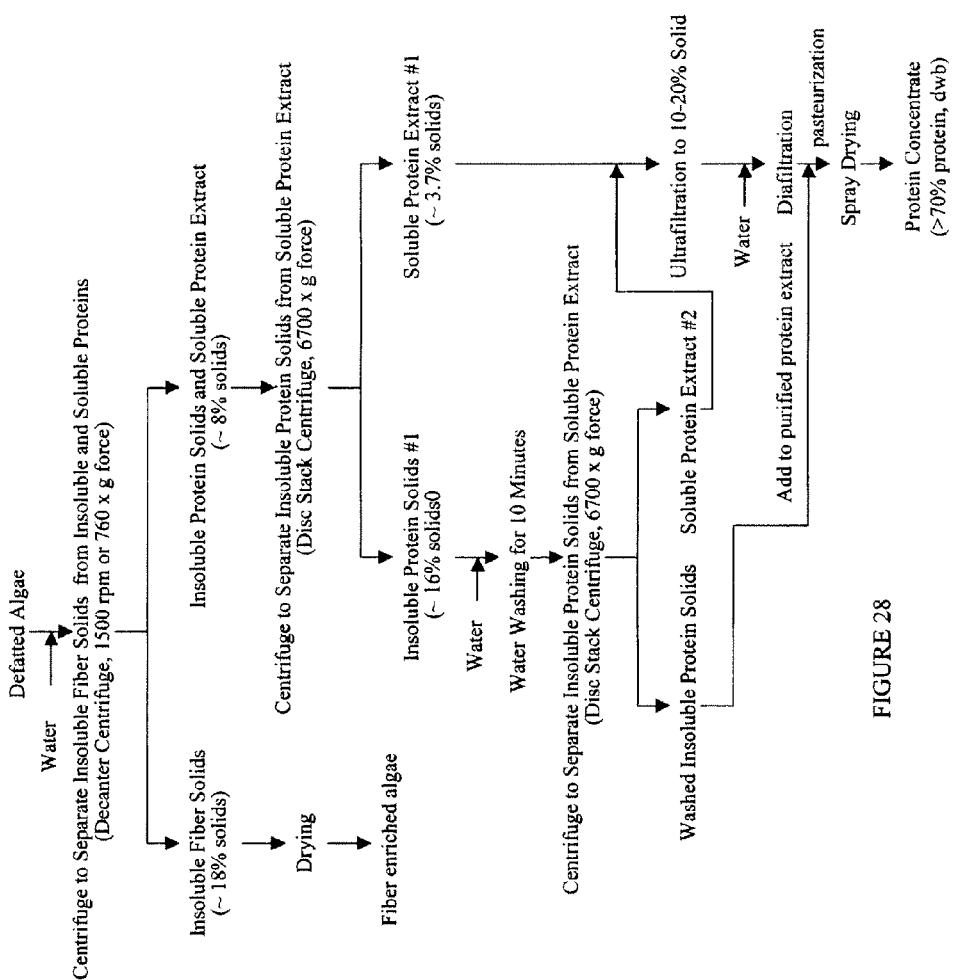
FIG. 28 is a schematic representation in a first embodiment illustrating a preparation of a protein concentrate.
Figure 29:
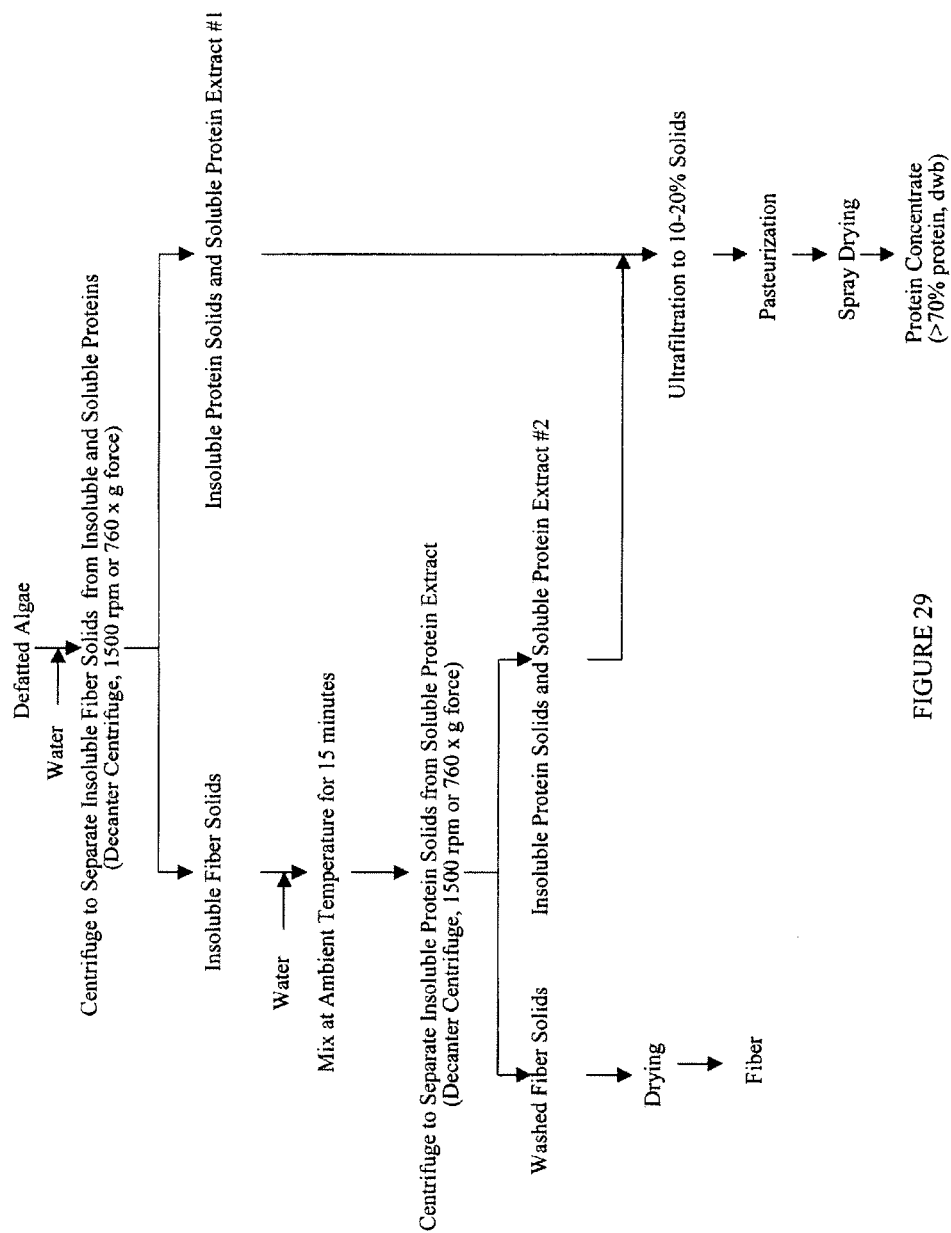
FIG. 29 is a schematic representation in a second embodiment illustrating a preparation of a protein concentrate.
Figure 30:
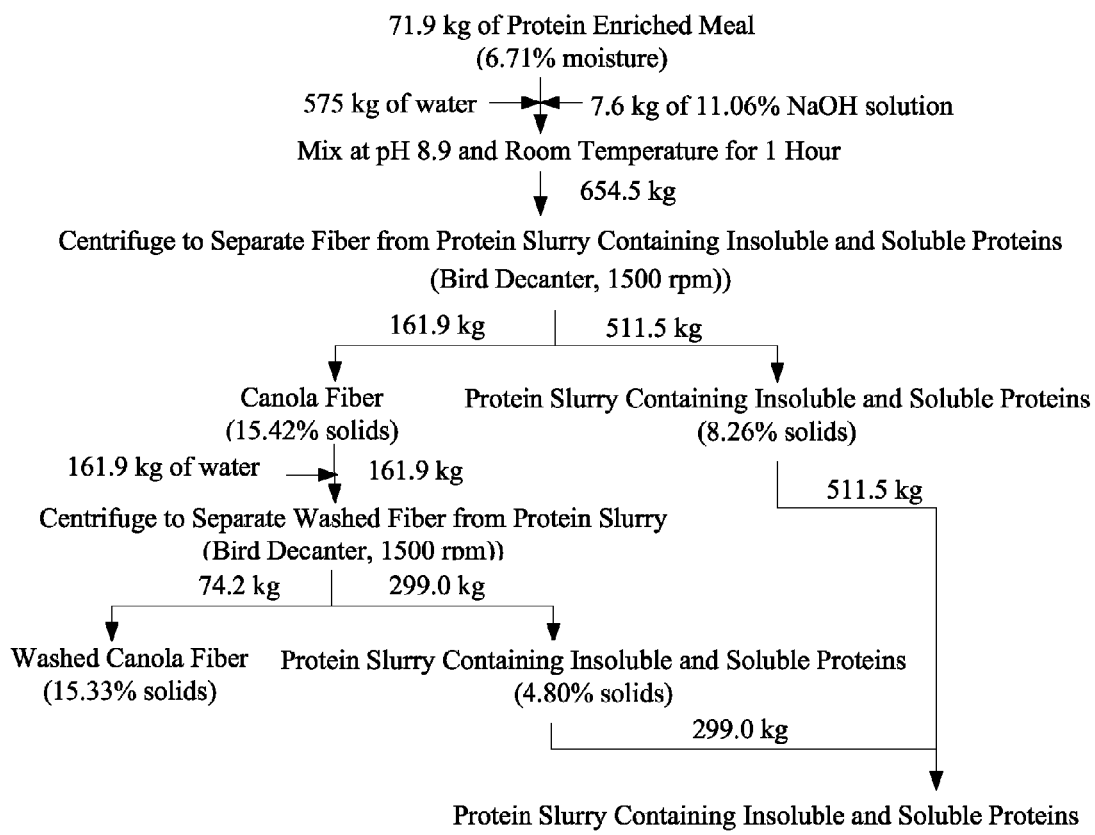
FIG. 30 is a schematic representation in a first embodiment illustrating a separation and removal of fiber from a protein slurry containing insoluble and soluble proteins.
Figure 31:
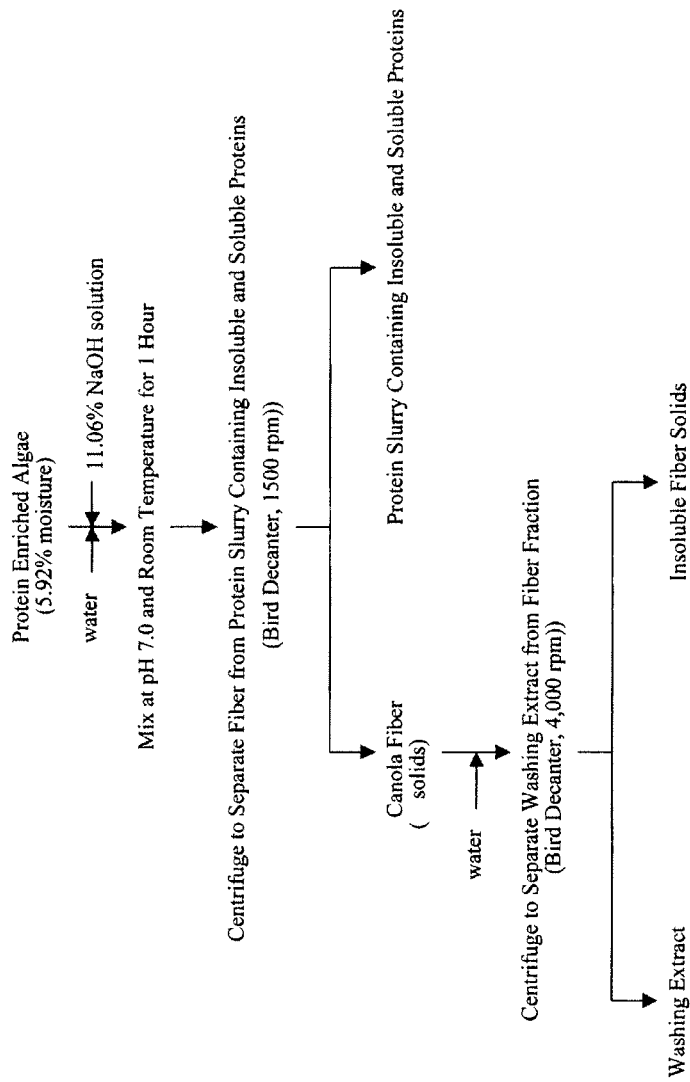
FIG. 31 is a schematic representation in a second embodiment illustrating a separation and removal of fiber from a protein slurry containing insoluble and soluble proteins.

In another embodiment of the disclosure, there is also provided a process for the production of a hydrolyzed protein concentrate from macroalgae and/or microalgae as shown in FIGS. 25-26, comprising:

i) mixing the macroalgae and/or microalgae with a blending solvent, optionally water, to form a first mixture and optionally treating the mixture with phytase at a temperature and a pH suitable for phytase activity;

ii) optionally adjusting the pH of the first mixture to a pH of about 6.5 to about 10.0;

iii) separating the first mixture to remove fiber from the first mixture and form a protein slurry and an insoluble fiber fraction, wherein the protein slurry comprises a soluble protein fraction and an insoluble protein fraction and the insoluble fiber fraction comprises insoluble fiber and a second insoluble protein fraction;

iv) optionally mixing the insoluble fiber fraction with a second blending solvent, optionally water, to form a washed insoluble fiber fraction and an extract;

v) separating the washed insoluble fiber fraction from the extract;

vi) optionally mixing the washed insoluble fiber fraction with a blending solvent, optionally water, to form a second mixture;

vii) optionally adjusting the pH of the second mixture to a pH suitable for enzymatic activity;

viii) mixing the second mixture with at least one protease to form a hydrolyzed protein extract;

ix) separating the hydrolyzed protein extract from the second mixture to form the hydrolyzed protein concentrate and a second insoluble fiber fraction; and x) optionally drying the hydrolyzed protein concentrate.

In another embodiment of the disclosure, the ratio of macroalgae and/or microalgae to water is about 1:4 to about 1:30 (w/w). In another embodiment, the ratio of macroalgae and/or microalgae to water is about 1:5 to about 1:20 (w/w). In a further embodiment, the ratio is about 1:6 to about 1:12 (w/w). In an embodiment, the ratio is about 1:8 to about 1:10 (w/w).

In another embodiment, the pH of the first mixture is adjusted to about 8.0 to about 9.5. In a further embodiment, the pH of the first mixture is adjusted to about 8.5 to about 9.0.

In another embodiment of the disclosure, the first mixture is separated by centrifugation, gravity sedimentation, a gravity table or hydrocyclone to separate the fiber from the first mixture and form the protein slurry. In a further embodiment, the mixture is separated by centrifugation to separate the fiber from the mixture and form the protein slurry. In an embodiment, the first mixture is centrifuged at a speed of about 1,000 rpm to about 2,000 rpm. In a further embodiment, the first mixture is centrifuged at a speed of about 1,400 to about 1,600 rpm. In an embodiment, the mixture is centrifuged using a decanter centrifuge.

In another embodiment, the ratio of the insoluble fiber fraction or washed insoluble fiber fraction to water is about 1.0:0.5 to about 1.0:3.0 (w/w). In a further embodiment, the ratio of the insoluble fiber fraction or washed insoluble fiber fraction to water is about 1.0:1.0 to about 1.0:2.0 (w/w).

In another embodiment, the washed insoluble fiber fraction is centrifuged to separate the washed insoluble fiber fraction from extract. In a further embodiment, the washed insoluble fiber fraction is centrifuged at a speed of about 2,000 rpm to about 6,000 rpm. In a further embodiment, washed insoluble fiber fraction is centrifuged at a speed of about 3,000 to about 5,500 rpm.

In another embodiment of the disclosure, the pH of the second mixture is adjusted to about 8.0 to about 9.0.

In an embodiment of the disclosure, the ratio of the second mixture to the protease is about 100:1 to about 5000:1 (w/w).

In an embodiment of the disclosure, the second mixture is mixed with a protease at a temperature of about 40° C. to about 60° C. In another embodiment, the second mixture is mixed with a protease at a temperature of about 45° C. to about 55° C.

In another embodiment, the at least one protease comprises a protease from *Bacillus Licheniformis*.

In a further embodiment, the process further comprises the step of mixing the second mixture with a second protease.

In an embodiment, the ratio of the second mixture to the second protease is about 250:1 to about 5000:1 (w/w).

In another embodiment, the second mixture is mixed with the second protease at a temperature of about 50° C. to about 70° C. In another embodiment, the second mixture is mixed with the second protease at a temperature of about 55° C. to about 65° C.

In a further embodiment, the second protease comprises a fungal protease/peptidase complex from *Aspergillus oryzae*.

In another embodiment, the hydrolyzed protein concentrate is dried in a vacuum dryer, fluidized bed dryer, ring dryer or spray dryer to form the protein isolate.

In a further embodiment, the hydrolyzed protein concentrate comprises a protein content of about 50% to about 90% on a dry weight basis.

In another embodiment, the process further comprises mixing the hydrolyzed protein extract with water to form a third mixture. In a further embodiment, the process further comprises filtering the third mixture fraction and the filtering comprises ultrafiltration. In an embodiment, the ultrafiltration comprises contacting the third mixture with an ultrafiltration apparatus that comprises a membrane to filter proteins larger than about 1,000 daltons.

In another embodiment, the process further comprises mixing the second insoluble fiber fraction to form a washed hydrolyzed protein extract and a washed second insoluble fiber fraction and separating the form the washed hydrolyzed protein extract from the washed second insoluble fiber fraction. In another embodiment, the washed hydrolyzed protein extract is combined with the hydrolyzed protein extract.

In an embodiment of the disclosure, there is also provided a process for the production of a protein concentrate from macroalgae and/or microalgae as shown in FIGS. 27-31, comprising:
i) mixing the macroalgae and/or microalgae with a blending solvent, optionally water, a saline solution or a polysaccharide solution, to form a mixture and optionally treating the mixture with phytase at a temperature and a pH suitable for phytase activity;
ii) optionally adjusting the pH of the mixture to a pH of about 2.0 to about 10.0;
iii) separating fiber from the mixture to form a protein slurry, wherein the protein slurry comprises a first soluble protein fraction and an insoluble protein fraction;
iv) optionally repeating steps i)-iii) by mixing the protein slurry with additional algae;
v) separating the soluble protein fraction from the insoluble protein fraction;
vi) washing the insoluble protein fraction with a second blending solvent, optionally water, saline solution or polysaccharide solution, to form a washed insoluble protein fraction and a second soluble protein fraction;
vii) separating the washed insoluble protein fraction and the second soluble protein fraction;
viii) combining and separating the first and second soluble protein fractions to form a protein concentrate, optionally by filtering the first and second soluble protein fractions to form a protein concentrate or isolate;
ix) combining the washed insoluble protein fraction with the protein concentrate to form a combined protein concentrate or isolate; and
x) optionally drying the combined protein concentrate.

In another embodiment of the disclosure, the ratio of macroalgae and/or microalgae to water is about 1:3 to about 1:30 (w/w). In another embodiment, the ratio of macroalgae and/or microalgae to water is about 1:5 to about 1:20 (w/w). In a further embodiment, the ratio is about 1:6 to about 1:12 (w/w). In an embodiment, the ratio is about 1:8 to about 1:10 (w/w).

In an embodiment, the pH of the mixture is adjusted to a pH of about 6.5 to about 10.0. In another embodiment, the pH of the mixture is adjusted to a pH of about 7.0 to about 9.0.

In another embodiment of the disclosure, the mixture is separated by centrifugation, gravity sedimentation, a gravity table or hydrocyclone to separate the fiber from the mixture and form the protein slurry. In a further embodiment, the mixture is separated by centrifugation to separate the fiber from the mixture and form the protein slurry. In an embodiment, the mixture is centrifuged at a speed of about 1,000 rpm to about 2,000 rpm. In a further embodiment, the mixture is centrifuged at a speed of about 1,400 to about 1,600 rpm. In an embodiment, the mixture is centrifuged using a decanter centrifuge.

In another embodiment, the protein slurry is centrifuged to separate the protein solids fraction from the soluble protein fraction. In an embodiment, the protein slurry is centrifuged at a speed of about 6,000 rpm to about 8,500 rpm in a disc stack centrifuge. In another embodiment, the protein slurry is centrifuged at a speed of about 6,500 to about 7,500 rpm.

In another embodiment, the ratio of the insoluble protein fraction to water is about 1.0:0.5 to about 1.0:3.0 (w/w). In a further embodiment, the ratio of the insoluble protein fraction to water is about 1.0:1.0 to about 1.0:2.0 (w/w).

In another embodiment, the washed insoluble protein fraction and the second soluble protein fraction are separated using a centrifuge. In an embodiment, the washed insoluble protein fraction and the second soluble protein fraction are centrifuged at a speed of about 6,000 rpm to about 8,500 rpm in a disc stack centrifuge. In a further embodiment, the washed insoluble protein fraction and the second soluble protein fraction are centrifuged at a speed of about 6,500 to about 7,500 rpm.

In another embodiment, the first and second soluble protein fractions are filtered using an ultrafiltration apparatus. In a further embodiment, the ultrafiltration apparatus comprises a membrane to filter proteins larger than about 10,000 daltons. In an embodiment, the process further comprises the step of filtering the first and second soluble protein fractions using a diafiltration apparatus.

In another embodiment, the combined protein concentrate is dried in a vacuum dryer, fluidized bed dryer, ring dryer or spray dryer to form the dried protein concentrate.

In another embodiment, the protein concentrate comprises a hydrolyzed protein concentrate. In another embodiment, the protein concentrate is hydrolyzed to produce peptides and free amino acids. In another embodiment, the hydrolyzed protein concentrate comprises peptides and/or free amino acids.

In a further embodiment, the protein concentrate comprises a protein content of about 30% to about 90% on a dry weight basis.

In an embodiment of the disclosure, there is also provided a process for the production of a protein isolate from macroalgae and/or microalgae comprising:
  i) mixing the macroalgae and/or microalgae with a blending solvent, optionally water, to form a mixture and optionally treating the mixture with phytase at a temperature and a pH suitable for phytase activity;
  ii) optionally adjusting the pH of the mixture to a pH of about 2.0 to about 10.0;
  iii) separating fiber from the mixture to form a protein slurry, wherein the protein slurry comprises a soluble protein fraction and an insoluble protein fraction;
  iv) washing the fiber with a second blending solvent, optionally water, to form a washed fiber fraction;
  vi) separating the washed fiber fraction to form a second protein slurry and washed fiber solids;
  vii) combining and separating the first and second protein slurries to form a protein concentrate, optionally by filtering the first and second soluble protein fractions to form a protein concentrate; and
  ix) optionally drying the protein concentrate.

In another embodiment of the disclosure, the ratio of macroalgae and/or microalgae to water is about 1:3 to about 1:30 (w/w). In another embodiment, the ratio of macroalgae and/or microalgae to water is about 1:5 to about 1:20 (w/w). In a further embodiment, the ratio is about 1:6 to about 1:12 (w/w). In an embodiment, the ratio is about 1:8 to about 1:10 (w/w).

In an embodiment, the pH of the mixture is adjusted to a pH of about 6.5 to about 10.0. In another embodiment, the pH of the mixture is adjusted to a pH of about 7.0 to about 9.0.

In another embodiment of the disclosure, the mixture is separated by centrifugation, gravity sedimentation, a gravity table or hydrocyclone to separate the fiber from the mixture and form the protein slurry. In a further embodiment, the mixture is separated by centrifugation to separate the fiber from the mixture and form the protein slurry. In an embodiment, the mixture is centrifuged at a speed of about 1,000 rpm to about 2,000 rpm. In a further embodiment, the mixture is centrifuged at a speed of about 1,400 to about 1,600 rpm. In an embodiment, the mixture is centrifuged using a decanter centrifuge.

In another embodiment, the ratio of the fiber fraction to water is about 1.0:0.5 to about 1.0:3.0 (w/w). In a further embodiment, the ratio of the insoluble protein fraction to water is about 1.0:1.0 to about 1.0:2.0 (w/w).

In another embodiment of the disclosure, the washed fiber fraction is separated by centrifugation, gravity sedimentation, a gravity table or hydrocyclone to separate the fiber solids and form second the protein slurry. In a further embodiment, the washed fiber fraction is separated by centrifugation to separate the fiber and form the second protein slurry. In an embodiment, the mixture is centrifuged at a speed of about 1,000 rpm to about 2,000 rpm. In a further embodiment, the fiber fraction is centrifuged at a speed of about 1,400 to about 1,600 rpm. In an embodiment, the fiber fraction is centrifuged using a decanter centrifuge.

In another embodiment, the first and second slurries are filtered using an ultrafiltration/microfiltration apparatus. In a further embodiment, the ultrafiltration/microfiltration apparatus comprises a membrane to filter proteins larger than about 10,000 daltons. In an embodiment, the process further comprises the step of filtering the first and second slurries using a diafiltration apparatus.

In another embodiment, the protein concentrate is dried in a vacuum dryer, fluidized bed dryer, ring dryer or spray dryer to form the dried protein concentrate.

In another embodiment, the protein isolate comprises a hydrolyzed protein isolate. In another embodiment, the protein isolate is hydrolyzed to produce peptides and free amino acids. In another embodiment, the hydrolyzed protein isolate comprises peptides and/or free amino acids.

In a further embodiment, the protein concentrate comprises a protein content of about 30% to about 90% on a dry weight basis.

The present disclosure also relates to processes for the production of protein concentrates and protein isolates, in which the macroalgae and/or microalgae is subjected to low g-forces to separate the fiber from the insoluble and soluble protein fractions. Removing the fiber from a protein mixture using low g-forces, separates the insoluble fiber from the protein fraction, and in particular the insoluble protein fraction, which consequently increases the amount of recoverable protein from macroalgae and/or microalgae.

The present disclosure relates to processes for the production of protein concentrates and protein isolates, in which the macroalgae and/or microalgae is subjected to low g-forces to separate the fiber from the insoluble and soluble protein fractions. Removing the fiber from a protein mixture using low g-forces, separates the insoluble fiber from the protein fraction, and in particular the insoluble protein fraction, which consequently increases the amount of recoverable protein from macroalgae and/or microalgae.

Figure 32:
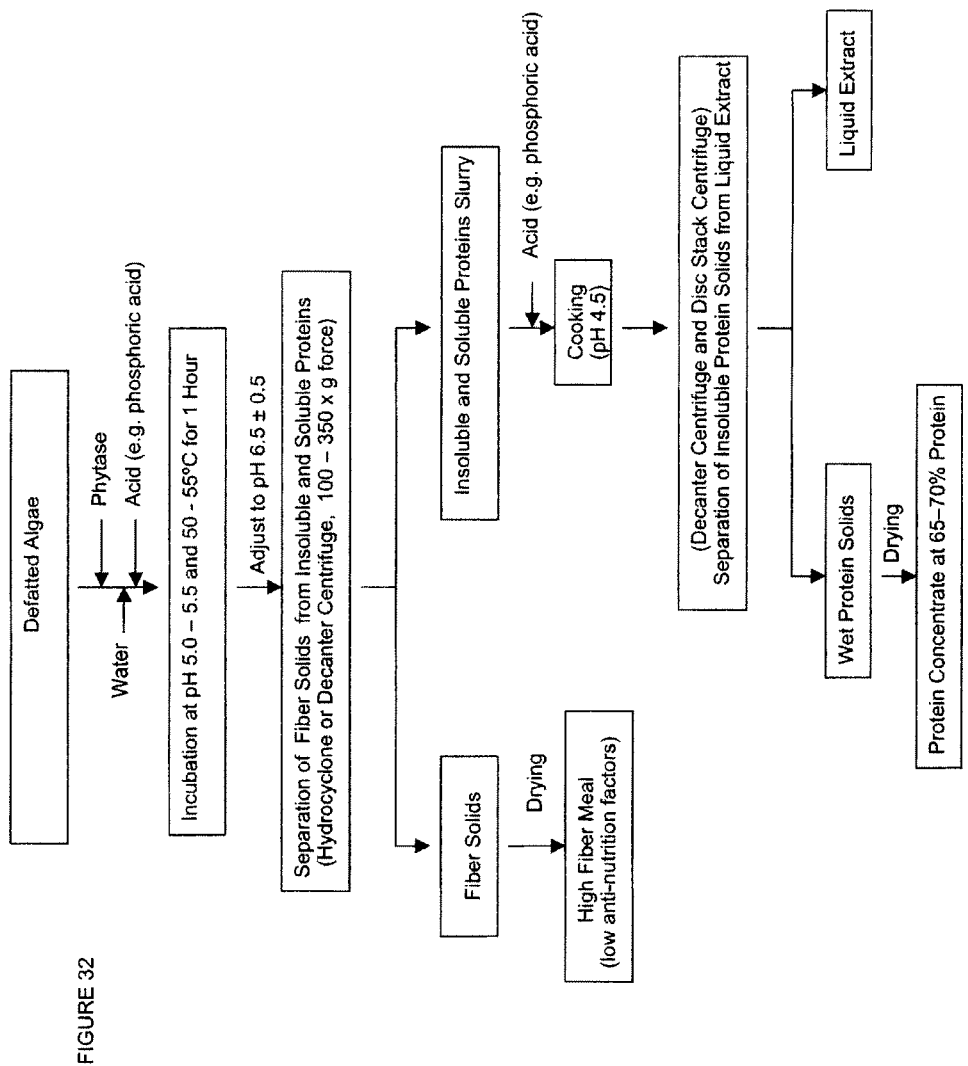
FIG. 32 is a schematic representation in a first embodiment showing the removal of fiber during the preparation of a protein concentrate from a defatted algae.

Accordingly, the present disclosure includes a process for the production of a protein concentrate from macroalgae and/or microalgae as shown in FIG. 32, comprising:
  i) mixing the macroalgae and/or microalgae with a first blending solvent to form a mixture;
  ii) optionally treating the mixture with phytase at a temperature and a pH suitable for phytase activity;
  iii) optionally adjusting the pH of the mixture to a pH between 6.0 and 10.0;
  iv) subjecting the mixture to a g-force sufficient to separate the mixture to form
    a) a fiber fraction, and
    b) protein fractions comprising an insoluble protein fraction and a soluble protein fraction;
  v) optionally mixing the fiber fraction with a second blending solvent and repeating step iv);

vi) optionally adjusting the pH of the protein fraction to a pH between 4.0 and 6.0;

vii) heating the protein fraction to a temperature between 80° C. and 100° C. to precipitate the proteins; and viii) separating the precipitated proteins from the protein fraction to form the protein concentrate.

In another embodiment, the first and second blending solvents comprise water, a saline solution or a polysaccharide solution. In a further embodiment, the first and second blending solvents comprise water.

In an embodiment of the disclosure, the ratio of the macroalgae and/or microalgae to the first blending solvent is 1:3 to 1:30 (w/w) of algae to water, optionally about 1:8 to about 1:10 (w/w).

In an embodiment, the temperature suitable for phytase activity is between 20° C. and 60° C., optionally between 40° C. and 55° C., suitably between 50° C. and 55° C. In another embodiment, the pH suitable for phytase activity is between 2.0 and 7.0, optionally between 4.0 and 6.0, suitably between 4.5 and 5.5, optionally 5.0 to 5.5. In another embodiment, the concentration of the phytase enzyme is between 0.01% to 1.0% (w/w) based on the weight of the macroalgae and/or microalgae, optionally 0.01% and 0.5% optionally 0.01% and 0.1%. In another embodiment, the mixture is incubated with the phytase enzyme under good agitation. The addition of phytase enzyme to the protein mixture results in the hydrolysis of phytates and/or phytic acid present in the macroalgae and/or microalgae to organic phosphates and inositol. It is known to those skilled in the art that phytates and phytic acid may constitute undesirable anti-nutritional compounds in a protein algae, and accordingly, are desirably removed from the macroalgae and/or microalgae and the final protein products. Accordingly, the addition of phytase enzyme results in the hydrolysis of the phytates and/or phytic acid which are subsequently removed from the mixture. In addition, it has also been determined that phytates and/or phytic acid complex with proteins to form an insoluble gel complex. Accordingly, in an embodiment, when filtration, such as diafiltration or ultrafiltration, is utilized to purify and separate protein concentrates and/or protein isolates, the insoluble protein/phytate (or phytic acid) gel complexes block the filtration apparatus, reducing the flow through the filtration apparatus, and accordingly, reducing the amount of recoverable protein and filtration efficiency. It will be understood that the addition of phytase to the mixture and the conditions recited for reduction or removal of phytates and/or phytic acid apply to all of the processes and embodiments of the present disclosure.

In another embodiment of the disclosure, after treating the mixture with the phytase enzyme, the pH of the mixture is optionally adjusted to a pH of about 6.0 to about 10.0, optionally 6.5 to about 9.5, suitably 7.0 to 8.0, using a base, such as sodium hydroxide, potassium hydroxide, etc. In an embodiment, adjusting the pH of the mixture results in the protein becoming more soluble in the blending solvent, such as water, which consequently increases the yield of the protein concentrate.

In another embodiment of the disclosure, the mixture is subjected to a g-force sufficient to separate the mixture to form a fiber fraction and protein fractions comprising an insoluble protein fraction and a soluble protein fraction. The separation of the mixture using a sufficient g-force is described herein with reference to a centrifuge, such as a decanter centrifuge or a disc stack centrifuge, but a person skilled in the art would understand that other methods of separation that create a separation force, including a hydrocyclone, are also included. Accordingly, in an embodiment, when the mixture is subjected to a sufficient g-force using a centrifuge, the mixture separates into three-phases as a result of the sedimentation principle: (i) an insoluble fiber fraction, and (ii) protein fractions comprising (ii.a) an insoluble protein fraction, and (ii.b) a soluble protein fraction. The centripetal acceleration acting on the mixture results in the insoluble fiber fraction, which has a relatively higher density and/or greater particle size compared to the other fractions, moving further along the radial direction in which the centripetal force is acting (perpendicular to the axis of rotation). When a centrifuge is utilized, the insoluble fiber fraction (or phase) moves towards the bottom of the centrifuge tube, as a result of its relatively higher density and/or greater particle size, resulting in one of the phases of separation. As a result of the proteins in the insoluble protein fraction having a lower relative density and/or smaller particle size as compared to the insoluble fiber fraction, the insoluble protein fraction forms another phase of separation (the middle phase). Finally, the proteins in the soluble protein fraction, being soluble in the blending solvent and/or having a lower relative density compared to the fiber fraction and insoluble protein fraction, remain near the top of the centrifuge tube. If macroalgae and/or microalgae is partially defatted algae, a fourth phase may also form on top of the soluble protein phase comprising residual oil. It will be understood that subjecting the mixture to a sufficient g-force will not result in a total separation of the three fractions, and accordingly, a minor amount of fiber will be present in the protein fraction, while protein will be present in the insoluble fiber fraction. There will be a certain amount of protein trapped within the structure of the insoluble fiber fraction that is not separable using mechanical means (i.e. using a centrifuge). In an embodiment, the amount of protein trapped within the fiber fraction will be 30%, optionally 20%, 10%, 5%, 1%. In another embodiment, proteases are used to hydrolyze the protein trapped within the fiber fraction, which releases the protein from the fiber, and can be recovered therefrom, and such a process is also included in the present disclosure. In another embodiment, proteases (such as Protames, Alcalase 2.4L FG and/or Flavourzyme 1000L) are used to hydrolyze the protein trapped within the fiber fraction, which releases the protein from the fiber, and can be recovered therefrom, and such a process is also included in the present disclosure. In this embodiment, the hydrolyzed protein is separated from the fiber using any of the means disclosed herein (e.g. centrifugation, hydrocyclone). It will be understood that the disclosure concerning the g-force sufficient to separate the mixture as described above applies to all of the processes and embodiments of the present disclosure.

In an embodiment, the mixture is subjected to a g-force of between 100 g and 500 g, suitably between 150 g and 400 g, optionally between 180 g and 350 g. Calculation of g-force (or relative centrifugal force) optionally involves the RPMs (revolutions per minute) of the device, as well as the rotational radius (in centimeters):

$$g\text{-force} = (RPM)^2 * (\text{rotational radius}) * (0.00001118)$$

A person skilled in the art will readily be able to calculate the g-force from the RPMs of a given separation device, such as a centrifuge or a hydrocyclone.

In another embodiment, separating the mixture comprises using a centrifuge or a hydrocyclone. In another embodiment, the centrifuge comprises a decanter centrifuge or a disc stack centrifuge.

In another embodiment, as there will be a residual amount of protein in the separated fiber fraction, the separated fiber fraction is washed with a second blending solvent, optionally at least once, optionally twice or more than twice, and the mixture is then again subjected to a g-force to separate the mixture to form a fiber fraction and a protein fraction comprising an insoluble protein fraction and a soluble protein fraction.

In another embodiment, the separation of the insoluble fiber fraction from the protein fractions, results in fiber solids which are dried and consequently constitute a high fiber algae fraction containing a low concentration of anti-nutritional factors, such as phytates and/or phytic acid.

In another embodiment, the pH of the protein fraction comprising the insoluble protein fraction and soluble protein fraction is adjusted using an acid, such as phosphoric acid, nitric acid, citric acid, sulfuric acid, and the pH is adjusted to between 4.0 and 6.0, optionally 4.0 and 5.0, suitably 4.0 and 4.5. In an embodiment, adjusting the pH of the protein fraction using an acid results in undesirable ash becoming soluble in the protein fraction, and therefore, separable from the final protein concentrate.

In another embodiment, the protein fraction comprising the insoluble protein fraction and the soluble protein fraction is heated to a temperature between 80° C. and 100° C., optionally 90° C. and 100° C., suitably 95° C. and 100° C., for a time period of between 5 minutes and 60 minutes, optionally 5 minutes and 45 minutes, suitably between 10 minutes and 30 minutes. Increasing the temperature of the protein fractions denatures some of the undenatured proteins in the soluble protein fraction, rendering them insoluble, and therefore increasing the yield of the insoluble protein concentrate.

In a further embodiment, separating the precipitated proteins comprises using a centrifuge or a hydrocyclone. In another embodiment, separating the precipitated proteins comprises using a centrifuge, such as decanter centrifuge or a disc stack centrifuge. In another embodiment, centrifuging the precipitated proteins comprises a g-force between 2,500 g and 9,500 g. When the centrifuge is operated at such a g-force, the precipitated proteins move along the radial axis to the bottom of the centrifuge tube and are easily separated from the supernatant.

In another embodiment of the disclosure, the process further comprising the step of drying the protein concentrate to a moisture content of between 4% and 8%, optionally 6% (w/w). In another embodiment, the drying is performed using a fluidized bed dryer, conveyor dryer, rotary dryer, drum dryer, spray drier or a ring drier.

In another embodiment, the protein concentrate comprises a hydrolyzed protein concentrate. In another embodiment, the hydrolyzed protein concentrate comprises peptides and/or free amino acids.

Figure 33:
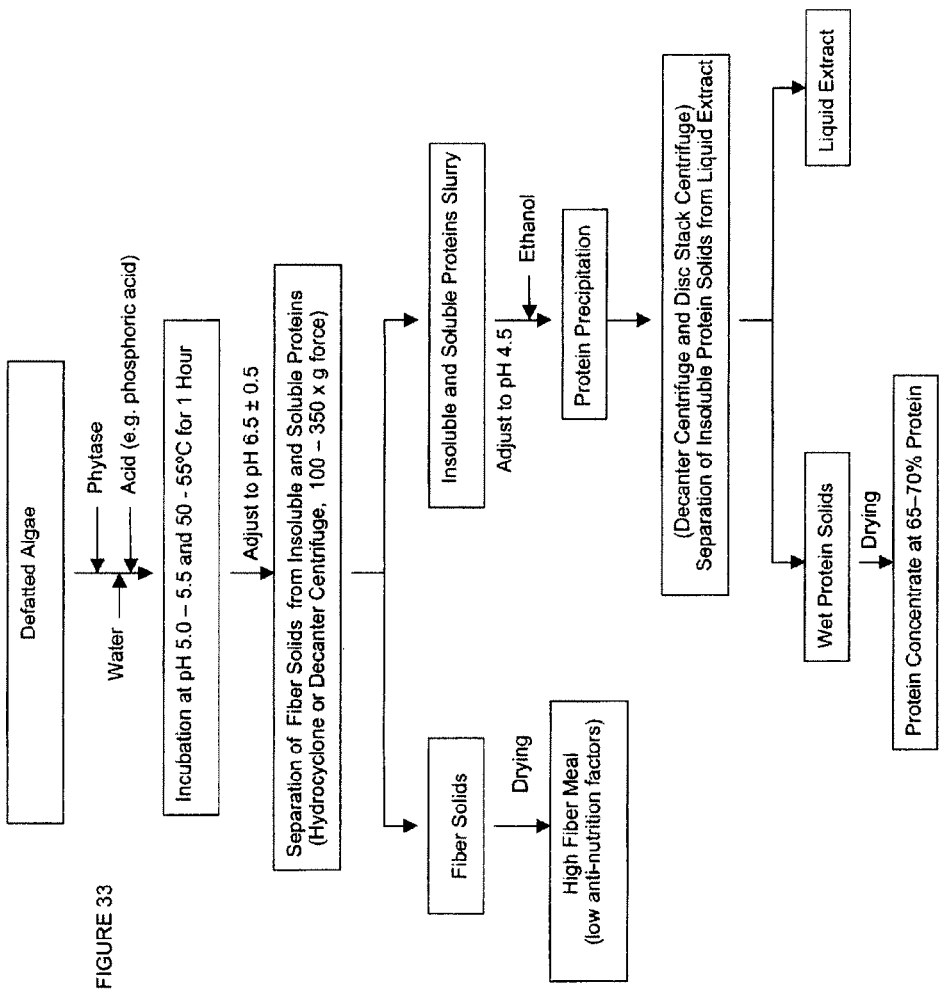
FIG. 33 is a schematic representation in a second embodiment showing the removal of fiber during the preparation of a protein concentrate from a defatted algae.

The present disclosure also includes a process for the production of a protein concentrate from macroalgae and/or microalgae as shown in FIG. 33, comprising:

i) mixing the macroalgae and/or microalgae with a first blending solvent to form a mixture;

ii) optionally treating the mixture with phytase at a temperature and a pH suitable for phytase activity;

iii) optionally adjusting the pH of the mixture to a pH between 6.0 and 10.0;

iv) subjecting the mixture to a g-force sufficient to separate the mixture to form
   a) a fiber fraction, and
   b) protein fractions comprising an insoluble protein fraction and a soluble protein fraction;

v) optionally mixing the fiber fraction with a second blending solvent and repeating step iv);

vi) optionally adjusting the pH of the protein fraction to a pH between 4.0 and 6.0;

vii) mixing the protein fraction with a mixing solvent to form a protein slurry and precipitate the proteins;

viii) separating the precipitated proteins from the protein slurry to form the protein concentrate; and ix) optionally repeating steps vii) and viii) with the precipitated proteins.

In another embodiment, the first and second blending solvents comprise water, a saline solution or a polysaccharide solution. In a further embodiment, the first and second blending solvents comprise water.

In an embodiment of the disclosure, the ratio of the macroalgae and/or microalgae to the first blending solvent is 1:3 to 1:30 (w/w) of algae to water, optionally about 1:8 to about 1:10 (w/w).

In an embodiment, the temperature suitable for phytase activity is between 20° C. and 60° C., optionally between 40° C. and 55° C., suitably between 50° C. and 55° C. In another embodiment, the pH suitable for phytase activity is between 2.0 and 7.0, optionally between 4.0 and 6.0, suitably between 4.5 and 5.5, optionally 5.0 to 5.5. In another embodiment, the concentration of the phytase enzyme is between 0.01% to 1.0% (w/w) based on the weight of the macroalgae and/or microalgae, optionally 0.01% and 0.5% optionally 0.01% and 0.1%. In another embodiment, the mixture is incubated with the phytase enzyme under good agitation.

In another embodiment of the disclosure, after treating the mixture with the phytase enzyme, the pH of the mixture is optionally adjusted to a pH of about 6.0 to about 10.0, optionally 6.5 to about 9.5, suitably 7.0 to 8.0, using a base, such as sodium hydroxide, potassium hydroxide, etc. In an embodiment, adjusting the pH of the mixture results in the protein becoming more soluble in the blending solvent, such as water, which consequently increases the yield of the protein concentrate.

In another embodiment of the disclosure, the mixture is subjected to a g-force of between 100 g and 500 g, suitably between 150 g and 400 g, optionally between 180 g and 350 g.

In another embodiment, separating the mixture comprises using a centrifuge or a hydrocyclone. In another embodiment, the centrifuge comprises a decanter centrifuge or disc stack centrifuge.

In another embodiment, as there will be a residual amount of protein in the separated fiber fraction, the separated fiber fraction is washed with a second blending solvent, optionally at least once, optionally twice or more than twice, and the mixture is then again subjected to a g-force to separate the mixture to form a fiber fraction and a protein fraction comprising an insoluble protein fraction and a soluble protein fraction.

In another embodiment, the separation of the insoluble fiber fraction from the protein fraction, results in fiber solids which are dried and consequently constitute a high fiber algae fraction containing a low concentration of anti-nutritional factors, such as phytates and/or phytic acid.

In another embodiment, the pH of the protein fraction comprising the insoluble protein fraction and soluble protein fraction is adjusted using an acid, such as phosphoric acid, nitric acid, citric acid, sulfuric acid, hydrochloric acid, and the pH is adjusted to between 4.0 and 6.0, optionally 4.0 and 5.0, suitably 4.0 and 4.5. In an embodiment, adjusting the pH of the protein fraction using an acid results in undesirable ash becoming soluble in the protein fraction, and therefore, separable from the final protein concentrate.

In another embodiment of the disclosure, the protein fraction is mixed with a mixing solvent comprising an ethanol: water mixture, wherein the ethanol is present in an amount between 90% and 100%, optionally 95% and 100% (v/v). It will be understood that 100% ethanol may contain a small percentage of impurities such as water, etc., which cannot be removed from the ethanol. In an embodiment, mixing solvent is added to the protein fraction at a ratio of between 2:1 and 1:2 (v/v of mixing solvent:protein fraction), optionally 1:1. In an embodiment, when the mixing solvent comprises an alcohol, such as ethanol (80%, 90%, 95% ethanol in water or 100% ethanol), proteins in the protein slurry precipitate from solution, as a result the proteins being less soluble in the mixing solvent (such as ethanol) than in the blending solvent (such as water), and therefore increases the yield of the protein concentrate.

In another embodiment, separating the precipitated proteins comprises using a centrifuge or a hydrocyclone. In another embodiment, separating the precipitated proteins comprises using a centrifuge, such as decanter centrifuge or disc stack centrifuge. In another embodiment, centrifuging the precipitated proteins comprises a g-force between 2,500 g and 9,500 g. When the centrifuge is operated at such a g-force, the precipitated proteins move along the radial axis to the bottom of the centrifuge tube and are easily separated from the supernatant.

In another embodiment of the disclosure, steps viii) and viii) are repeated at least twice, such that the precipitated proteins are washed with mixing solvent to remove impurities.

In another embodiment, the process further comprises the step of drying the protein concentrate to a moisture content of between 4% and 8% (w/w), optionally 6% (w/w). In another embodiment, the drying is performed using a fluidized bed dryer, spray dryer or a ring drier.

In another embodiment, the protein concentrate comprises a hydrolyzed protein concentrate. In a further embodiment, the hydrolyzed protein concentrate comprises peptides and/or free amino acids.

Figure 34:
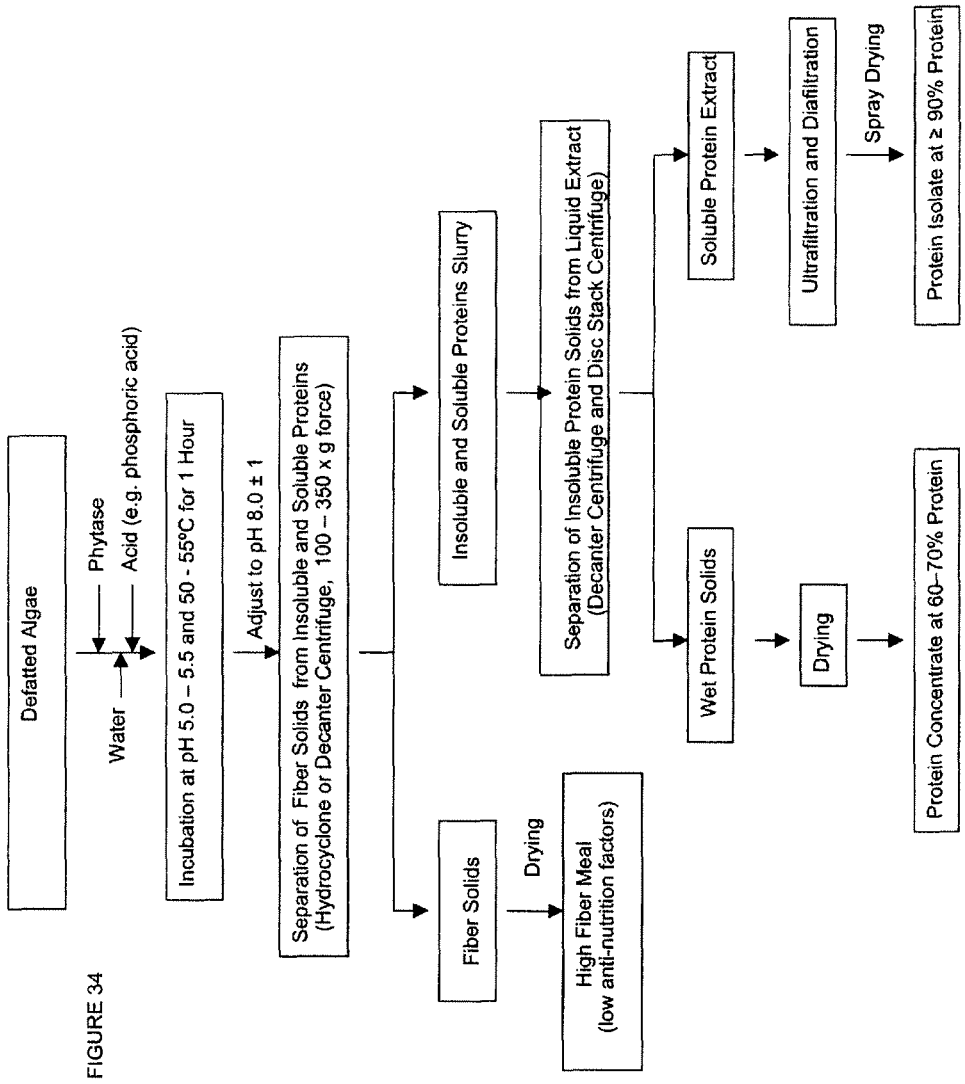
FIG. 34 is a schematic representation showing the removal of fiber during the preparation of a protein concentrate and a protein isolate from a defatted algae.

The present disclosure also includes a process for the production of a protein isolate from macroalgae and/or microalgae as shown in FIG. 34, comprising:

i) mixing the macroalgae and/or microalgae with a first blending solvent to form a mixture;

ii) optionally treating the mixture with phytase at a temperature and a pH suitable for phytase activity;

iii) optionally adjusting the pH of the mixture to a pH between 6.0 and 10.0;

iv) subjecting the mixture to a g-force sufficient to separate the mixture to form
   a) a fiber fraction, and
   b) protein fractions comprising an insoluble protein fraction and a soluble protein fraction;

v) optionally mixing the fiber fraction with a second blending solvent and repeating step iv);

vi) separating the insoluble protein fraction from the soluble protein fraction to recover therefrom an insoluble protein concentrate and a soluble protein extract; and vii) subjecting the soluble protein extract to filtration to recover therefrom the protein isolate.

In another embodiment, the first and second blending solvents comprise water, a saline solution or a polysaccharide solution. In a further embodiment, the first and second blending solvents comprise water.

In an embodiment of the disclosure, the ratio of the macroalgae and/or microalgae to the first blending solvent is 1:3 to 1:30 (w/w) of algae to water, optionally 1:8 to 1:10 (w/w).

In an embodiment, the temperature suitable for phytase activity is between 20° C. and 60° C., optionally between 40° C. and 55° C., suitably between 50° C. and 55° C. In another embodiment, the pH suitable for phytase activity is between 2.0 and 7.0, optionally between 4.0 and 6.0, suitably between 4.5 and 5.5, optionally 5.0 and 5.5. In another embodiment, the concentration of the phytase enzyme is between 0.01% and 1.0% (w/w) based on the weight of the macroalgae and/or microalgae, optionally 0.01% and 0.5% optionally 0.01% and 0.1%. In another embodiment, the mixture is incubated with the phytase enzyme under good agitation.

In another embodiment of the disclosure, after treating the mixture with the phytase enzyme, the pH of the mixture is optionally adjusted to a pH of between 6.0 and about 10.0, optionally 7.0 and 9.0, suitably 7.0 and 8.0, using a base, such as sodium hydroxide, potassium hydroxide, etc. In an embodiment, adjusting the pH of the mixture results in the protein becoming more soluble in the blending solvent, such as water, which consequently increases the yield of the protein isolate.

In another embodiment of the disclosure, the mixture is subjected to a g-force of between 100 g and 500 g, suitably between 150 g and 400 g, optionally between 180 g and 350 g.

In another embodiment, separating the mixture comprises using a centrifuge or a hydrocyclone. In an embodiment, the centrifuge comprises a decanter centrifuge or disc stack centrifuge.

In another embodiment, as there will be a residual amount of protein in the separated fiber fraction, the separated fiber fraction is washed with a second blending solvent, optionally at least once, optionally twice or more than twice, and the mixture is then again subjected to a g-force to separate the mixture to form a fiber fraction and a protein fraction comprising an insoluble protein fraction and a soluble protein fraction.

In another embodiment, the separation of the insoluble fiber fraction from the protein fraction, results in fiber solids which are dried and consequently constitute a high fiber algae fraction containing a low concentration of anti-nutritional factors, such as phytates and/or phytic acid.

In another embodiment, separating the insoluble protein fraction from the soluble fiber fraction comprises using a centrifuge or a hydrocyclone. In a further embodiment separating the insoluble protein fraction from the soluble protein fraction comprises using a centrifuge, such as a decanter centrifuge or disc stack centrifuge.

In another embodiment, centrifuging to separate the insoluble protein fraction from the soluble protein fraction comprises a g-force between 2,500 g and 9,500 g. In another embodiment, the separation of the insoluble protein fraction from the soluble protein fraction results in a wet protein concentrate that can be subsequently dried. The extract from the separation of the insoluble protein fraction from the soluble protein fraction comprises the soluble protein, which is subsequently filtered through a filtration apparatus, such as ultrafiltration and/or diafiltration, resulting in the protein isolate. As described above, phytates and/or phytic acid can complex and bind to the proteins, and consequently block the filtration apparatus. The removal of the phytates and/or phytic acid from the macroalgae and/or microalgae mixture (algae and blending solvent) using phytase as described above, such that the filtration apparatus is not blocked with such complexes, resulting the filtration apparatus performing efficiently to produce the protein isolate.

In another embodiment, the process further comprises the step of drying the protein isolate to a moisture content of between 4% and 8% (w/w), optionally 6% (w/w). In another embodiment, the drying is performed using a spray drier or a ring drier.

In a further embodiment, the protein isolate comprises a hydrolyzed protein isolate. In another embodiment, the hydrolyzed protein concentrate comprises peptides and/or free amino acids.

In another embodiment, the present disclosure includes a process for obtaining a protein concentrate from macroalgae and/or microalgae comprising:
  i) mixing the macroalgae and/or microalgae with a first blending solvent to form a mixture;
  ii) optionally treating the mixture with phytase at a temperature and a pH suitable for phytase activity;
  iii) optionally adjusting the pH of the mixture to a pH suitable to solubilize proteins in the mixture;
  iv) subjecting the mixture to a g-force sufficient to separate the mixture to form
    a) a fiber fraction, and
    b) a protein fraction comprising
      (i) an insoluble protein fraction, and
      (ii) a soluble protein fraction;
  v) separating the fiber fraction from the protein fraction and mixing the fiber fraction with a second blending solvent to form a fiber mixture;
  vi) treating the fiber mixture with a protease at a temperature and a pH suitable for protease activity;
  vii) subjecting the fiber mixture to a g-force sufficient to separate the fiber mixture to form:
    a) a second fiber fraction, and
    b) a hydrolyzed protein fraction, comprising
      (i) an insoluble protein fraction comprising partially hydrolyzed and un-hydrolyzed protein, and
      (ii) a soluble hydrolyzed protein fraction;
  viii) optionally adjusting the pH of the protein fraction from step iv(b) to a pH suitable to precipitate the proteins;
  x) separating the precipitated proteins from the protein fraction;
  xi) optionally combining the precipitated proteins and the hydrolyzed protein fraction to form the protein concentrate.

In one embodiment, the pH of the mixture (algae and first blending solvent) is optionally adjusted to solubilize proteins (undenatured proteins) into the first blending solvent. In an embodiment, the pH of the mixture is adjusted to a pH between 6 and 8, optionally between 6.5 and 7.5, optionally about 7.0, using a base such as sodium hydroxide, which solubilizes some of the proteins present in the algae, and upon low g-force separation, increases the amount of protein in the protein fraction. In addition, adjusting the pH to about 7.0 results in the fiber fraction (after low g-force separation of the mixture) having a neutral pH as a by-product.

In another embodiment, the process further comprises mixing the fiber fraction with the first blending solvent and repeating step iv) once, twice or three times and/or mixing the second fiber fraction with the second blending solvent and repeating step vii) once, twice or three times. The repeated washing of the fiber fractions with the blending solvent increases the amount of protein that is recovered for the protein concentrate as the repeated washings separates additional protein that is trapped within the fiber structure.

In another embodiment, the first and second blending solvents comprise water, a saline solution or a polysaccharide solution, optionally water, and wherein the ratio of the macroalgae and/or microalgae to the first blending solvent is 1:3 to 1:30 (w/w) of algae to water, optionally 1:8.

In another embodiment, the temperature suitable for phytase activity is between 20° and 60° C. and the pH suitable for phytase activity is between 2.0 and 7.0 and the temperature suitable for protease activity is between 30° and 70° C. and the pH suitable for protease activity is between 5.0 and 9.0.

In another embodiment, the mixture and/or the fiber mixture is subjected to a g-force of between 100 g and 500 g, optionally between 150 g and 400 g, or between 170 g and 350 g. In an embodiment, separating the mixture and/or the fiber mixture comprises using a centrifuge or a hydrocyclone, optionally a decanter centrifuge.

In a further embodiment, the pH of the protein fraction from step iv(b) is adjusted to precipitate proteins in the protein fraction. The protein fraction comprises (i) an insoluble protein fraction, and (ii) a soluble protein fraction, and the adjustment of the pH precipitates proteins from the soluble protein fraction, and therefore increases the yield of the protein concentrate. In one embodiment, the pH of the protein fraction is adjusted to the isoelectric point of the soluble protein, at which point the soluble protein precipitates from solution. In one embodiment, the pH suitable to precipitate the proteins in the protein fraction is between 4.0 and 6.0, optionally 4.0 and 5.0, suitably 4.0 and 4.5 using an acid such as phosphoric acid, nitric acid, sulfuric acid, hydrochloric acid, optionally phosphoric acid having a concentration of 40% to 60% (w/w), optionally about 50%. In another embodiment, adjusting the pH of the protein fraction using an acid results in undesirable ash becoming soluble in the protein fraction, and therefore, separable from the final protein concentrate.

In another embodiment, separating the precipitated proteins comprises using a centrifuge or a hydrocyclone. In another embodiment, separating the precipitated proteins comprises using a centrifuge, such as decanter centrifuge or disc stack centrifuge. In another embodiment, centrifuging the precipitated proteins comprises a g-force between 2,500 g and 9,500 g. When the centrifuge is operated at such a g-force, the precipitated proteins move along the radial axis to the bottom of the centrifuge tube and are easily separated from the supernatant.

In another embodiment, the process further comprises the step of drying the protein concentrate to a moisture of between 4% and 8% (w/w). In another embodiment, the protein concentrate also comprises peptides and free amino acids.

The present disclosure also includes a process for the production of a protein concentrate from macroalgae and/or microalgae comprising:
  i) mixing the macroalgae and/or microalgae with a first blending solvent to form a mixture;
  ii) optionally treating the mixture with phytase at a temperature and a pH suitable for phytase activity;
  iii) optionally adjusting the pH of the mixture to a pH suitable to solubilize proteins in the mixture;
  iv) subjecting the mixture to a g-force sufficient to separate the mixture to form
    a) a fiber fraction, and
    b) a protein fraction comprising
      (i) an insoluble protein fraction, and
      (ii) a soluble protein fraction;
  v) separating the fiber fraction from the protein fraction and mixing the fiber fraction with a second blending solvent to form a fiber mixture;
  vi) treating the fiber mixture with a protease at a temperature and a pH suitable for protease activity;
  vii) subjecting the fiber mixture to a g-force sufficient to separate the fiber mixture to form:

a) a second fiber fraction, and
b) a hydrolyzed protein fraction, comprising
  (i) an insoluble protein fraction, and
  (ii) a soluble hydrolyzed protein fraction;
ix) mixing the protein fraction with a mixing solvent to precipitate proteins;
x) separating the precipitated proteins from the protein fraction; and
xi) optionally combining the precipitated proteins and the hydrolyzed protein fraction to form the protein concentrate.

In one embodiment, the pH of the mixture (algae and first blending solvent) is optionally adjusted to solubilize proteins (undenatured proteins) into the first blending solvent. In an embodiment, the pH of the mixture is adjusted to a pH between 6 and 8, optionally between 6.5 and 7.5, optionally about 7.0, using a base such as sodium hydroxide, which solubilizes some of the proteins present in the algae, and upon low g-force separation, increases the amount of protein in the protein fraction. In addition, adjusting the pH to about 7.0 results in the fiber fraction (after low g-force separation of the mixture) having a neutral pH as a by-product.

In another embodiment, the process further comprises mixing the fiber fraction with the first blending solvent and repeating step iv) once, twice or three times and/or mixing the second fiber fraction with the second blending solvent and repeating step vii) once, twice or three times. The repeated washing of the fiber fractions with the blending solvent increases the amount of protein that is recovered for the protein concentrate as the repeated washings separates additional protein that is trapped within the fiber structure.

In another embodiment, the first and second blending solvents comprise water, a saline solution or a polysaccharide solution, optionally water, and wherein the ratio of the macroalgae and/or microalgae to the first blending solvent is 1:3 to 1:30 (w/w) of algae to water, optionally 1:8.

In another embodiment, the temperature suitable for phytase activity is between 20° and 60° C. and the pH suitable for phytase activity is between 2.0 and 7.0 and the temperature suitable for protease activity is between 30° and 70° C. and the pH suitable for protease activity is between 5.0 and 9.0.

In another embodiment, the mixture and/or the fiber mixture is subjected to a g-force of between 100 g and 500 g, optionally between 150 g and 400 g, or between 170 g and 350 g. In an embodiment, separating the mixture and/or the fiber mixture comprises using a centrifuge or a hydrocyclone, optionally a decanter centrifuge.

In another embodiment, the pH of the protein fraction from step iv(b) is adjusted using an acid, such as phosphoric acid, nitric acid, citric acid, sulfuric acid, hydrochloric acid, and the pH is adjusted to between 4.0 and 6.0, optionally 4.0 and 5.0, suitably 4.0 and 4.5. In an embodiment, adjusting the pH of the protein fraction using an acid results in undesirable ash becoming soluble in the protein fraction, and therefore, separable from the final protein concentrate.

In another embodiment of the disclosure, the protein fraction is mixed with a mixing solvent comprising an ethanol:water mixture, wherein the ethanol is present in an amount between 80% and 100%, optionally 90% and 100%, optionally 95% and 100% (v/v). It will be understood that 100% ethanol may contain a small percentage of impurities such as water, etc., which cannot be removed from the ethanol. In an embodiment, mixing solvent is added to the protein fraction at a ratio of between 2:1 and 1:2 (v/v of mixing solvent: protein fraction), optionally 1:1. In an embodiment, when the mixing solvent comprises an alcohol, such as ethanol (80%, 90%, 95% ethanol in water or 100% ethanol), soluble proteins in the protein fraction precipitate from solution, as a result the proteins being less soluble in the mixing solvent (such as ethanol) than in the blending solvent (such as water), and therefore increases the yield of the protein concentrate.

In another embodiment, the mixing solvent comprises an ethanol:water mixture, wherein the ethanol is present in an amount between 80% and 100% (v/v). The addition of the mixing solvent to the protein fraction from step iv(b) causes proteins in the protein fraction to precipitate as a result of the proteins having a lower solubility in such a solvent (such as ethanol/water mixture). Accordingly, the amount of protein recovered is increased upon separation.

In another embodiment, separating the precipitated proteins comprises using a centrifuge or a hydrocyclone. In another embodiment, separating the precipitated proteins comprises using a centrifuge, such as decanter centrifuge or disc stack centrifuge. In another embodiment, centrifuging the precipitated proteins comprises a g-force between 2,500 g and 9,500 g. When the centrifuge is operated at such a g-force, the precipitated proteins move along the radial axis to the bottom of the centrifuge tube and are easily separated from the supernatant.

In another embodiment, the process further comprises the step of drying the protein concentrate to a moisture of between 4% and 8% (w/w). In another embodiment, the protein concentrate also comprises peptides and free amino acids.

In another embodiment, the present disclosure also includes a process for the production of a protein isolate from macroalgae and/or microalgae comprising:
i) mixing the macroalgae and/or microalgae with a first blending solvent to form a mixture;
ii) optionally treating the mixture with phytase at a temperature and a pH suitable for phytase activity;
iii) optionally adjusting the pH of the mixture to a pH suitable to solubilize proteins;
iv) subjecting the mixture to a g-force sufficient to separate the mixture to form
  a) a fiber fraction, and
  b) a protein fraction comprising
    (i) an insoluble protein fraction, and
    (ii) a soluble protein fraction;
vi) separating the insoluble protein fraction from the soluble protein fraction to recover therefrom an insoluble protein concentrate and a soluble protein extract; and
vii) subjecting the soluble protein extract to filtration to recover therefrom the protein isolate.

In one embodiment, the pH of the mixture (algae and first blending solvent) is optionally adjusted to solubilize proteins (undenatured proteins) into the first blending solvent. In an embodiment, the pH of the mixture is adjusted to a pH between 6 and 8, optionally between 6.5 and 7.5, optionally about 7.0, using a base such as sodium hydroxide, which solubilizes some of the proteins present in the macroalgae and/or microalgae, and upon low g-force separation, increases the amount of protein in the protein fraction. In addition, adjusting the pH to about 7.0 results in the fiber fraction (after low g-force separation of the mixture) having a neutral pH as a by-product.

In another embodiment, the process further comprises mixing the fiber fraction with the first blending solvent and repeating step iv) once, twice or three times. The repeated washing of the fiber fraction with the blending solvent increases the amount of protein that is recovered for the protein concentrate as the repeated washings separates additional protein that is trapped within the fiber structure.

In another embodiment, the first and second blending solvents comprise water, a saline solution or a polysaccharide solution, optionally water, and wherein the ratio of the macroalgae and/or microalgae to the first blending solvent is 1:3 to 1:30 (w/w) of algae to water.

In another embodiment, the temperature suitable for phytase activity is between 20° and 60° C. and the pH suitable for phytase activity is between 2.0 and 7.0 and the temperature suitable for protease activity is between 30° and 70° C. and the pH suitable for protease activity is between 5.0 and 9.0.

In another embodiment, the mixture and/or the fiber mixture is subjected to a g-force of between 100 g and 500 g, optionally between 150 g and 400 g, or between 170 g and 350 g. In an embodiment, separating the mixture and/or the fiber mixture comprises using a centrifuge or a hydrocyclone, optionally in a decanter centrifuge.

In another embodiment, centrifuging to separate the insoluble protein fraction from the soluble protein fraction comprises a g-force between 2,500 g and 9,500 g. In another embodiment, the separation of the insoluble protein fraction from the soluble protein fraction results in a wet protein concentrate that can be subsequently dried. The extract from the separation of the insoluble protein fraction from the soluble protein fraction comprises the soluble protein, which is subsequently filtered through a filtration apparatus, such as ultrafiltration and/or diafiltration, resulting in the protein isolate. As described above, phytates and/or phytic acid can complex and bind to the proteins, and consequently block the filtration apparatus. The removal of the phytates and/or phytic acid from the macroalgae and/or microalgae mixture (macroalgae and/or microalgae and blending solvent) using phytase as described above, such that the filtration apparatus is not blocked with such complexes, resulting the filtration apparatus performing efficiently to produce the protein isolate.

In another embodiment, the process further comprises the step of drying the protein concentrate to a moisture of between 4% and 8% (w/w). In another embodiment, the protein concentrate also comprises peptides and free amino acids.

In another embodiment, any of the above processes is conducted using a counter-current process.

In another embodiment, there is also included a process for treating macroalgae and/or microalgae comprising a fiber fraction and a protein fraction, wherein the protein fraction comprises (i) an insoluble protein fraction and (ii) a soluble protein fraction, to separate the fiber fraction from the protein fraction comprising:

i) mixing the macroalgae and/or microalgae with a first blending solvent to form a mixture;

ii) optionally adjusting the pH of the mixture to a pH suitable to solubilize proteins in the mixture;

iv) subjecting the mixture to a g-force sufficient to separate the mixture to form
   a) a fiber fraction, and
   b) a protein fraction comprising
     (i) an insoluble protein fraction, and
     (ii) a soluble protein fraction; and v) separating the fiber fraction from the protein fraction.

In one embodiment, the separation at a g-force of between 150 to 300 g, optionally 150 to 200 g, optionally 175 to 180 g, comprises using any means to achieve such g-forces, such as a centrifuge, such as a decanter centrifuge, or a hydrocylcone.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The following non-limiting examples are illustrative of embodiments of the present disclosure:

EXAMPLES

Reagents and Materials

Commercial methyl pentane was purchased from Univar Canada Ltd., Saskatoon, Saskatchewan, Canada. Enzyme samples of Cellulase (Celluclast® 1.5 L), Cellulase Complex, Alcalase® 2.4L FG, and Flavourzyme® were obtained from Novozymes North America, Inc., Franklinton, N.C. USA.

Defatted microalgae were produced from dried microalgae (*Chlorella*) through the milling of microalgae in methyl pentane using a bead mill, solids-liquid separation by centrifugation using a decanter, desolventization and drying using a down draft desolventizer. Defatted macroalgae were produced from dried macroalgae (Kelp) through the milling of microalgae in methyl pentane using a bead mill, solids-liquid separation by centrifugation using a decanter, desolventization and drying using a down draft desolventizer.

Alcalase 2.4L FG was obtained from Novozymes North America, Inc., Franklinton, N.C. USA. Alcalase 2.4L FG is a proteolytic enzyme produced by submerged fermentation of a selected strain of *Bacillus licheniformis*.

Two samples of phytase (Natuphos. powder form, 10,000 FTU/g) and phytase (Natuphos. powder form, 55,000 FTU/g) were purchased from BASF Canada, Georgetown, Ontario, Canada.

Analysis

Mixing of the materials was performed using a Ribbon Blender (Torco Model R-12, Toronto Coppersmithing International Ltd., Scarborough, Ontario, Canada). Heat treatments of samples were conducted using an Infra Red Cereal Processing System (Micronizing Company Limited, Framlingham, Sulfolk, England) or a two-tray Simon-Rosedown cooker (Laboratory cooker-press, Simon-Rosedowns Limited, Hull, England). Ultrafiltration was carried out using a Millipore® Ultrafiltration Unit (Model A60, Millipore® Corporation, Bedford, Mass., USA). Protein content of the samples was determined by the Leco® Protein Analyzer (Model FP-428, Leco® Corporation, ST. Joseph, Mich. U.S.A.) based on AOCS Official Method Ba 4e-93. Moisture content of the samples was determined by drying samples in a 105±2° C. convection oven for 16 hours or to a constant weight based on AOCS Official Method Ba 2a-38. Oil content of the samples was determined based on AOCS Official Method Ba 3-38 with the following changes: (a) 2 g of sample was used instead of 5 g in the analysis; (b) extraction continued for 4 hours, and (c) extraction flask was heated to remove residual petroleum ethers. Ash content of the samples was determined based on AOCS Official Method Ba 5a-49 with the following changes: (a) samples were pre-ashed on a hot plate prior to being placed into the muffle furnace; (b) samples were incinerated for 18 hours in muffle furnace; and (c) nitric acid was added if sample remained black. Crude fiber content of the samples was determined based on AOCS Official Method Ba 6-84 with the following changes: (a) samples with oil contents below 3% were not defatted and (b) digest was dried for 2 hours at 130° C. Protein dispersibility index (PDI) of the samples was determined based on A.O.C.S. Official Method Ba 10-65. Free fatty acid (FFA) of the oil samples was determined based on AOCS Official Method Ca 5a-40. Phosphorus and sulphur of the samples were determined based on the modified methods of AOCS Ca20-99 and AOCS Ca 17-01 (modified), respectively. Crude fiber content of the samples was determined based on AOCS Official Method Ba 6-84 with the following changes: (a) samples with oil contents below 3% were not defatted and (b) digest was dried for 2 hours at 130° C. Protein dispersibility index (PDI) of the samples was determined based on A.O.C.S. Official Method Ba 10-65. Glucosinolate content of the samples was determined based on the Method of the Canadian Grain Commission, Grain Research Laboratory (Daun, J. K. and McGregor, D. I., Glucosinolate Analysis of Rapeseed (Canola), Dec. 15, 1981). Solvent residues were determined using GC/MS techniques based on a modified method of A.O.C.S. Official Method, Ba 13-87.

Example 1

Prophetic Preparation of Protein Concentrate Using Phytase from Algae

Approximately 15 kg dried microalgae or macroalgae is mixed with 120 kg of tab water at ambient temperature. Approximately 12 g of phytase (Natuphos 10,000 L Phytase) at 0.08% dosage based on the starting weight of dried microalgae or macroalgae is added to the slurry. The pH of algae slurry is adjusted to 5.5 and temperature to 50° C. After holding for 1.5 hours under agitation, the slurry is centrifuged at 180 g force (1500 RPM bowl speed) to separate fiber solids from algae protein slurry (slurry 1) containing soluble and insoluble proteins using a Bird Decanter (Bird 6" Continuous Bowl Decanter, Saskatoon, Canada). Fiber solids is mixed with water at a ratio of 1 to 1 by weight at ambient temperature, which is followed by centrifugation at 180 g force (1500 RPM bowl speed) to separate the $1^{st}$ washed fiber solids from the protein slurry (slurry 2) containing soluble and insoluble proteins using the Bird Decanter. The $1^{st}$ washed fiber solids are mixed with water at a ratio of 1 to 1 by weight at ambient temperature. This is followed by centrifugation at 180 g force (1500 RPM bowl speed) to separate the second washed fiber solids from the protein slurry (slurry 3) containing soluble and insoluble proteins using the Bird Decanter.

Algae protein slurries containing soluble and insoluble proteins are combined together. The protein slurry is mixed with 100% denatured ethanol (SDAG 13) at a volume ratio of 1 to 1 at ambient temperature under agitation. This is followed by centrifugation at 6,550 g force (8500 RPM) to recover precipitated proteins using a Westfalia Disc Stack Centrifuge (SA-7, Oelde, Germany). The precipitated proteins are washed with 85% ethanol (v/v) twice and centrifuged to recover the washed protein solids using a Basket Centrifuge (Tolhurst—26" Center-Slung, Ametek Inc., East Moline, Ill., USA). The recovered protein solids are desolventized in a fume hood before the final drying in a vacuum tray dryer to 5.59% moisture. The produced algae protein concentrate would contain above 50% protein, low fiber, and low anti-nutritional factors.

Example 2

Prophetic Preparation of Protein Concentrate Using Phytase from Algae

Approximately 40 kg of dried microalgae or macroalgae is mixed with 320 kg of tab water at ambient temperature. Approximately 32 g of phytase (Natuphos 10,000 L Phytase) at 0.08% dosage based on the starting weight of algae is added to the algae slurry. The pH of algae slurry is adjusted to 5.5 and temperature to 50° C. After holding for 1.5 hours under agitation, the algae slurry is centrifuged at 180 g force (1500 RPM bowl speed) to separate fiber solids from algae protein slurry (slurry 1) containing soluble and insoluble proteins using the Bird Decanter (Bird 6" Continuous Bowl Decanter, Saskatoon, Canada). Fiber solids are mixed with water at a ratio of 1 to 1 by weight at ambient temperature, which is followed by centrifugation at 180 g force (1500 RPM bowl speed) to separate the washed fiber solids from the algae protein slurry (slurry 2) containing soluble and insoluble proteins using the Bird Decanter.

Algae protein slurries containing soluble and insoluble proteins are combined together. The pH of combined protein slurry is adjusted to 4.5±0.1 by addition of 85% phosphoric acid. The protein slurry is heated to 95-100° C. for 10 to 60 minutes. The protein slurry is cooled down to 65° C. This is followed by centrifugation at 3,300 g force (5200 RPM bowl speed) to recover the majority of the precipitated proteins using a Westfalia Decanter Centrifuge (CA 225-010, Germany). The supernatant would still contain a small amount of fine precipitated proteins that would be recovered by centrifugation at 6,715 g force (7560 RPM) using a Westfalia Disc Stack Centrifuge (SA-14, Germany). The precipitated proteins are combined together, which is followed by mixing with water at a ratio of 1 to 3 by weight, at pH4.5 and at ambient temperature. The washed protein precipitates are recovered by centrifugation at 3,300 g using the Decanter at first, which is followed by centrifugation at 6,715 g using the Disc Stack Centrifuge to recover the remaining precipitated proteins. Finally, the washed protein precipitates are mixed with water at a ratio of 1 to 3 by weight, pH 4.5 and ambient temperature. The final washed protein precipitates are recovered by centrifugation using both the Decanter at 3,300 g and the Disc Stack Centrifuge at 6,715 g.

The final washed protein precipitates are dried to about 6% moisture. The algae protein concentrate would contain over 50% protein, low fiber, low ash and low anti-nutritional factors.

Example 3

Preparation of Protein Concentrate from Microalgae (i) Without Protein Hydrolysis—Control Approximately 0.5 kg of defatted microalgae (*Chlorella*) was mixed with 0.5 kg of water at ambient temperature. pH of the microalgae slurry was at 5.76. The slurry was heated to 50° C. Approximately 0.075 g of phytase (Natuphos, 55,000 FTU/g) was added to the slurry. The slurry was held at 50° C. for 1 hour under agitation. pH of the slurry was adjusted to 7.0 by addition of 10% NaOH solution. This was followed by centrifugation at 4,000 rpm for 10 minutes to separate the soluble extract from the insoluble solids using a lab centrifuge. The insoluble solids were washed with water twice. For each wash, the insoluble solids were mixed with water at a ratio of 1 to 2 by weight, which was followed by centrifugation at 4,000 rpm for 10 minutes to separate the washed insoluble solids from the washing extract. The washed solids were freeze dried into protein concentrate. The soluble extract was combined with the wash extracts. The combined liquid extract was subjected to untrafiltration and diafiltration in order to recover the soluble proteins and remove the ash.

(ii) Protein Hydrolysis with 0.5% Alcalase

Figure 35:
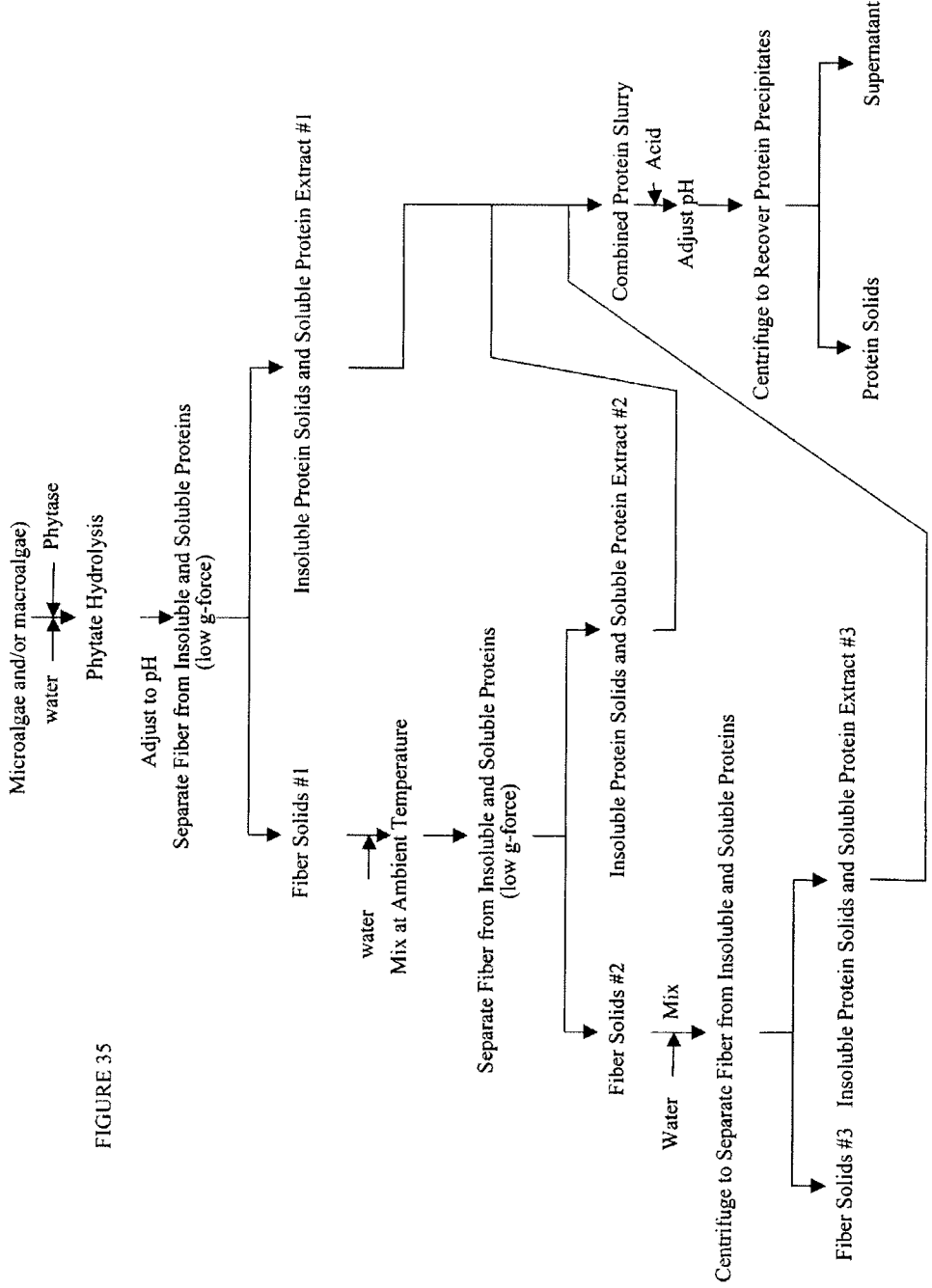
FIGS. 35. and 36 are schematic representations illustrating a preparation of a protein concentrate from microalgae and/or macroalgae meal using a protease.
Figure 36:
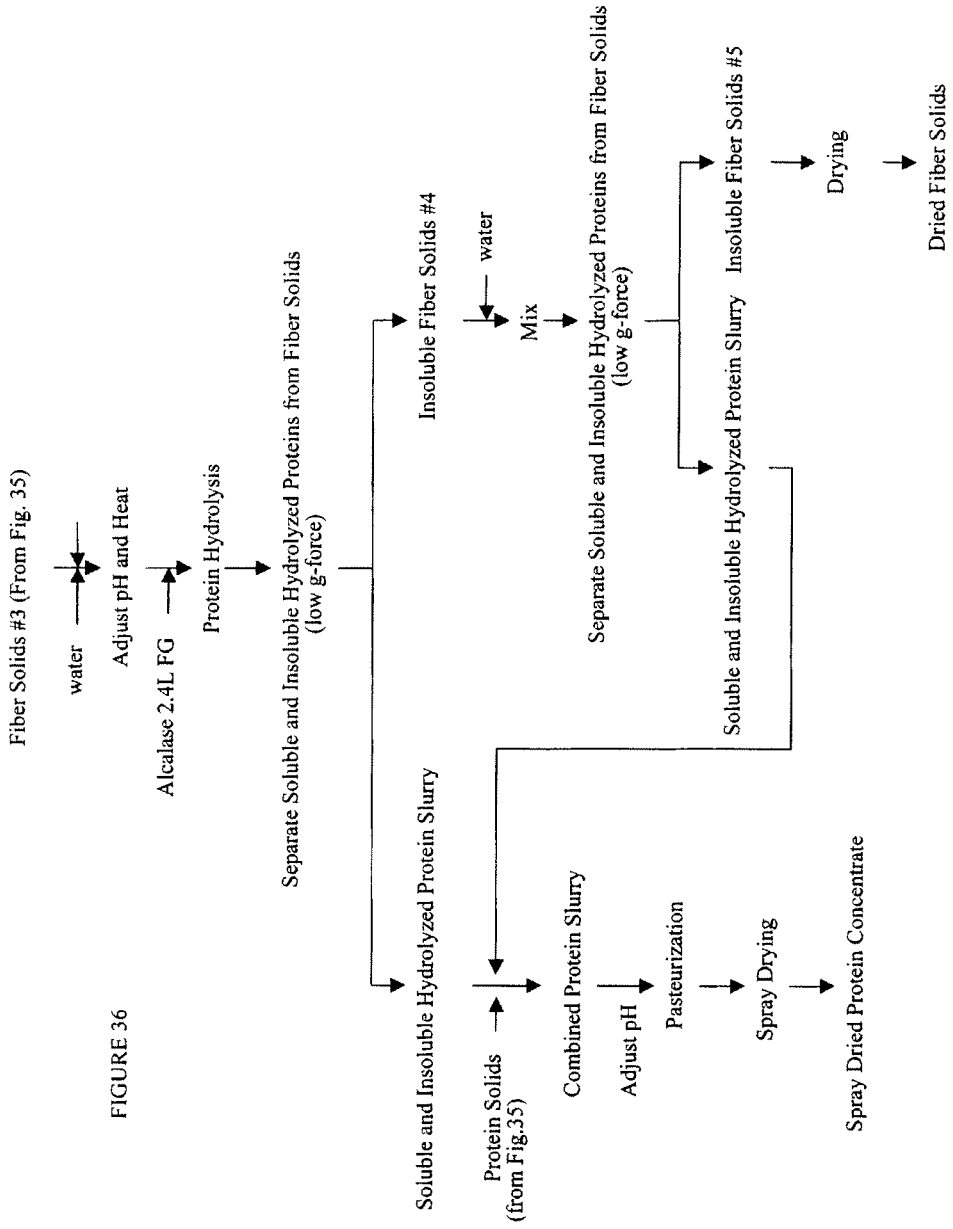

FIGS. 35 and 36 illustrate the preparation of a protein concentrate from a defatted microalgae meal using a protease. Approximately 100 g of defatted microalgae meal (*Chlorella*)

was mixed with 800 g of water at ambient temperature. The microalgae slurry had a pH 10, which was adjusted to 5.9.+−.0.2 by addition of 50% phosphoric acid. The microalgae slurry was heated to 52.+−.2.degree. C. and 0.3 g of phytase (Natuphos powder form, 10,000 FTU/g) was added to the slurry. Hydrolysis of phytates was carried out at 52.+−.2.degree. C. for 1 hour. After hydrolysis of phytates, the pH of microalgae slurry was adjusted to 7.0.+−.0.1 by slow addition of 10% NaOH solution.

After pH adjustment to 7.0±0.1, the microalgae slurry was centrifuged at 2,000 rpm for 10 minutes using a lab centrifuge. The soluble liquid extract was separated from the insoluble solids. The insoluble solids were mixed with water at a ratio of 1 to 1 by weight at ambient temperature, which was followed by centrifugation at 4,000 rpm for 10 minutes to separate the washed solids from the wash extract. The washed solids were washed with water three more times. For each wash, the insoluble solids were mixed with water at a ratio of 1 to 1 by weight. This was followed by centrifugation at 4,000 rpm to separate the washed solids from the wash extract. The soluble extract was combined with the washed extracts. The combined soluble extract was adjusted to lower pH by addition of 50% phosphoric acid to precipitate some proteins. The liquid extract was separated from precipitated proteins by centrifugation at 4,000 rpm for 10 minutes. The soluble liquid extract was subjected to ultrafiltration and diafiltration to recover soluble proteins and to remove ash.

The final washed solids were mixed with water at a ratio of 1 to 1 by weight. pH of the slurry was adjusted to 8.3±0.1 by addition of 10% NaOH solution. The slurry was heated to 60±2° C. 0.5 g of Alcalase (0.5% dosage based on the weight of defatted microalgae meal) was added to the slurry and protein hydrolysis was carried out at 60±2° C. for 2 hours. After protein hydrolysis, the slurry was centrifuged at 4,000 rpm for 10 minutes using the lab centrifuge. The hydrolyzed protein extract was separated from the insoluble solids by centrifugation at 4,000 rpm for 10 minutes using the lab centrifuge. The insoluble solids were mixed with water at a ratio of 1 to 1 by weight. This was followed by centrifugation at 4,000 rpm for 10 minutes using the lab centrifuge. The washed solids were again separated from the hydrolyzed protein extract.

The hydrolyzed protein extract was adjusted to pH7.0 before drying to produce the dried protein concentrate.

The washed solids after protein hydrolysis were also dried to produce the by-product of microalgae solids.

Discussion

The results of proximate analysis of defatted microalgae, protein concentrate and hydrolyzed protein concentrate are shown in Table 1. Defatted microalgae meal contains 54.8% protein and 0.46% phytates on a dry weight basis. The protein solubility index (PDI) is about 29.3%.

Hydrolyzed protein concentrate generated with the use of protease one another microalgae sample is show in Table 2. Hydrolyzed protein concentrate has a protein content of 58.88% (dwb). The remaining insoluble solids after protein hydrolysis and separation have a protein content of 13.4% (dwb). The process of protein hydrolysis with the use of protease was effective to solubilize the previous insoluble proteins. The process was also effective to reduce the ash and fiber contents. The ash content was reduced from 35.24% in the starting microalgae to 12.15% in the hydrolyzed protein concentrate. The fiber content was reduced from 5.96% in the starting microalgae meal to 2.94% in the hydrolyzed protein concentrate. The microalgae fiber solids have very high ash content of 41.24% and a high fiber content of 13.21% on a dry weight basis.

Figure 37:
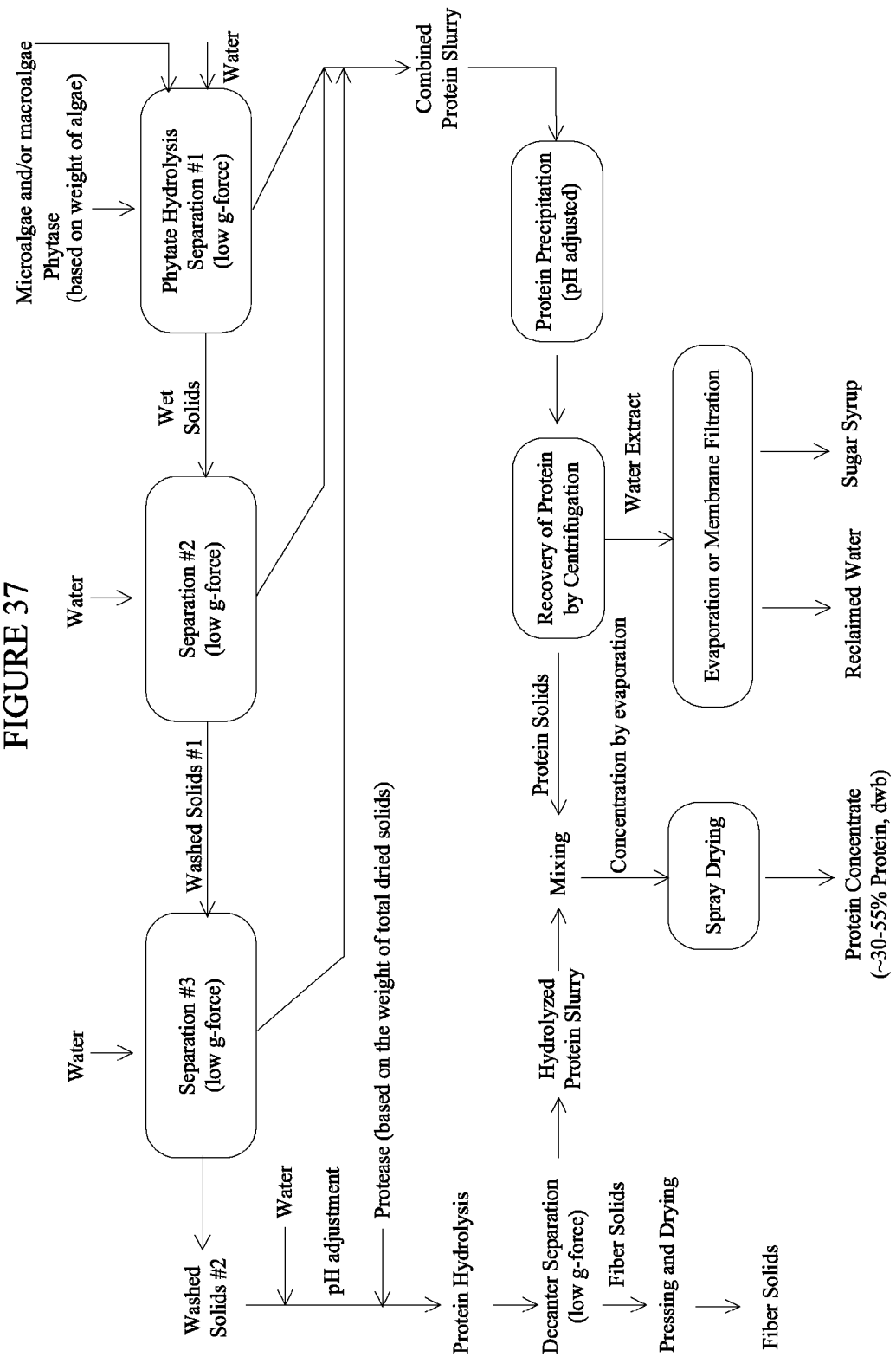
FIG. 37 is a schematic representation illustrating a preparation of a protein concentrate using a concurrent process.
Figure 38:
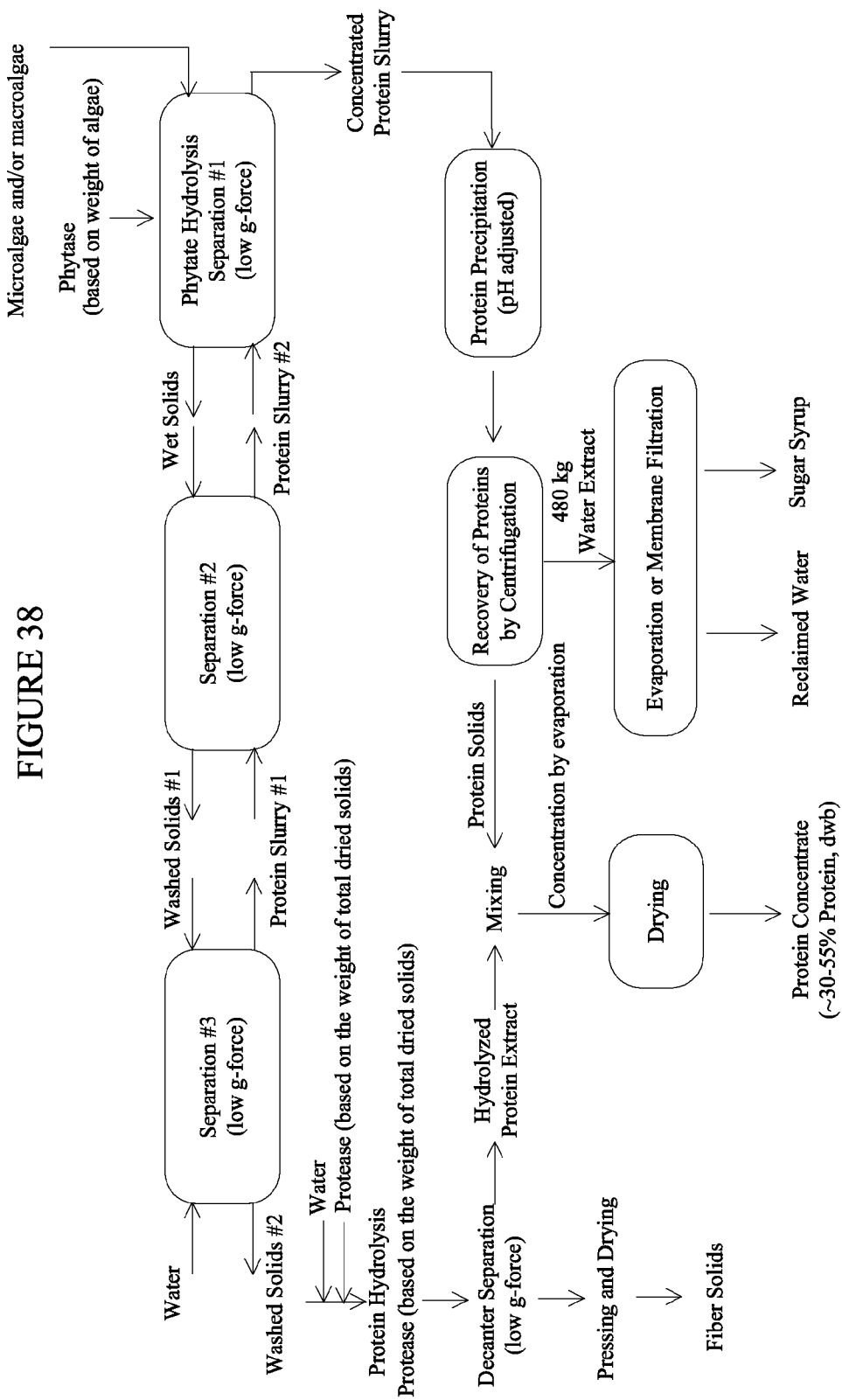
FIG. 38 is a schematic representation illustrating a preparation of a protein concentrate using a counter-current process.

As shown in FIGS. 37 and 38, the processes of the present disclosure are, in one embodiment, performed using a concurrent process (FIG. 37), or in another embodiment, a counter-current process (FIG. 38). In the counter-current process, there is substantial savings of water and energy as well as much better production throughput because the volume of the process streams is greatly reduced. For example, with a three stage counter-current process, the volume of the process streams can be reduced by 35-50%. This greatly reduces the amount of water used in the process. The volume of process streams is also greatly reduced leading to higher production throughput, short processing time and better processing efficiency. In addition, the amount of water to be removed from the production process is also greatly reduced resulting in energy savings.

TABLE 1

The Results of Proximate Analysis on Defatted Microalgae Meal (*Chlorella*), Protein Concentrate and Hydrolyzed Protein Concentrate.

| Sample | Moisture (%) | Protein (%, dwb) | Ash (%, dwb) | Oil (%, dwb) | Crude Fibre (%, dwb) | Phytates (%, dwb) | PDI |
|---|---|---|---|---|---|---|---|
| Defatted Microalgae (*Chlorella*) | 10.9 | 54.8 | 33.6 | 1.65 | 5.68 | 0.46 | 29.3 |
| Protein Concentrate | 5.21 | 58.1 | 5.48 | 0.77 | 1.45 | — | — |

TABLE 2

Results of Proximate Analysis on Defatted Microalgae Meal (*Chlorella*), Protein Concentrate and Hydrolyzed Protein Concentrate.

| Sample | Moisture (%) | Protein (%, dwb) | Ash (%, dwb) | Oil (%, dwb) | Crude Fibre (%, dwb) | Carbohydrate (%, dwb) |
|---|---|---|---|---|---|---|
| Defatted Microalgae (*Chlorella*) | 4.65 | 22.23 | 35.24 | 1.73 | 5.96 | 34.84 |
| Hydrolyzed Protein Concentrate | 2.86 | 58.88 | 12.15 | 2.14 | 2.94 | 23.89 |

TABLE 2-continued

Results of Proximate Analysis on Defatted Microalgae Meal (*Chlorella*),
Protein Concentrate and Hydrolyzed Protein Concentrate.

| Sample | Moisture (%) | Protein (%, dwb) | Ash (%, dwb) | Oil (%, dwb) | Crude Fibre (%, dwb) | Carbohydrate (%, dwb) |
|---|---|---|---|---|---|---|
| Microalgae Fiber Solids | 1.56 | 13.41 | 41.24 | 2.97 | 13.21 | 29.17 |

The invention claimed is:

1. A process for the production of one or more protein concentrates from defatted or milled macroalgae, microalgae or a combination thereof comprising the steps of:
 i) mixing the macroalgae, microalgae or a combination thereof with a first blending solvent to form a mixture;
 ii) optionally treating the mixture with phytase at a temperature and a pH suitable for phytase activity;
 iii) optionally adjusting the pH of the mixture to solubilize proteins in the mixture;
 iv) subjecting the mixture to a g-force sufficient to separate the mixture to form:
  a) a fiber fraction, and
  b) a protein fraction comprising;
   (i) an insoluble protein fraction, and
   (ii) a soluble protein fraction;
 v) separating the fiber fraction from the protein fraction and mixing the fiber fraction with a second blending solvent to form a fiber mixture;
 vi) treating the fiber mixture with a protease at a temperature and a pH suitable for protease activity;
 vii) subjecting the fiber mixture to a g-force sufficient to separate the fiber mixture to form:
  a) a second fiber fraction, and
  b) a hydrolyzed protein fraction, comprising
   (i) an insoluble protein fraction comprising partially hydrolyzed and un-hydrolyzed protein, and
   (ii) a soluble hydrolyzed protein fraction;
   optionally adjusting the pH of the protein fraction from step iv(b) to a pH suitable to precipitate proteins;
 viii) separating the precipitated proteins from the protein fraction, said separated precipitated protein comprising a first protein concentrate; and
 ix) optionally combining the first protein concentrate and the hydrolyzed protein fraction to form a second protein concentrate.

2. The process according to claim 1, wherein the process further comprises mixing the fiber fraction with the first blending solvent and repeating step iv) once, twice or three times.

3. The process according to claim 1, wherein the process further comprises mixing the second fiber fraction with the second blending solvent and repeating step vii) once, twice or three times.

4. The process according to claim 1, wherein the first and second blending solvents comprise water, a saline solution or a polysaccharide solution.

5. The process according to claim 4, wherein the first and second blending solvents comprise water.

6. The process according to claim 1, wherein the ratio of the macroalgae, microalgae or combination thereof to the first blending solvent is 1:3 to 1:30 (w/w) of algae to water.

7. The process according to claim 1, wherein the temperature suitable for phytase activity is between 20° and 60° C. and the pH suitable for phytase activity is between 2.0 and 7.0.

8. The process according to claim 1, wherein the temperature suitable for protease activity is between 30° and 70° C. and the pH suitable for protease activity is between 5.0 and 9.0.

9. The process according to claim 1, wherein the mixture, the fiber mixture or the mixture and fiber mixture are subjected to a g-force of between 100 g and 500 g.

10. The process according to claim 9, wherein the mixture, the fiber mixture or the mixture and fiber mixture are subjected to a g-force of between 150 g and 400 g.

11. The process according to claim 10, wherein the mixture, the fiber mixture or the mixture and fiber mixture are subjected to a g-force of between 170 g and 350 g.

12. The process according to claim 1, wherein separating the mixture, the fiber mixture or the mixture and fiber mixture comprises using a centrifuge or a hydrocyclone.

13. The process according to claim 1, wherein the pH suitable to precipitate the proteins in the protein fraction is between 4.0 and 6.0.

14. The process according to claim 1, further comprising the step of drying the protein concentrate to a moisture of between 4% and 8% (w/w).

15. The process according to claim 1, wherein the protein concentrate also comprises peptides and free amino acids.

16. The process according to claim 1, wherein the process is conducted as a counter-current process.

17. A process for the production of one or more protein concentrates from defatted or milled macroalgae, microalgae or a combination thereof comprising the steps of:
 i) mixing the toasted oilseed meal with a first blending solvent to form a mixture;
 ii) optionally treating the mixture with phytase at a temperature and a pH suitable for phytase activity;
 iii) optionally adjusting the pH of the mixture to solubilize proteins in the mixture;
 iv) subjecting the mixture to a g-force sufficient to separate the mixture to form:
  a) a fiber fraction, and
  b) a protein fraction comprising
   (i) an insoluble protein fraction, and
   (ii) a soluble protein fraction;
 v) separating the fiber fraction from the protein fraction and mixing the fiber fraction with a second blending solvent to form a fiber mixture;
 vi) treating the fiber mixture with a protease at a temperature and a pH suitable for protease activity;
 vii) subjecting the fiber mixture to a g-force sufficient to separate the fiber mixture to form:
  a) a second fiber fraction, and b) a hydrolyzed protein fraction, comprising
  (i) an insoluble protein fraction comprising partially hydrolyzed and unhydrolyzed protein, and
  (ii) a soluble hydrolyzed protein fraction;
viii) mixing the protein fraction from step iv(b) with a mixing solvent to precipitate proteins;
ix) separating the precipitated proteins from the protein fraction, said separated precipitated protein comprising a first protein concentrate; and
x) optionally combining the precipitated proteins first protein concentrate and the hydrolyzed protein fraction to form the a second protein concentrate.

18. The process according to claim 17, wherein the process further comprises mixing the fiber fraction with the first blending solvent and repeating step iv) once, twice or three times.

19. The process according to claim 17, wherein the process further comprises mixing the second fiber fraction with the second blending solvent and repeating step vii) once, twice or three times.

20. The process according to claim 17, wherein the first and second blending solvents comprise water, a saline solution or a polysaccharide solution.

21. The process according to claim 20, wherein the first and second blending solvents comprise water.

22. The process according to claim 17, wherein the ratio of the macroalgae, microalgae or a combination thereof to the first blending solvent is 1:3 to 1:30 (w/w) of algae to water.

23. The process according to claim 17, wherein the temperature suitable for phytase activity is between 20° and 60° C. and the pH suitable for phytase activity is between 2.0 and 7.0.

24. The process according to claim 17, wherein the temperature suitable for protease activity is between 30° and 70° C. and the pH suitable for protease activity is between 5.0 and 9.0.

25. The process according to claim 17, wherein the mixture is subjected to a g-force of between 100 g and 500 g.

26. The process according to claim 25, wherein the mixture is subjected to a g-force of between 150 g and 400 g.

27. The process according to claim 26, wherein the mixture is subjected to a g-force of between 170 g and 350 g.

28. The process according to claim 17, wherein separating the mixture comprises using a centrifuge or a hydrocyclone.

29. The process according to claim 17, wherein the mixing solvent comprises an ethanol:water mixture, wherein the ethanol is present in an amount between 80% and 100% (v/v).

30. The process according to claim 17, further comprising the step of drying the protein concentrate to a moisture of between 4% and 8% (w/w).

31. The process according to claim 17, wherein the protein concentrate also comprises peptides and amino acids.

32. The process according to claim 17, wherein the process is conducted as a counter-current process.

33. A process for the production of a protein isolate or a hydrolyzed protein isolate from defatted or milled macroalgae, microalgae or a combination thereof comprising the steps of:
  i) mixing macroalgae, microalgae or a combination thereof with a blending solvent to form a mixture;
  ii) optionally treating the mixture with phytase at a temperature and a pH suitable for phytase activity;
  iii) optionally adjusting the pH of the mixture to solubilize proteins in the mixture;
  iv) subjecting the mixture to a g-force sufficient to separate the mixture to form:
    a) a fiber fraction, and
    b) a protein fraction comprising
      (i) an insoluble protein fraction, and
      (ii) a soluble protein fraction;
  v) separating the insoluble protein fraction from the soluble protein fraction to recover therefrom an insoluble protein concentrate and a soluble protein extract; and
  vi) subjecting the soluble protein extract to membrane filtration to recover therefrom the protein isolate.

34. The process according to claim 33, wherein the process further comprises mixing the fiber fraction with the first blending solvent and repeating step iv) once, twice or three times.

35. The process according to claim 33, wherein the blending solvent comprises water, a saline solution or a polysaccharide solution.

36. The process according to claim 35, wherein the blending solvent comprises water.

37. The process according to claim 33, the ratio of the macroalgae, microalgae or combination thereof to the first blending solvent is 1:3 to 1:30 (w/w) of algae to water.

38. The process according to claim 33, wherein the temperature suitable for phytase activity is between 20° and 60° C. and the pH suitable for phytase activity is between 2.0 and 7.0.

39. The process according to claim 33, wherein the mixture is subjected to a g-force of between 100 g and 500 g.

40. The process according to claim 39, wherein the mixture is subjected to a g-force of between 150 g and 350 g.

41. The process according to claim 40, wherein the mixture is subjected to a g-force of between 170 g and 350 g.

42. The process according to claim 33, wherein separating the mixture comprises using a centrifuge or a hydrocyclone.

43. The process according to claim 33, further comprising the step of drying the protein isolate to a moisture of between 4% and 8% (w/w).

44. The process according to claim 33, wherein the protein isolate also comprises peptides and amino acids.

45. The process according to claim 33, wherein the protein isolate is hydrolyzed to produce peptides and free amino acids.

46. The process according to claim 33, wherein the process is conducted as a counter-current process.

* * * * *